(12) United States Patent
Stewart et al.

(10) Patent No.: US 9,273,166 B2
(45) Date of Patent: Mar. 1, 2016

(54) FUNCTIONALIZED RESINS OBTAINED VIA OLEFIN METATHESIS

(71) Applicant: ExxonMobil Chemical Patents Inc., Baytown, TX (US)

(72) Inventors: Ian C. Stewart, Houston, TX (US); John R. Hagadorn, Houston, TX (US); Mun F. Tse, Seabrook, TX (US); George Rodriguez, Houston, TX (US); Patrick Brant, Seabrook, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 310 days.

(21) Appl. No.: 14/032,066

(22) Filed: Sep. 19, 2013

(65) Prior Publication Data

US 2014/0088277 A1 Mar. 27, 2014

Related U.S. Application Data

(60) Provisional application No. 61/705,057, filed on Sep. 24, 2012.

(51) Int. Cl.

| | |
|---|---|
| *C08F 136/20* | (2006.01) |
| *C07C 13/45* | (2006.01) |
| *C07C 233/10* | (2006.01) |
| *C07C 57/26* | (2006.01) |
| *C07C 255/31* | (2006.01) |
| *C07C 67/343* | (2006.01) |
| *C07C 13/68* | (2006.01) |
| *C09J 123/14* | (2006.01) |
| *C08G 61/08* | (2006.01) |
| *C09J 165/00* | (2006.01) |
| *C08L 65/00* | (2006.01) |

(52) U.S. Cl.
CPC .............. *C08F 136/20* (2013.01); *C07C 13/45* (2013.01); *C07C 13/68* (2013.01); *C07C 57/26* (2013.01); *C07C 67/343* (2013.01); *C07C 233/10* (2013.01); *C07C 255/31* (2013.01); *C09J 123/14* (2013.01); *C07C 2103/91* (2013.01); *C08G 61/08* (2013.01); *C08G 2261/1644* (2013.01); *C08G 2261/3325* (2013.01); *C08G 2261/418* (2013.01); *C08G 2261/72* (2013.01); *C08L 65/00* (2013.01); *C09J 165/00* (2013.01)

(58) Field of Classification Search
CPC ...... C07C 13/45; C07C 57/26; C07C 233/10; C07C 255/31; C08F 136/20
See application file for complete search history.

(56) References Cited

U.S. PATENT DOCUMENTS

| | | | |
|---|---|---|---|
| 4,988,764 | A | 1/1991 | Nishio et al. |
| 5,616,153 | A | 4/1997 | Mike et al. |
| 6,100,224 | A | 8/2000 | Peiffer et al. |
| 6,111,027 | A | 8/2000 | Wright et al. |
| 6,225,432 | B1 | 5/2001 | Weng et al. |
| 7,183,359 | B2 | 2/2007 | Hanna et al. |
| 8,283,419 | B2 | 10/2012 | Hagadorn et al. |
| 8,372,930 | B2 | 2/2013 | Brant et al. |
| 8,399,725 | B2 | 3/2013 | Brant et al. |
| 2006/0178493 | A1 | 8/2006 | Maughon et al. |
| 2012/0077945 | A1 | 3/2012 | Holtcamp et al. |

FOREIGN PATENT DOCUMENTS

| | | |
|---|---|---|
| EP | 1 020 420 | 7/2000 |
| WO | 99/16845 | 4/1999 |
| WO | 03/025036 | 3/2003 |

(Continued)

OTHER PUBLICATIONS

Amin, S.B. et al., "Versatile Pathways for In Situ Polyolefin Functionalization with Heteroatoms: Catalytic Chain Transfer", Angewandte Chemie, International Edition, 2008, 47, pp. 2006-2025.

(Continued)

*Primary Examiner* — Robert Harlan
(74) *Attorney, Agent, or Firm* — Catherine L. Bell

(57) ABSTRACT

This invention relates to a reaction product obtained by contacting a polymer comprising units derived from dicyclopentadiene with a vinyl terminated macromonomer, a vinyl monomer or a vinylene monomer, in the presence of a metathesis catalyst, where the vinyl monomer or vinylene monomer is represented by the formula:

wherein
each X is, independently, $-CO_2R$, $-CONR_1R_2$, CN, a $C_1$ to a $C_{20}$ alkyl group;
R is a $C_1$ to a $C_{20}$ alkyl group or an aromatic group;
each $R_1$ and $R_2$ is, independently, a hydrogen, a $C_1$ to a $C_{20}$ alkyl group, or an aromatic group;
each $R_5$ is, independently, a hydrogen atom or a $C_1$ to a $C_{40}$ alkyl group;
each Ar is, independently, an aromatic group; and
each n is, independently, from 0 to about 40.

9 Claims, 6 Drawing Sheets

(56) References Cited

FOREIGN PATENT DOCUMENTS

| WO | 03/025037 | | 3/2003 |
|----|-----------|---|--------|
| WO | 03/025038 | | 3/2003 |
| WO | 03/025084 | | 3/2003 |
| WO | WO 03/025037 | A2 * | 3/2003 |
| WO | WO 03/025038 | A2 * | 3/2003 |
| WO | WO 03/025084 | A2 * | 3/2003 |

OTHER PUBLICATIONS

Astruc, D. et al., Cross Olefin Metathesis for the Selective Functionalization, Ferrocenylation, and Solubilization in Water of Olefin-Terminated Dendrimers, Polymers, and Gold Nanoparticles and for a Divergent Dendrimer Construction, J. Am. Chem. Soc. 2008, 130 pp. 1495-1506.

Astruc, D. et al., "Efficient Mono- and Bifunctionalization of Polyolefin Dendrimers by Olefin Metathesis", Angew. Chem. Int. Ed., 2005, 44, pp. 7399-7404.

Bielawski, C.W. et al., "Living ring-opening metathesis polymerization". Progress in Polymer Science 2007, vol. 32. Issue 1, pp. 1-29. See abstract: pp. 15-20; Figures 2, 4, 8-13 & 16.

Chung, T.C., "Synthesis of functional polyolefin copolymers with graft and block structures", Prog. Polym. Sci., 2002, 27, pp. 39-85.

Davidson, T.A. et al., "The Polymerization of Dicyclopentadiene: An Investigation of Mechanism", Journal of Molecular Catalysis A: Chemical, vol. 133, No. 1-2, Jul. 13, 1998, pp. 67-74.

Lopez R.G. et al., "Synthesis of well-defined polymer architectures by successive catalytic olefin polymerization and living/controlled polymerization reactions", Prog. Polym. Sci., 2007, 32 pp. 419-454.

Mathers, R. et al., "Functional hyperbranched polymers using ring-opening metathesis polymerization of dicyclopentadiene with monoterpenes", Macromolecules 2009, vol. 42. Issue 5, pp. 1512-1518. See pp. 1512-1514; Scheme 1.

Mathers, R.T. et al., "Cross Metathesis Functionalization of Polyolefins", Chemical Communications—Chemcom; Royal Society of Chemistry, No. 4, Feb. 21, 2004, pp. 422-423.

* cited by examiner

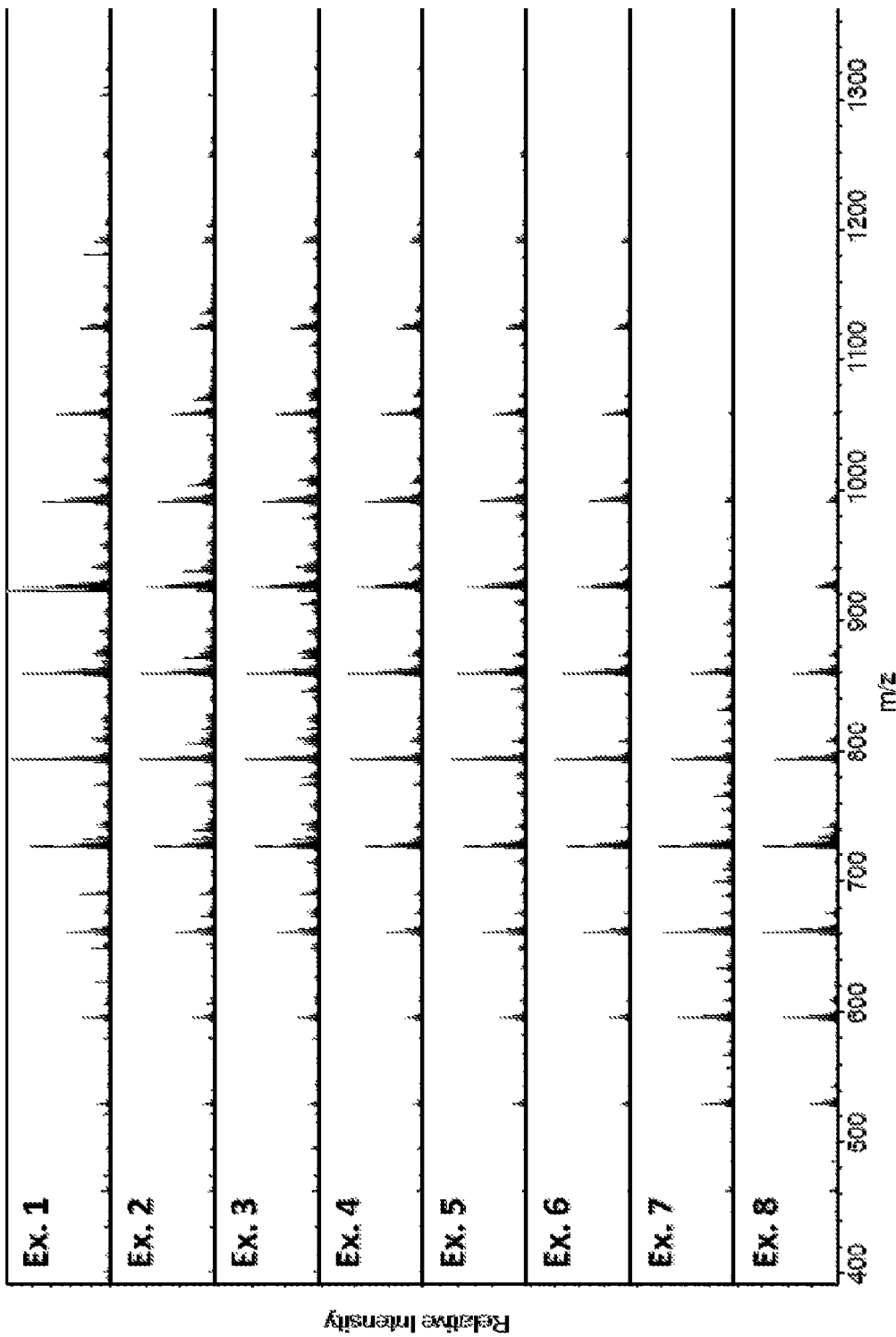
Figure 1. Mass Spectra for Examples 1-8.

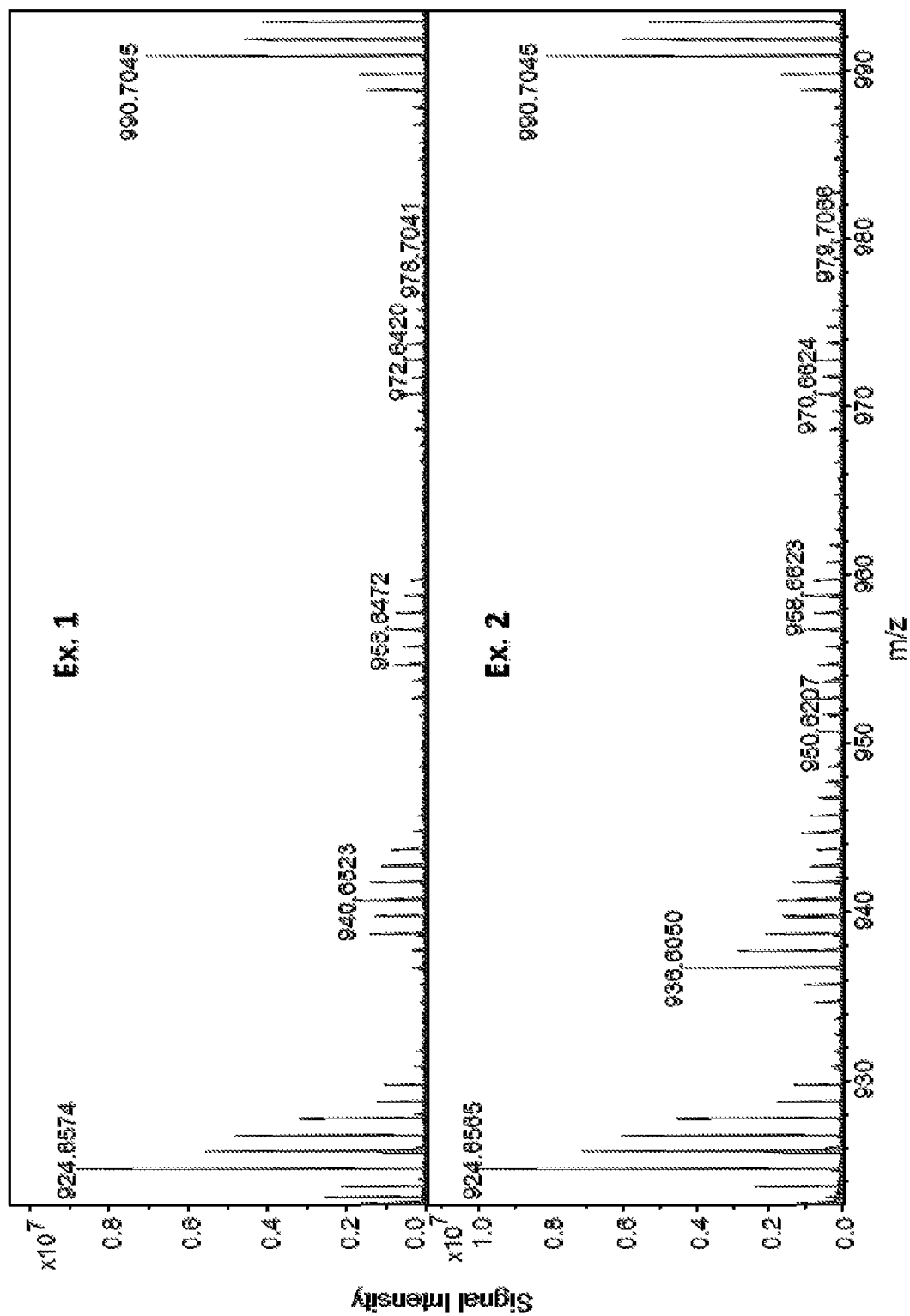
Figure 2. MS Spectra showing one repeat unit for Ex. 1-2.

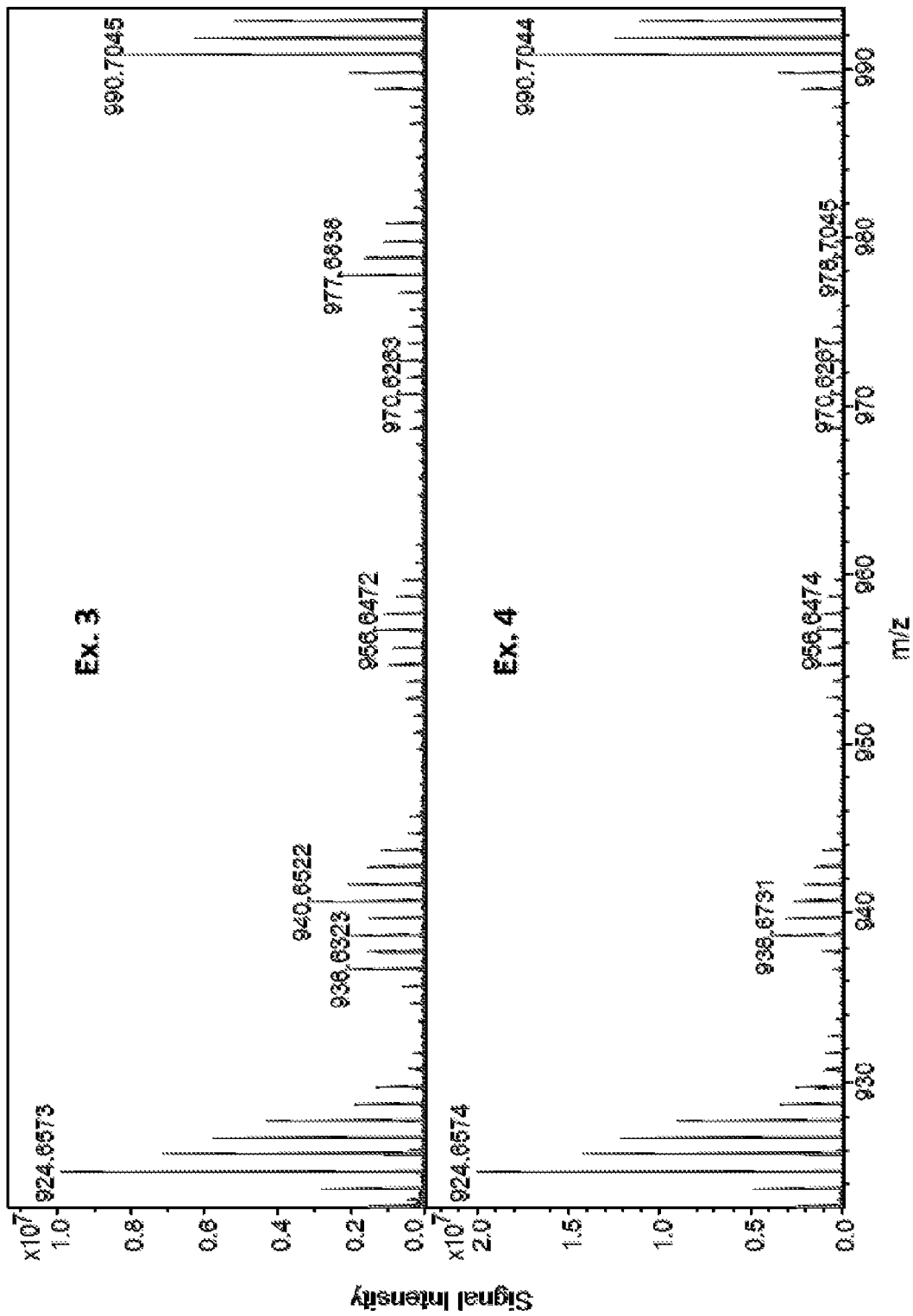
Figure 3. MS Spectra showing one repeat unit for Ex. 3-4.

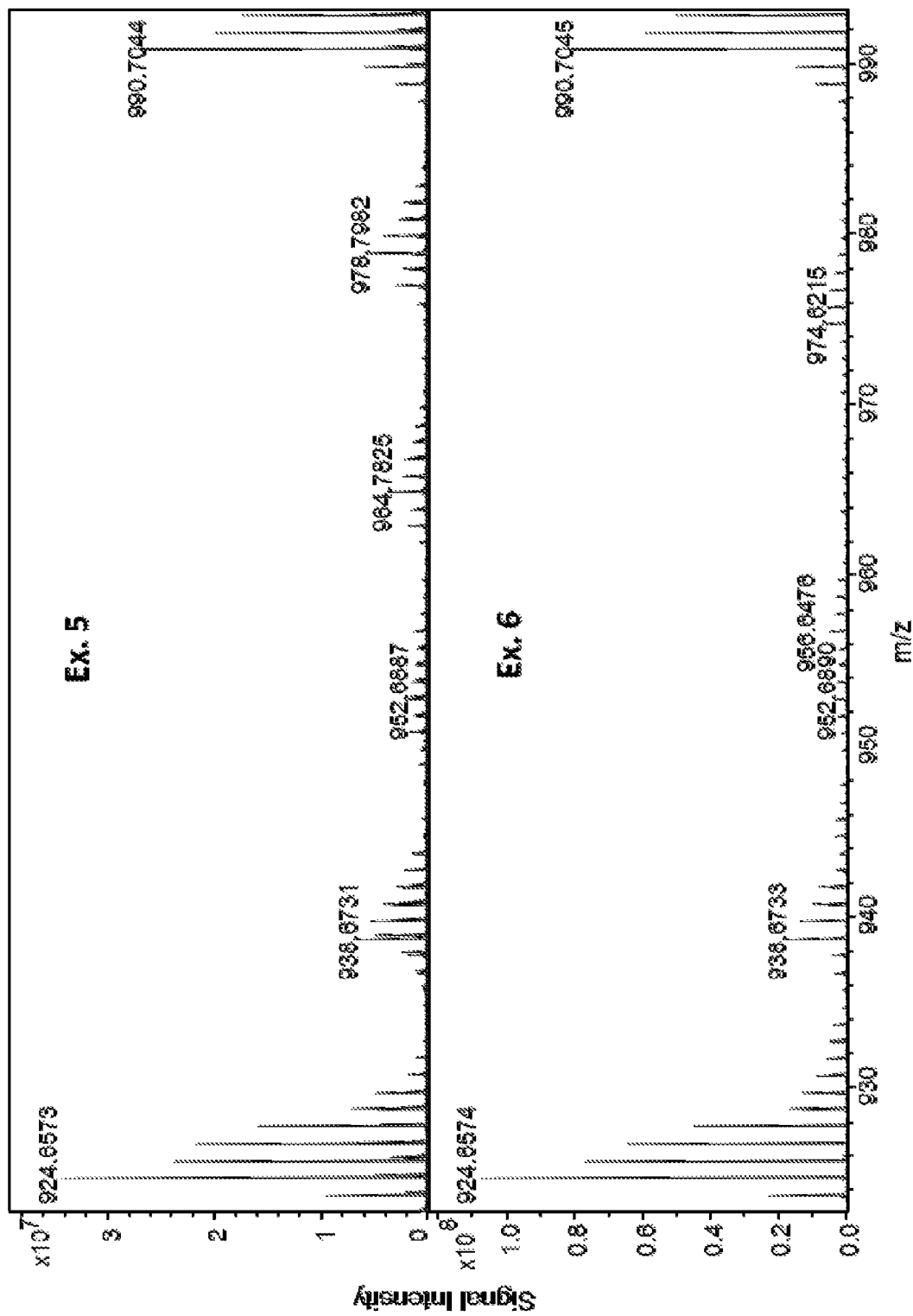
Figure 4. MS Spectra showing one repeat unit for Ex. 5-6.

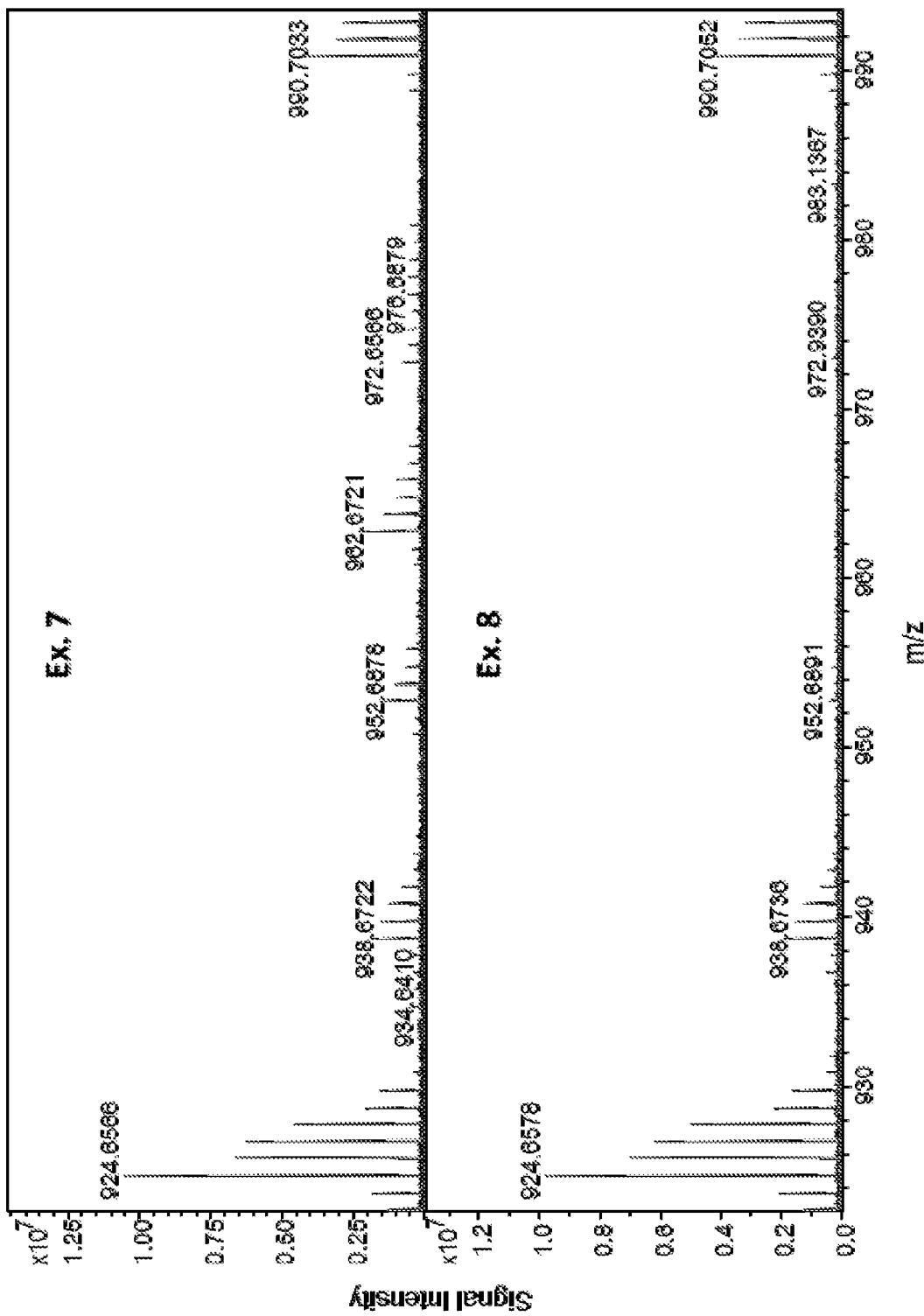
Figure 5. MS Spectra showing one repeat unit for Ex. 7-8.

Figure 6. Major peak list and assignments in one repeating unit (between m/z 924 to 990) for Examples 1-8.

| Example | Peak (m/z) | Peak Assignment | Example | Peak (m/z) | Peak Assignment |
|---|---|---|---|---|---|
| 1 | 924.6574 | $C_{70}H_{84}$ | 5 | 924.6573 | $C_{70}H_{84}$ |
|  | 940.6523 | $C_{70}H_{84}O$ |  | 938.6731 | $C_{71}H_{86}$ |
|  | 956.6472 | $C_{70}H_{84}O_2$ |  | 952.6887 | $C_{72}H_{88}$ |
|  | 972.6420 | $C_{70}H_{84}O_3$ |  | 956.6474 | $C_{70}H_{84}O_2$ |
|  | 990.7045 | $C_{75}H_{90}$ |  | 964.7825 | $C_{72}H_{100}$ |
| 2 | 924.6565 | $C_{70}H_{84}$ |  | 976.8764 | $C_{72}H_{112}$ |
|  | 936.6050 | $C_{66}H_{80}O_4$ |  | 978.7982 | $C_{73}H_{102}$ |
|  | 956.6472 | $C_{70}H_{84}O_2$ |  | 990.7044 | $C_{75}H_{90}$ |
|  | 970.6624 | $C_{71}H_{86}O_2$ | 6 | 924.6574 | $C_{70}H_{84}$ |
|  | 990.7045 | $C_{75}H_{90}$ |  | 938.6733 | $C_{71}H_{86}$ |
| 3 | 924.6573 | $C_{70}H_{84}$ |  | 944.6477 | $C_{69}H_{84}O_2$ |
|  | 936.6323 | $C_{66}H_{80}N_2$ |  | 956.6476 | $C_{70}H_{84}O_2$ |
|  | 956.6472 | $C_{70}H_{84}O_2$ |  | 974.6215 | $C_{69}H_{82}O_4$ |
|  | 977.6838 | $C_{73}H_{87}N$ |  | 990.7045 | $C_{75}H_{90}$ |
|  | 990.7045 | $C_{75}H_{90}$ | 7 | 924.6566 | $C_{70}H_{84}$ |
| 4 | 924.6574 | $C_{70}H_{84}$ |  | 938.6722 | $C_{71}H_{86}$ |
|  | 938.6731 | $C_{71}H_{86}$ |  | 952.6878 | $C_{72}H_{88}$ |
|  | 956.6474 | $C_{70}H_{84}O_2$ |  | 962.6721 | $C_{73}H_{86}$ |
|  | 970.6267 | $C_{70}H_{82}O_3$ |  | 972.6566 | $C_{74}H_{84}$ |
|  | 990.7044 | $C_{75}H_{90}$ |  | 976.6879 | $C_{74}H_{88}$ |
|  |  |  |  | 990.7033 | $C_{75}H_{90}$ |
|  |  |  | 8 | 924.6578 | $C_{70}H_{84}$ |
|  |  |  |  | 938.6736 | $C_{71}H_{86}$ |
|  |  |  |  | 952.6891 | $C_{72}H_{88}$ |
|  |  |  |  | 990.7052 | $C_{75}H_{90}$ |

FUNCTIONALIZED RESINS OBTAINED VIA OLEFIN METATHESIS

CROSS-REFERENCE TO RELATED APPLICATION

This application claims priority to and the benefit of U.S. Provisional Application No. 61/705,057, filed Sep. 24, 2012, the disclosure of which is incorporated herein by reference in its entirety.

FIELD OF THE INVENTION

This invention relates to the introduction of polar groups into poly(dicyclopentadiene) resins by olefin metathesis using ruthenium-based catalysts.

BACKGROUND OF THE INVENTION

Metathesis is generally thought of as the interchange of radicals between two compounds during a chemical reaction. There are several varieties of metathesis reactions, such as ring opening metathesis, acyclic diene metathesis, ring closing metathesis, and cross metathesis. These reactions, however, have had limited success with the metathesis of functionalized olefins.

Methods for the production of polyolefins with end-functionalized groups are typically multi-step processes that often create unwanted by-products and waste of reactants and energy.

R. T. Mathers and G. W. Coates *Chem. Commun.,* 2004, pp. 422-423 disclose examples of using cross-metathesis to functionalize polyolefins containing pendant vinyl groups to form polar-functionalized products with a graft-type structure.

D. Astruc et al. *J. Am. Chem. Soc.* 2008, 130, pp. 1495-1506, and D. Astruc et al. *Angew. Chem. Int. Ed.,* 2005, 44, pp. 7399-7404 disclose examples of using cross metathesis to functionalize non-polymeric molecules containing vinyl groups.

For reviews of methods to form end-functionalized polyolefins, see: (a) S. B. Amin and T. J. Marks, *Angew. Chem. Int. Ed.,* 2008, 47, pp. 2006-2025; (b) T. C. Chung *Prog. Polym. Sci.,* 2002, 27, pp. 39-85; and (c) R. G. Lopez, F. D'Agosto, C. Boisson *Prog. Polym. Sci.,* 2007, 32, pp. 419-454.

U.S. Pat. No. 8,399,725 discloses certain vinyl terminated oligomers and polymers that are functionalized, optionally, for use in lubricant applications.

U.S. Pat. No. 8,372,930 discloses certain vinyl terminated oligomers and polymers that are functionalized in U.S. Pat. No. 8,399,725.

U.S. Pat. No. 8,283,419 discloses end functionalized polyolefins prepared from vinyl terminated polyolefins by cross metathesis.

Additional references of interest include U.S. Pat. Nos. 4,988,764; 6,225,432; 6,111,027; 7,183,359; 6,100,224; 5,616,153; PCT Publication Nos. WO 03/025084; WO 03/025038; WO 03/025037; WO 03/025036; and WO 99/016845.

Thus, metathesis reactions can provide functionalized polyolefins that have end-functionalization. However, to date it has not been feasible to polymerize polyolefins having end-functionalization to each other.

Thus, a need exists for a method to prepare polyolefins that utilize end-functionalization to provide new polymers with unique physical properties.

SUMMARY OF THE INVENTION

This invention relates to the reaction product obtained by contacting a polymer comprising units derived from dicyclopentadiene and a vinyl monomer or vinylene monomer in the presence of a metathesis catalyst, where the vinyl monomer or vinylene monomer is represented by the formula:

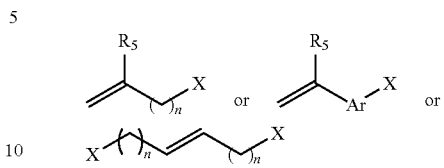

wherein
each X is, independently, $-CO_2R$, $-CONR_1R_2$, $CN$, a $C_1$ to a $C_{20}$ alkyl group;
R is a $C_1$ to a $C_{20}$ alkyl group or an aromatic group;
each $R_1$ and $R_2$ is, independently, a hydrogen, a $C_1$ to a $C_{20}$ alkyl group, or an aromatic group;
each $R_5$ is, independently, a hydrogen atom or a $C_1$ to a $C_{40}$ alkyl group;
each Ar is, independently, an aromatic group; and
each n is, independently, from 0 to about 40.

This inventions relates to the reaction product obtained by contacting a polymer comprising units derived from dicyclopentadiene and a vinyl terminated macromonomer in the presence of a metathesis catalyst.

This invention relates to a composition comprising one or more of the formulae:

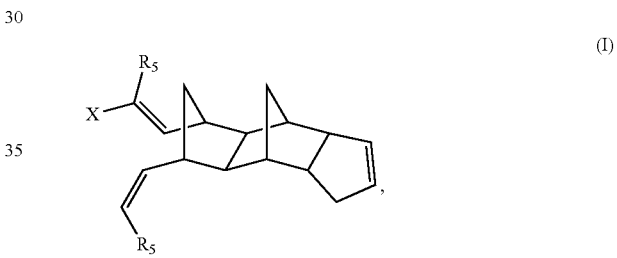
(I)

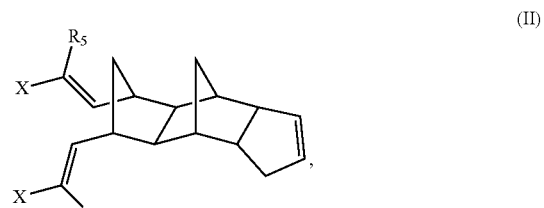
(II)

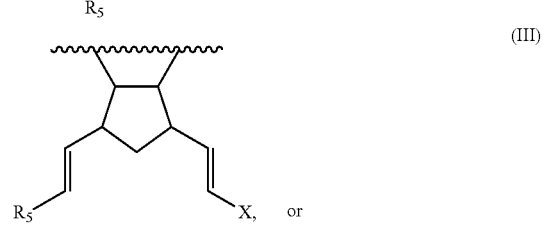
(III)

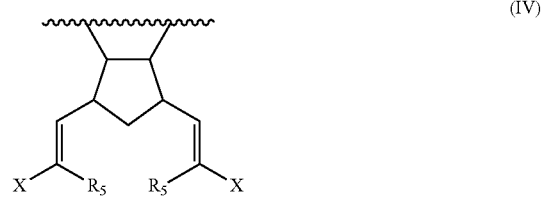
(IV)

wherein,
optionally, one or more positions on the polymeric backbone ( ᴧᴧᴧᴧᴧ ) can be substituted with an aromatic group;

each X is, independently, —$CO_2R$, —$CONR_1R_2$, —$CH_2CO_2R$, —$CH_2CONR_1R_2$, CN, a $C_1$ to a $C_{20}$ alkyl group or the residual terminal portion of a vinyl terminated macromonomer (VTM);

wherein,

R is a $C_1$ to a $C_{20}$ alkyl group or an aromatic group;

each $R_1$ and $R_2$ is, independently, a hydrogen, a $C_1$ to a $C_{20}$ alkyl group, or an aromatic group; and each $R_5$ is, independently, a hydrogen atom or a $C_1$ to a $C_{40}$ alkyl group.

Hydrocarbon resins are attractive in the marketplace due to their low cost, and numerous end applications. However, the lack of polarity in these resins limits their: (1) compatibility with polar polymers (e.g., vinyl acetates), (2) adhesion to polar surfaces (e.g., glass, cardboard, other natural fibers), and (3) ability to disperse fillers (e.g., minerals, carbon black), among other deficiencies. Converting this low-cost feed into a higher-value product via economic, catalytic processes is therefore an attractive target.

Polymerization of dicyclopentadiene (DCPD) is performed commercially today. These materials, prior to hydrogenation, contain a highly-strained cyclic olefins. This strain energy can be used to drive ring-opening cross metathesis (ROCM) reactions. Modern Ru-based olefin metathesis catalysts are known for their high tolerance to polar functional groups, and are therefore well-suited to this challenge.

BRIEF DESCRIPTION OF THE FIGURES

FIG. 1 is a representative depiction of the mass spectra for Examples 1 through 8.

FIG. 2 is a mass spectra showing one repeat unit for Examples 1 and 2.

FIG. 3 is a mass spectra showing one repeat unit for Examples 3 and 4.

FIG. 4 is a mass spectra showing one repeat unit for Examples 5 and 6.

FIG. 5 is a mass spectra showing one repeat unit for Examples 7 and 8.

FIG. 6 is a tabular form of the major peak assignments in a repeating unit of a m/z from 924 to 990 for Examples 1 through 8.

DETAILED DESCRIPTION OF THE INVENTION

Definitions

In the structures depicted throughout this specification and the claims, a solid line indicates a bond, and an arrow indicates that the bond may be dative.

As used herein, the new notation for the Periodic Table Groups is used as described in *Chemical and Engineering News,* 63(5), p. 27 (1985).

The term "substituted" means that a hydrogen group has been replaced with a hydrocarbyl group, a heteroatom, or a heteroatom containing group. For example, methyl cyclopentadiene (Cp) is a Cp group substituted with a methyl group and ethyl alcohol is an ethyl group substituted with an —OH group.

The terms "hydrocarbyl radical," "hydrocarbyl," and "hydrocarbyl group" are used interchangeably throughout this document. Likewise, the terms "functional group," "group," and "substituent" are also used interchangeably in this document. For purposes of this disclosure, "hydrocarbyl radical" is defined to be $C_1$ to $C_{20}$ radicals, that may be linear, branched, or cyclic (aromatic or non-aromatic); and may include substituted hydrocarbyl radicals as defined herein. In an embodiment, a functional group may comprise a hydrocarbyl radical, a substituted hydrocarbyl radical, or a combination thereof.

Substituted hydrocarbyl radicals are radicals in which at least one hydrogen atom has been substituted with a heteroatom or heteroatom containing group, or with atoms from Groups 13, 14, 15, 16, and 17 of the Periodic Table of Elements, or a combination thereof, or with at least one functional group, such as halogen (Cl, Br, I, F), $NR*_2$, $OR*$, $SeR*$, $TeR*$, $PR*_2$, $AsR*_2$, $SbR*_2$, $SR*$, $BR*_2$, $SiR*_3$, $GeR*_3$, $SnR*_3$, $PbR*_3$, and the like or where at least one heteroatom has been inserted within the hydrocarbyl radical, such as halogen (Cl, Br, I, F), O, S, Se, Te, $NR*$, $PR*$, $AsR*$, $SbR*$, $BR*$, $SiR*_2$, $GeR*_2$, $SnR*_2$, $PbR*_2$, and the like, where $R*$ is, independently, hydrogen or a hydrocarbyl radical, or any combination thereof.

In an embodiment, the hydrocarbyl radical is independently selected from methyl, ethyl, ethenyl, and isomers of propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, and triacontynyl. Also included are isomers of saturated, partially unsaturated, and aromatic cyclic structures wherein the radical may additionally be subjected to the types of substitutions described above. Examples include phenyl, methylphenyl, benzyl, methylbenzyl, naphthyl, cyclohexyl, cyclohexenyl, methylcyclohexyl, and the like. For this disclosure, when a radical is listed, it indicates that radical type and all other radicals formed when that radical type is subjected to the substitutions defined above. Alkyl, alkenyl, and alkynyl radicals listed include all isomers including, where appropriate, cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (analogous substituted cyclobutyls and cyclopropyls); and butenyl includes E and Z forms of 1-butenyl, 2-butenyl, 3-butenyl, 1-methyl-1-propenyl, 1-methyl-2-propenyl, 2-methyl-1-propenyl, and 2-methyl-2-propenyl (cyclobutenyls and cyclopropenyls). Cyclic compounds having substitutions include all isomer forms, for example, methylphenyl would include ortho-methylphenyl, meta-methylphenyl, and para-methylphenyl; dimethylphenyl would include 2,3-dimethylphenyl, 2,4-dimethylphenyl, 2,5-dimethylphenyl, 2,6-diphenylmethyl, 3,4-dimethylphenyl, and 3,5-dimethylphenyl.

An "olefin," alternatively referred to as "alkene," is a linear, branched, or cyclic compound of carbon and hydrogen having at least one double bond. For purposes of this specification and the claims appended thereto, when a polymer or copolymer is referred to as comprising an olefin, including, but not limited to, ethylene, propylene, and butene, the olefin present in such polymer or copolymer is the polymerized form of the olefin. For example, when a copolymer is said to have an "ethylene" content of 35 wt % to 55 wt %, it is understood that the mer unit in the copolymer is derived from ethylene in the polymerization reaction and said derived units are present at 35 wt % to 55 wt %, based upon the weight of the copolymer. A "polymer" has two or more of the same or different mer units. A "homopolymer" is a polymer having mer units that are the same. A "copolymer" is a polymer having two or more mer units that are different from each other. A "terpolymer" is a polymer having three mer units that are different from each other. "Different" as used to refer to mer units indicates that the mer units differ from each other by at least one atom or are different isomerically. Accordingly, the definition of copolymer, as used herein, includes terpolymers and the like. An oligomer is a polymer having a low molecular weight. In some embodiments, an oligomer has an Mn of 21,000 g/mol or less (e.g., 2,500 g/mol or less); in other embodiments, an oligomer has a low number of mer units (such as 75 mer units or less).

An "alpha-olefin" is an olefin having a double bond at the alpha (or 1-) position. A "linear alpha-olefin" or "LAO" is an olefin with a double bond at the alpha position and a linear hydrocarbon chain. A "polyalphaolefin" or "PAO" is a polymer having two or more alpha-olefin units. For the purposes of this disclosure, the term "α-olefin" includes $C_2$-$C_{20}$ olefins. Non-limiting examples of α-olefins include ethylene, propylene, 1-butene, 1-pentene, 1-hexene, 1-heptene, 1-octene, 1-nonene, 1-decene, 1-undecene 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, 4-methyl-1-pentene, 3-methyl-1-pentene, 5-methyl-1-nonene, 3,5,5-trimethyl-1-hexene, vinylcyclohexane, and vinylnorbornane. Non-limiting examples of cyclic olefins and diolefins include cyclopropene, cyclobutene, cyclopentene, cyclohexene, cycloheptene, cyclooctene, cyclononene, cyclodecene, norbornene, 4-methylnorbornene, 2-methylcyclopentene, 4-methylcyclopentene, vinylcyclohexane, norbornadiene, dicyclopentadiene, 5-ethylidene-2-norbornene, vinylcyclohexene, 5-vinyl-2-norbornene, 1,3-divinylcyclopentane, 1,2-divinylcyclohexane, 1,3-divinylcyclohexane, 1,4-divinylcyclohexane, 1,5-divinylcyclooctane, 1-allyl-4-vinylcyclohexane, 1,4-diallylcyclohexane, 1-allyl-5-vinylcyclooctane, and 1,5-diallylcyclooctane.

For purposes herein, a polymer or polymeric chain comprises a concatenation of carbon atoms bonded to each other in a linear or a branched chain, which is referred to herein as the backbone of the polymer (e.g., polyethylene). The polymeric chain may further comprise various pendent groups attached to the polymer backbone which were present on the monomers from which the polymer was produced. These pendent groups are not to be confused with branching of the polymer backbone, the difference between pendent side chains and both short and long chain branching being readily understood by one of skill in the art.

The terms "catalyst" and "catalyst compound" are defined to mean a compound capable of initiating catalysis. In the description herein, the catalyst may be described as a catalyst precursor, a pre-catalyst compound, or a transition metal compound (for example, a metallocene compound), and these terms are used interchangeably. A catalyst compound may be used by itself to initiate catalysis or may be used in combination with an activator to initiate catalysis. When the catalyst compound is combined with an activator to initiate catalysis, the catalyst compound is often referred to as a pre-catalyst or catalyst precursor. A "catalyst system" is a combination of at least one catalyst compound, an optional activator, an optional co-activator, and an optional support material, where the system can polymerize monomers to polymer. For the purposes of this invention and the claims thereto, when catalyst systems are described as comprising neutral stable forms of the components, it is well understood by one of ordinary skill in the art, that the ionic form of the component is the form that reacts with the monomers to produce polymers.

An "anionic ligand" is a negatively charged ligand which donates one or more pairs of electrons to a metal ion. A "neutral donor ligand" is a neutrally charged ligand which donates one or more pairs of electrons to a metal ion.

A "scavenger" is a compound that is typically added to facilitate polymerization by scavenging impurities. Some scavengers may also act as activators and may be referred to as co-activators. A co-activator, that is not a scavenger, may also be used in conjunction with an activator in order to form an active catalyst. In some embodiments, a co-activator can be pre-mixed with the catalyst compound to form an alkylated catalyst compound, also referred to as an alkylated invention compound.

A propylene polymer is a polymer having at least 50 mol % of propylene. As used herein, Mn is number average molecular weight as determined by proton nuclear magnetic resonance spectroscopy ($^1$H NMR) where the data is collected at 120° C. in a 5 mm probe using a spectrometer with a $^1$H frequency of at least 400 MHz. Data is recorded using a maximum pulse width of 45°, 8 seconds between pulses and signal averaging 120 transients. Unless stated otherwise, Mw is weight average molecular weight as determined by gel permeation chromatography (GPC), Mz is z average molecular weight as determined by GPC as described in the VINYL TERMINATED MACROMONOMERS section below, wt % is weight percent, and mol % is mole percent. Molecular weight distribution (MWD) is defined to be Mw (GPC) divided by Mn (GPC). Unless otherwise noted, all molecular weight units, e.g., Mw, Mn, Mz, are g/mol.

The following abbreviations may be used through this specification: Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, nBu is normal butyl, TMS is trimethylsilyl, TIBAL is tri-isobutylaluminum, TNOAL is triisobutyl n-octylaluminum, MAO is methylalumoxane, pMe is para-methyl, Ar* is 2,6-diisopropylaryl, Bz is benzyl, THF is tetrahydrofuran, DCPD is dicyclopentadiene, and tol is toluene.

This inventions relates to the reaction product obtained by contacting a polymer comprising units derived from dicyclopentadiene and a vinyl monomer or vinylene monomer in the presence of a metathesis catalyst, where the vinyl monomer or vinylene monomer is represented by the formula:

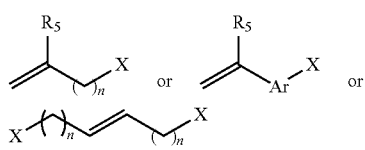

wherein
each X is, independently, —$CO_2R$, —$CONR_1R_2$, CN, a $C_1$ to a $C_{20}$ alkyl group;
R is a $C_1$ to a $C_{20}$ alkyl group or an aromatic group;
each $R_1$ and $R_2$ is, independently, a hydrogen, a $C_1$ to a $C_{20}$ alkyl group, or an aromatic group;

each $R_5$ is, independently, a hydrogen atom or a $C_1$ to a $C_{40}$ alkyl group;

each Ar is, independently, an aromatic group; and each n is, independently, from 0 to about 40.

The phrase "units derived from dicyclopentadiene" includes units derived from substituted DCPD such as methyl DCPD or dimethyl DCPD.

In embodiments, the inventions also relates to the reaction product obtained by contacting a polymer comprising units derived from dicyclopentadiene and a vinyl terminated macromonomer in the presence of a metathesis catalyst.

In a preferred embodiment of the invention the polymer comprising units derived from dicyclopentadiene (also referred to as the "DCPD polymer") has an Mw of from 150 to 10,000 g/mol (as determined by GPC), preferably from 200 to 5,000 g/mol, preferably from 300 to 1000 g/mol.

In a preferred embodiment of the invention the DCPD polymer comprises up to 100 mol % units derived from dicyclopentadiene, alternately from 5 to 90 mol % units derived from DCPD, alternately from 5 to 70 mol % unites derived from DCPD. In an embodiment of the invention, the DCPD polymer is preferably made from a monomer mixture comprising from 15% to 70% piperylene components, from 5% to 70% cyclic components (such as DCPD), and from 10% to 30% aromatic, preferably styrenic components. Alternatively, or additionally, in an embodiment, the DCPD polymer comprises an interpolymer of from 30% to 60% units derived from at least one piperylene component, from 10% to 50% units derived from at least one cyclic pentadiene component, and from 10% to 25% units derived from at least one styrenic component. The monomer mixture or the interpolymer may optionally comprise up to 5% isoprene, up to 10% amylene components, up to 5% indenic components, or any combination thereof. The monomer mixture is contacted with heat or a carbocationic catalyst to interpolymerize the monomers as disclosed in WO 2012/050658.

In a preferred embodiment of the invention, the DCPD polymer has a refractive index greater than 1.5.

In a preferred embodiment of the invention, the DCPD polymer has a softening point of 80° C. or more (Ring and Ball, as measured by ASTM E-28) preferably from 80° C. to 150° C., preferably 100° C. to 130° C. In another embodiment the resins is liquid and has a softening point of between 10° C. and 70° C.

In a preferred embodiment of the invention the DCPD polymer has a glass transition temperature (Tg) (as measured by ASTM E 1356 using a TA Instruments model 2920 machine) of from −65° C. to 30° C.

In a preferred embodiment of the invention, the DCPD polymer has a Brookfield Viscosity (ASTM D-3236) measured at the stated temperature (typically from 120° C. to 190° C.) using a Brookfield Thermosel viscometer and a number 27 spindle of 50 to 25,000 mPa·s at 177° C.

In a preferred embodiment of the invention the DCPD polymer comprises olefinic unsaturation, e.g., at least 1 mol % olefinic hydrogen, based on the total moles of hydrogen in the interpolymer as determined by $^1$H-NMR. In another embodiment, the DCPD polymer comprises from 1 to 20 mol % aromatic hydrogen, or preferably from 2 to 15 mol % aromatic hydrogen, or more preferably from 2 to 10 mol % aromatic hydrogen, preferably at least 8 mol % aromatic hydrogen, based on the total moles of hydrogen in the polymer.

In a preferred embodiment of the invention, the DCPD polymer is the polymer described in WO 2012/050658 A1.

This invention also relates to a composition comprising one or more of the formulae:

(I)

(II)

(III)

(IV)

wherein, optionally, one or more positions on the polymeric backbone can be substituted with an aromatic group;

each X is, independently, —$CO_2R$, —$CONR_1R_2$, CN, a $C_1$ to a $C_{20}$ alkyl group or, the residual terminal portion of a vinyl terminated macromonomer (VTM) with the provisio that, if a VTM is present, the residual terminal portion of a VTM is for formulae (I) and (II);

wherein,

R is a $C_1$ to a $C_{20}$ alkyl group or an aromatic group;

each $R_1$ and $R_2$ is, independently, a hydrogen, a $C_1$ to a $C_{20}$ alkyl group, or an aromatic group;

each $R_5$ is, independently, a hydrogen atom or a $C_1$ to a $C_{40}$ alkyl group;

each Ar is, independently, an aromatic group; and each n is, independently, from 0 to about 40.

In another embodiment, the present invention provides composition comprising one or more of the formulae:

(V)

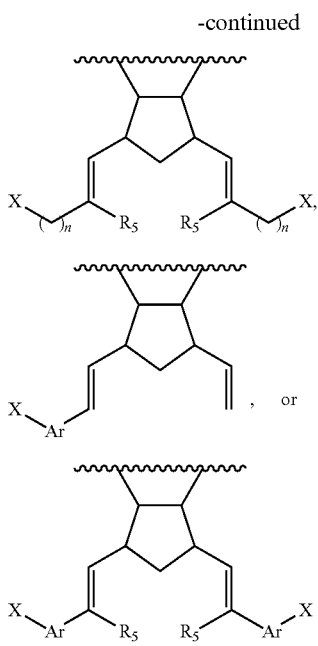

(VI)

(VII)

(VIII)

wherein,

∿∿∿∿ represents the polymeric backbone;
optionally, one or more positions on the polymeric backbone can be substituted with an aromatic group;
each X is, independently, —$CO_2R$, —$CONR_1R_2$, CN, a $C_1$ to a $C_{20}$ alkyl group or, the residual terminal portion of a vinyl terminated macromonomer (VTM) with the proviso that, if a VTM is present, the residual terminal portion of a VTM is for formulae (V) and (VI);
wherein,
R is a $C_1$ to a $C_{20}$ alkyl group or an aromatic group;
each $R_1$ and $R_2$ is, independently, a hydrogen, a $C_1$ to a $C_{20}$ alkyl group, or an aromatic group;
each $R_5$ is, independently, a hydrogen atom or a $C_1$ to a $C_{40}$ alkyl group;
each Ar is, independently, an aromatic group; and
each n is, independently, from 0 to about 40.

Process to Functionalize DCPD Monomers and Polymers

This invention relates to a process to produce functionalized DCPD polymer comprising contacting DCPD polymer and a vinyl monomer or vinylene monomer in the presence of a metathesis catalyst, where the vinyl monomer or vinylene monomer is represented by the formula:

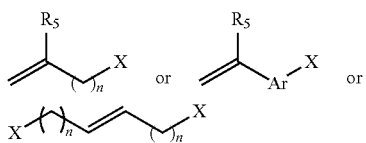

wherein
each X is, independently, —$CO_2R$, —$CONR_1R_2$, CN, a $C_1$ to a $C_{20}$ alkyl group;
R is a $C_1$ to a $C_{20}$ alkyl group or an aromatic group;
each $R_1$ and $R_2$ is, independently, a hydrogen, a $C_1$ to a $C_{20}$ alkyl group, or an aromatic group;
each $R_5$ is, independently, a hydrogen atom or a $C_1$ to a $C_{40}$ alkyl group;
each Ar is, independently, an aromatic group; and
each n is, independently, from 0 to about 40.

In an embodiment, this invention also relates to the reaction product obtained by contacting a polymer comprising units derived from dicyclopentadiene and a vinyl terminated macromonomer in the presence of a metathesis catalyst.

The reactants (including the DCPD polymer) are typically combined in a reaction vessel at a temperature of 20° C. to 200° C. (preferably 50° C. to 160° C., preferably 60° C. to 140° C.) and a pressure of 0 to 1000 MPa (preferably 0.5 to 500 MPa, preferably 1 to 250 MPa) for a residence time of 0.5 seconds to 10 hours (preferably 1 second to 5 hours, preferably 1 minute to 1 hour).

Typically, 0.00001 to 1.0 moles, preferably 0.0001 to 0.05 moles, preferably 0.0005 to 0.01 moles of catalyst are charged to the reactor per mole of DCPD polymer charged.

Typically, 0.01 to 10 moles of a vinyl monomer, VTM, or vinylene monomer, preferably 0.05 to about 5.0 moles, preferably from about 0.5 to about 2.0 moles of vinyl monomer, VTM, or vinylene monomer are charged to the reactor per mole of DCPD polymer charged.

The process is typically a solution process, although it may be a bulk or high pressure process. Homogeneous processes are preferred. (A homogeneous process is defined to be a process where at least 90 wt % of the product is soluble in the reaction media.) A bulk homogeneous process is particularly preferred. (A bulk process is defined to be a process where reactant concentration in all feeds to the reactor is 70 vol % or more.) Alternately, no solvent or diluent is present or added in the reaction medium, (except for the small amounts used as the carrier for the catalyst or other additives, or amounts typically found with the reactants; e.g., propane in propylene).

Suitable diluents/solvents for the process include non-coordinating, inert liquids. Examples include straight and branched-chain hydrocarbons, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof such as can be found commercially (Isopar™); perhalogenated hydrocarbons, such as perfluorinated $C_{4-10}$ alkanes, chlorobenzene, and aromatic and alkyl-substituted aromatic compounds such as benzene, toluene, mesitylene, and xylene. In a preferred embodiment, aliphatic hydrocarbon solvents are preferred, such as isobutane, butane, pentane, isopentane, hexanes, isohexane, heptane, octane, dodecane, and mixtures thereof; cyclic and alicyclic hydrocarbons, such as cyclohexane, cycloheptane, methylcyclohexane, methylcycloheptane, and mixtures thereof. In another embodiment, the solvent is not aromatic, preferably aromatics are present in the solvent at less than 1 wt %, preferably at 0.5 wt %, preferably at 0 wt % based upon the weight of the solvents.

In another embodiment, the process is a slurry process. As used herein the term "slurry polymerization process" means a polymerization process where a supported catalyst is employed and monomers are polymerized on the supported catalyst particles. At least 95 wt % of polymer products derived from the supported catalyst are in granular form as solid particles (not dissolved in the diluent).

In a preferred embodiment, the feed concentration for the process is 60 vol % solvent or less, preferably 40 vol % or less, preferably 20 vol % or less.

The process may be batch, semi-batch or continuous. As used herein, the term continuous means a system that operates without interruption or cessation. For example, a continuous process to produce a polymer would be one where the reactants are continually introduced into one or more reactors and polymer product is continually withdrawn.

Useful reaction vessels include reactors (including continuous stirred tank reactors, batch reactors, reactive extruder, pipe or pump).

In a preferred embodiment, the productivity of the process is at least 200 g of DCPD polymer per mmol of catalyst per hour, preferably at least 5,000 g/mmol/hour, preferably at least 10,000 g/mmol/hr, preferably at least 300,000 g/mmol/ hr.

This invention further relates to a process, preferably an in-line process, preferably a continuous process, to produce functionalized DCPD polymers, comprising introducing a DCPD into a reactor and heating the DCPD to polymerize it, obtaining a reactor effluent containing DCPD polymers, optionally removing (such as flashing off) solvent, unused monomer and/or other volatiles, obtaining DCPD polymers, introducing DCPD polymers, vinyl, vinylene or VTM monomer and a metathesis catalyst into a reaction zone (such as a reactor, an extruder, a pipe and/or a pump), obtaining a reactor effluent containing functionalized DCPD polymers, optionally removing (such as flashing off) solvent, unused monomer and/or other volatiles, (such as those described herein), and obtaining functionalized DCPD polymers (such as those described herein).

A "reaction zone" also referred to as a "polymerization zone" is defined as an area where activated catalysts and monomers are contacted and a polymerization reaction takes place. When multiple reactors are used in either series or parallel configuration, each reactor is considered as a separate polymerization zone. For a multi-stage polymerization in both a batch reactor and a continuous reactor, each polymerization stage is considered as a separate polymerization zone.

Vinyl Terminated Macromonomer

A "vinyl terminated macromonomer," as used herein, refers to one or more of:

(i) a vinyl terminated polymer having at least 5% allyl chain ends (preferably 15%, 20%, 30%, 40%, 50%, 60%, 70%, 80%, 90%, 95%, 98%, or 99%);

(ii) a vinyl terminated polymer having an Mn of at least 160 g/mol, preferably at least 200 g/mol (measured by $^1$H NMR) comprising of one or more $C_4$ to $C_{40}$ higher olefin derived units, where the higher olefin polymer comprises substantially no propylene derived units; and wherein the higher olefin polymer has at least 5% allyl chain ends;

(iii) a copolymer having an Mn of 300 g/mol or more (measured by $^1$H NMR) comprising (a) from about 20 mol % to about 99.9 mol % of at least one $C_5$ to $C_{40}$ higher olefin, and (b) from about 0.1 mol % to about 80 mol % of propylene, wherein the higher olefin copolymer has at least 40% allyl chain ends;

(iv) a copolymer having an Mn of 300 g/mol or more (measured by $^1$H NMR), and comprises (a) from about 80 mol % to about 99.9 mol % of at least one $C_4$ olefin, (b) from about 0.1 mol % to about 20 mol % of propylene; and wherein the vinyl terminated macromonomer has at least 40% allyl chain ends relative to total unsaturation;

(v) a co-oligomer having an Mn of 300 g/mol to 30,000 g/mol (measured by $^1$H NMR) comprising 10 mol % to 90 mol % propylene and 10 mol % to 90 mol % of ethylene, wherein the oligomer has at least X % allyl chain ends (relative to total unsaturations), where: 1) X=(-0.94*(mol % ethylene incorporated)+100), when 10 mol % to 60 mol % ethylene is present in the co-oligomer, 2) X=45, when greater than 60 mol % and less than 70 mol % ethylene is present in the co-oligomer, and 3) X=(1.83*(mol % ethylene incorporated)-83), when 70 mol % to 90 mol % ethylene is present in the co-oligomer;

(vi) a propylene oligomer, comprising more than 90 mol % propylene and less than 10 mol % ethylene wherein the oligomer has: at least 93% allyl chain ends, a number average molecular weight (Mn) of about 500 g/mol to about 20,000 g/mol, an isobutyl chain end to allylic vinyl group ratio of 0.8:1 to 1.35:1.0, less than 100 ppm aluminum, and/or less than 250 regio defects per 10,000 monomer units;

(vii) a propylene oligomer, comprising: at least 50 mol % propylene and from 10 mol % to 50 mol % ethylene, wherein the oligomer has: at least 90% allyl chain ends, an Mn of about 150 g/mol to about 20,000 g/mol, preferably 10,000 g/mol, and an isobutyl chain end to allylic vinyl group ratio of 0.8:1 to 1.2:1.0, wherein monomers having four or more carbon atoms are present at from 0 mol % to 3 mol %;

(viii) a propylene oligomer, comprising: at least 50 mol % propylene, from 0.1 mol % to 45 mol % ethylene, and from 0.1 mol % to 5 mol % $C_4$ to $C_{12}$ olefin, wherein the oligomer has: at least 90% allyl chain ends, an Mn of about 150 g/mol to about 10,000 g/mol, and an isobutyl chain end to allylic vinyl group ratio of 0.8:1 to 1.35:1.0;

(ix) a propylene oligomer, comprising: at least 50 mol % propylene, from 0.1 mol % to 45 mol % ethylene, and from 0.1 mol % to 5 mol % diene, wherein the oligomer has: at least 90% allyl chain ends, an Mn of about 150 g/mol to about 10,000 g/mol, and an isobutyl chain end to allylic vinyl group ratio of 0.7:1 to 1.35:1.0;

(x) a homo-oligomer, comprising propylene, wherein the oligomer has: at least 93% allyl chain ends, an Mn of about 500 g/mol to about 70,000 g/mol, alternately to about 20,000 g/mol, an isobutyl chain end to allylic vinyl group ratio of 0.8:1 to 1.2:1.0, and less than 1400 ppm aluminum;

(xi) vinyl terminated polyethylene having: (a) at least 60% allyl chain ends; (b) a molecular weight distribution of less than or equal to 4.0; (c) a $g'_{(vis)}$ of greater than 0.95; and (d) an Mn ($^1$H NMR) of at least 20,000 g/mol; and (xii) vinyl terminated polyethylene having: (a) at least 50% allyl chain ends; (b) a molecular weight distribution of less than or equal to 4.0; (c) a $g'_{(vis)}$ of 0.95 or less; (d) an Mn ($^1$H NMR) of at least 7,000 g/mol; and (e) a Mn (GPC)/Mn ($^1$H NMR) in the range of from about 0.8 to about 1.2.

It is understood by those of ordinary skill in the art that when the VTM's, as described here, are reacted with another material the "vinyl" (e.g. the allyl chain end) is involved in the reaction and has been transformed. Thus, the language used herein describing that a fragment of the final product (typically referred to as PO in the formulae herein) is the residual portion of a vinyl terminated macromonomer (VTM) having had a terminal unsaturated carbon of an allylic chain and a vinyl carbon adjacent to the terminal unsaturated carbon, is meant to refer to the fact that the VTM has been incorporated in the product. Similarly stating that a product or material comprises a VTM means that the reacted form of the VTM is present, unless the context clearly indicates otherwise (such as a mixture of ingredients that do not have a catalytic agent present.)

In some embodiments, the vinyl terminated macromonomer has an Mn of at least 200 g/mol, (e.g., 200 g/mol to 100,000 g/mol, e.g., 200 g/mol to 75,000 g/mol, e.g., 200 g/mol to 60,000 g/mol, e.g., 300 g/mol to 60,000 g/mol, or e.g., 750 g/mol to 30,000 g/mol) (measured by $^1$H NMR) and comprises one or more (e.g., two or more, three or more, four or more, and the like) $C_4$ to $C_{40}$ (e.g., $C_4$ to $C_{30}$, $C_4$ to $C_{20}$, or $C_4$ to $C_{12}$, e.g., butene, pentene, hexene, heptene, octene, nonene, decene, undecene, dodecene, norbornene, norbornadiene, dicyclopentadiene, cyclopentene, cycloheptene, cyclooctene, cyclooctadiene, cyclododecene, 7-oxanorbornene, 7-oxanorbornadiene, substituted derivatives thereof, and isomers thereof) olefin derived units, where the vinyl terminated macromonomer comprises substantially no propylene derived units (e.g., less than 0.1 wt % propylene, e.g., 0 wt %); and wherein the vinyl terminated macromonomer has at least 5% (at least 10%, at least 15%, at least 20%, at least 30%, at least 40%, at least 50%, at least 60%, at least 70%; at least 80%, at least 90%, or at least 95%) allyl chain ends (relative to total unsaturation); and optionally, an allyl chain end to vinylidene chain end ratio of 1:1 or greater (e.g., greater than 2:1, greater than 2.5:1, greater than 3:1, greater than 5:1, or greater than 10:1); and even further optionally, e.g., substantially no isobutyl chain ends (e.g., less than 0.1 wt % isobutyl chain ends). In some embodiments, the vinyl terminated macromonomers may also comprise ethylene derived units, e.g., at least 5 mol % ethylene (e.g., at least 15 mol % ethylene, e.g., at least 25 mol % ethylene, e.g., at least 35 mol % ethylene, e.g., at least 45 mol % ethylene, e.g., at least 60 mol % ethylene, e.g., at least 75 mol % ethylene, or e.g., at least 90 mol % ethylene). Such vinyl terminated macromonomers are further described in U.S. Pat. No. 8,426,659, which is hereby incorporated by reference.

In some embodiments, the vinyl terminated macromonomers may have an Mn (measured by $^1$H NMR) of greater than 200 g/mol (e.g., 300 g/mol to 60,000 g/mol, 400 g/mol to 50,000 g/mol, 500 g/mol to 35,000 g/mol, 300 g/mol to 15,000 g/mol, 400 g/mol to 12,000 g/mol, or 750 g/mol to 10,000 g/mol), and comprise:
(a) from about 20 mol % to 99.9 mol % (e.g., from about 25 mol % to about 90 mol %, from about 30 mol % to about 85 mol %, from about 35 mol % to about 80 mol %, from about 40 mol % to about 75 mol %, or from about 50 mol % to about 95 mol %) of at least one $C_5$ to $C_{40}$ (e.g., $C_6$ to $C_{20}$) higher olefin;
(b) from about 0.1 mol % to 80 mol % (e.g., from about 5 mol % to 70 mol %, from about 10 mol % to about 65 mol %, from about 15 mol % to about 55 mol %, from about 25 mol % to about 50 mol %, or from about 30 mol % to about 80 mol %) of propylene; and wherein the vinyl terminated macromonomer has at least 40% allyl chain ends (e.g., at least 50% allyl chain ends, at least 60% allyl chain ends, at least 70% allyl chain ends, or at least 80% allyl chain ends, at least 90% allyl chain ends, at least 95% allyl chain ends) relative to total unsaturation; and, optionally, an isobutyl chain end to allyl chain end ratio of less than 0.70:1, less than 0.65:1, less than 0.60:1, less than 0.50:1, or less than 0.25:1; and further optionally, an allyl chain end to vinylidene chain end ratio of greater than 2:1 (e.g., greater than 2.5:1, greater than 3:1, greater than 5:1, or greater than 10:1); and even further optionally, an allyl chain end to vinylene ratio is greater than 1:1 (e.g., greater than 2:1 or greater than 5:1). Such macromonomers are further described in U.S. Pat. No. 8,399,724, hereby incorporated by reference.

In another embodiment, the vinyl terminated macromonomer has an Mn of 300 g/mol or more (measured by $^1$H NMR, e.g., 300 g/mol to 60,000 g/mol, 400 g/mol to 50,000 g/mol, 500 g/mol to 35,000 g/mol, 300 g/mol to 15,000 g/mol, 400 g/mol to 12,000 g/mol, or 750 g/mol to 10,000 g/mol), and comprises:
(a) from about 80 mol % to about 99.9 mol % of at least one $C_4$ olefin, e.g., about 85 mol % to about 99.9 mol %, e.g., about 90 mol % to about 99.9 mol %;
(b) from about 0.1 mol % to about 20 mol % of propylene, e.g., about 0.1 mol % to about 15 mol %, e.g., about 0.1 mol % to about 10 mol %; and wherein the vinyl terminated macromonomer has at least 40% allyl chain ends (e.g., at least 50% allyl chain ends, at least 60% allyl chain ends, at least 70% allyl chain ends, or at least 80% allyl chain ends, at least 90% allyl chain ends, at least 95% allyl chain ends) relative to total unsaturation, and in some embodiments, an isobutyl chain end to allyl chain end ratio of less than 0.70:1, less than 0.65:1, less than 0.60:1, less than 0.50:1, or less than 0.25:1, and in further embodiments, an allyl chain end to vinylidene group ratio of more than 2:1, more than 2.5:1, more than 3:1, more than 5:1, or more than 10:1. Such macromonomers are also further described in U.S. Pat. No. 8,399,724, which is hereby incorporated by reference.

In other embodiments, the vinyl terminated macromonomer is a propylene co-oligomer having an Mn of 300 g/mol to 30,000 g/mol as measured by $^1$H NMR (e.g., 400 g/mol to 20,000 g/mol, e.g., 500 g/mol to 15,000 g/mol, e.g., 600 g/mol to 12,000 g/mol, e.g., 800 g/mol to 10,000 g/mol, e.g., 900 g/mol to 8,000 g/mol, e.g., 900 g/mol to 7,000 g/mol), comprising 10 mol % to 90 mol % propylene (e.g., 15 mol % to 85 mol %, e.g., 20 mol % to 80 mol %, e.g., 30 mol % to 75 mol %, e.g., 50 mol % to 90 mol %) and 10 mol % to 90 mol % (e.g., 85 mol % to 15 mol %, e.g., 20 mol % to 80 mol %, e.g., 25 mol % to 70 mol %, e.g., 10 mol % to 50 mol %) of one or more alpha-olefin comonomers (e.g., ethylene, butene, hexene, or octene, e.g., ethylene), wherein the oligomer has at least X % allyl chain ends (relative to total unsaturations), where: 1) X=(−0.94 (mol % ethylene incorporated)+100 {alternately 1.20 (−0.94 (mol % ethylene incorporated)+ 100), alternately 1.50(−0.94 (mol % ethylene incorporated)+ 100)}), when 10 mol % to 60 mol % ethylene is present in the co-oligomer; 2) X=45 (alternately 50, alternately 60), when greater than 60 mol % and less than 70 mol % ethylene is present in the co-oligomer; and 3) X=(1.83*(mol % ethylene incorporated)−83, {alternately 1.20 [1.83*(mol % ethylene incorporated)−83], alternately 1.50 [1.83*(mol % ethylene incorporated)−83]}), when 70 mol % to 90 mol % ethylene is present in the co-oligomer. Such macromonomers are further described in U.S. Pat. No. 8,372,930, which is hereby incorporated by reference.

In other embodiments, the vinyl terminated macromonomer is a propylene oligomer, comprising more than 90 mol % propylene (e.g., 95 mol % to 99 mol %, e.g., 98 mol % to 9 mol %) and less than 10 mol % ethylene (e.g., 1 mol % to 4 mol %, e.g., 1 mol % to 2 mol %), wherein the oligomer has: at least 93% allyl chain ends (e.g., at least 95%, e.g., at least 97%, e.g., at least 98%); a number average molecular weight (Mn) of about 400 g/mol to about 30,000 g/mol, as measured by $^1$H NMR (e.g., 500 g/mol to 20,000 g/mol, e.g., 600 g/mol to 15,000 g/mol, e.g., 700 g/mol to 10,000 g/mol, e.g., 800 g/mol to 9,000 g/mol, e.g., 900 g/mol to 8,000 g/mol, e.g., 1,000 g/mol to 6,000 g/mol); an isobutyl chain end to allylic vinyl group ratio of 0.8:1 to 1.35:1.0, and less than 1400 ppm aluminum, (e.g., less than 1200 ppm, e.g., less than 1000 ppm, e.g., less than 500 ppm, e.g., less than 100 ppm). Such macromonomers are further described in U.S. Pat. No. 8,372,930.

In other embodiments, the vinyl terminated macromonomer is a propylene oligomer, comprising: at least 50 mol % (e.g., 60 mol % to 90 mol %, e.g., 70 mol % to 90 mol %) propylene and from 10 mol % to 50 mol % (e.g., 10 mol % to 40 mol %, e.g., 10 mol % to 30 mol %) ethylene, wherein the oligomer has: at least 90% allyl chain ends (e.g., at least 91%, e.g., at least 93%, e.g., at least 95%, e.g., at least 98%); an Mn of about 150 g/mol to about 20,000 g/mol, as measured by $^1$H NMR (e.g., 200 g/mol to 15,000 g/mol, e.g., 250 g/mol to 15,000 g/mol, e.g., 300 g/mol to 10,000 g/mol, e.g., 400 g/mol to 9,500 g/mol, e.g., 500 g/mol to 9,000 g/mol, e.g., 750 g/mol to 9,000 g/mol); and an isobutyl chain end to allylic vinyl group ratio of 0.8:1 to 1.3:1.0, wherein monomers having four or more carbon atoms are present at from 0 mol % to 3 mol %

(e.g., at less than 1 mol %, e.g., less than 0.5 mol %, e.g., at 0 mol %). Such macromonomers are further described in U.S. Pat. No. 8,372,930.

In other embodiments, the vinyl terminated macromonomer is a propylene oligomer, comprising: at least 50 mol % (e.g., at least 60 mol %, e.g., 70 mol % to 99.5 mol %, e.g., 80 mol % to 99 mol %, e.g., 90 mol % to 98.5 mol %) propylene, from 0.1 mol % to 45 mol % (e.g., at least 35 mol %, e.g., 0.5 mol % to 30 mol %, e.g., 1 mol % to 20 mol %, e.g., 1.5 mol % to 10 mol %) ethylene, and from 0.1 mol % to 5 mol % (e.g., 0.5 mol % to 3 mol %, e.g., 0.5 mol % to 1 mol %) $C_4$ to $C_{12}$ olefin (such as butene, hexene, or octene, e.g., butene), wherein the oligomer has: at least 90% allyl chain ends (e.g., at least 91%, e.g., at least 93%, e.g., at least 95%, e.g., at least 98%); a number average molecular weight (Mn) of about 150 g/mol to about 15,000 g/mol, as measured by $^1$H NMR (e.g., 200 g/mol to 12,000 g/mol, e.g., 250 g/mol to 10,000 g/mol, e.g., 300 g/mol to 10,000 g/mol, e.g., 400 g/mol to 9500 g/mol, e.g., 500 g/mol to 9,000 g/mol, e.g., 750 g/mol to 9,000 g/mol); and an isobutyl chain end to allylic vinyl group ratio of 0.8:1 to 1.35:1.0. Such macromonomers are further described in U.S. Pat. No. 8,372,930.

In other embodiments, the vinyl terminated macromonomer is a propylene oligomer, comprising: at least 50 mol % (e.g., at least 60 mol %, e.g., 70 mol % to 99.5 mol %, e.g., 80 mol % to 99 mol %, e.g., 90 mol % to 98.5 mol %) propylene, from 0.1 mol % to 45 mol % (e.g., at least 35 mol %, e.g., 0.5 mol % to 30 mol %, e.g., 1 mol % to 20 mol %, e.g., 1.5 mol % to 10 mol %) ethylene, and from 0.1 mol % to 5 mol % (e.g., 0.5 mol % to 3 mol %, e.g., 0.5 mol % to 1 mol %) diene (such as $C_4$ to $C_{12}$ alpha-omega dienes (such as butadiene, hexadiene, octadiene), norbornene, ethylidene norbornene, vinylnorbornene, norbornadiene, and dicyclopentadiene), wherein the oligomer has at least 90% allyl chain ends (e.g., at least 91%, e.g., at least 93%, e.g., at least 95%, e.g., at least 98%); a number average molecular weight (Mn) of about 150 g/mol to about 20,000 g/mol, as measured by $^1$H NMR (e.g., 200 g/mol to 15,000 g/mol, e.g., 250 g/mol to 12,000 g/mol, e.g., 300 g/mol to 10,000 g/mol, e.g., 400 g/mol to 9,500 g/mol, e.g., 500 g/mol to 9,000 g/mol, e.g., 750 g/mol to 9,000 g/mol); and an isobutyl chain end to allylic vinyl group ratio of 0.7:1 to 1.35:1.0. Such macromonomers are further described in U.S. Pat. No. 8,372,930.

In other embodiments, the vinyl terminated macromonomer is a propylene homo-oligomer, comprising propylene and less than 0.5 wt % comonomer, e.g., 0 wt % comonomer, wherein the oligomer has:
i) at least 93% allyl chain ends (e.g., at least 95%, e.g., at least 96%, e.g., at least 97%, e.g., at least 98%, e.g., at least 99%);
ii) a number average molecular weight (Mn) of about 500 g/mol to about 20,000 g/mol, as measured by $^1$H NMR (e.g., 500 g/mol to 15,000 g/mol, e.g., 700 g/mol to 10,000 g/mol, e.g., 800 g/mol to 8,000 g/mol, e.g., 900 g/mol to 7,000 g/mol, e.g., 1,000 g/mol to 6,000 g/mol, e.g., 1,000 g/mol to 5,000 g/mol);
iii) an isobutyl chain end to allylic vinyl group ratio of 0.8:1 to 1.3:1.0; and
iv) less than 1400 ppm aluminum, (e.g., less than 1200 ppm, e.g., less than 1000 ppm, e.g., less than 500 ppm, e.g., less than 100 ppm). Such macromonomers are also further described in U.S. Pat. No. 8,372,930.

The vinyl terminated macromonomers may be homopolymers, copolymers, terpolymers, and so on. Any vinyl terminated macromonomers described herein has one or more of:
(i) an isobutyl chain end to allylic vinyl group ratio of 0.8:1 to 1.3:1.0;
(ii) an allyl chain end to vinylidene chain end ratio of greater than 2:1 (e.g., greater than 2.5:1, greater than 3:1, greater than 5:1, or greater than 10:1);
(iii) an allyl chain end to vinylene ratio is greater than 1:1 (e.g., greater than 2:1 or greater than 5:1); and
(iv) at least 5% allyl chain ends (preferably 15%, 20%, 30%, 40%, 50%, 60%, 70%, 80%, 90%, 95%, 98%, or 99%).

Vinyl terminated macromonomers generally have a saturated chain end (or terminus) and/or an unsaturated chain end or terminus. The unsaturated chain end of the vinyl terminated macromonomer comprises an "allyl chain end" or a "3-alkyl" chain end.

An allyl chain end is represented by $CH_2CH—CH_2—$, as shown in the formula:

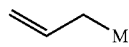

where M represents the polymer chain. "Allylic vinyl group," "allyl chain end," "vinyl chain end," "vinyl termination," "allylic vinyl group," and "vinyl terminated" are used interchangeably in the following description. The number of allyl chain ends, vinylidene chain ends, vinylene chain ends, and other unsaturated chain ends is determined using $^1$H NMR at 120° C. using deuterated tetrachloroethane as the solvent on an at least 250 MHz NMR spectrometer, and in selected cases, confirmed by $^{13}$C NMR. Resconi has reported proton and carbon assignments (neat perdeuterated tetrachloroethane used for proton spectra, while a 50:50 mixture of normal and perdeuterated tetrachloroethane was used for carbon spectra; all spectra were recorded at 100° C. on a BRUKER spectrometer operating at 500 MHz for proton and 125 MHz for carbon) for vinyl terminated oligomers in *J. American Chemical Soc.*, 114, 1992, pp. 1025-1032 that are useful herein. Allyl chain ends are reported as a molar percentage of the total number of moles of unsaturated groups (that is, the sum of allyl chain ends, vinylidene chain ends, vinylene chain ends, and the like).

A 3-alkyl chain end (where the alkyl is a $C_1$ to $C_{38}$ alkyl), also referred to as a "3-alkyl vinyl end group" or a "3-alkyl vinyl termination," is represented by the formula:

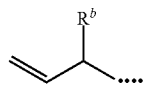

3-alkyl vinyl end group
where "••••" represents the polyolefin chain and $R^b$ is a $C_1$ to $C_{38}$ alkyl group, or a $C_1$ to $C_{20}$ alkyl group, such as methyl, ethyl, propyl, butyl, pentyl, hexyl, heptyl, octyl, nonyl, decyl, undecyl, dodecyl, and the like. The amount of 3-alkyl chain ends is determined using $^{13}$C NMR as set out below.

$^{13}$C NMR data is collected at 120° C. at a frequency of at least 100 MHz, using a BRUKER 400 MHz NMR spectrometer. A 90 degree pulse, an acquisition time adjusted to give a digital resolution between 0.1 and 0.12 Hz, at least a 10 second pulse acquisition delay time with continuous broadband proton decoupling using swept square wave modulation without gating is employed during the entire acquisition period. The spectra is acquired with time averaging to provide a signal to noise level adequate to measure the signals of interest. Samples are dissolved in tetrachloroethane-$d_2$ at concentrations between 10 wt % to 15 wt % prior to being inserted into the spectrometer magnet. Prior to data analysis spectra are referenced by setting the chemical shift of the TCE solvent signal to 74.39 ppm. Chain ends for quantization were identified using the signals shown in the table below. N-butyl and n-propyl were not reported due to their low abundance (less than 5%) relative to the chain ends shown in the table below.

| Chain End | $^{13}$C NMR Chemical Shift |
|---|---|
| P~i-Bu | 23-5 to 25.5 and 25.8 to 26.3 ppm |
| E~i-Bu | 39.5 to 40.2 ppm |
| P~Vinyl | 41.5 to 43 ppm |
| E~Vinyl | 33.9 to 34.4 ppm |

The "allyl chain end to vinylidene chain end ratio" is defined to be the ratio of the percentage of allyl chain ends to the percentage of vinylidene chain ends. The "allyl chain end to vinylene chain end ratio" is defined to be the ratio of the percentage of allyl chain ends to the percentage of vinylene chain ends. Vinyl terminated macromonomers typically also have a saturated chain end. In polymerizations where propylene is present, the polymer chain may initiate growth in a propylene monomer, thereby generating an isobutyl chain end. An "isobutyl chain end" is defined to be an end or terminus of a polymer, represented as shown in the formula below:

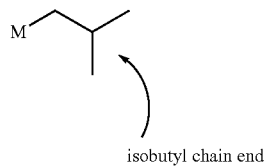

isobutyl chain end where M represents the polymer chain. Isobutyl chain ends are determined according to the procedure set out in WO 2009/155471. The "isobutyl chain end to allylic vinyl group ratio" is defined to be the ratio of the percentage of isobutyl chain ends to the percentage of allyl chain ends. The "isobutyl chain end to alpha bromo carbon ratio" is defined to be the ratio of the percentage of isobutyl chain ends to the percentage of brominated chain ends (at about 34 ppm).

In polymerizations comprising $C_4$ or greater monomers (or "higher olefin" monomers), the saturated chain end may be a $C_4$ or greater (or "higher olefin") chain end, as shown in the formula below:

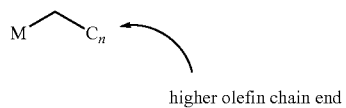

higher olefin chain end where M represents the polymer chain and n is an integer selected from 4 to 40. This is especially true when there is substantially no ethylene or propylene in the polymerization. In an ethylene/($C_4$ or greater monomer) copolymerization, the polymer chain may initiate growth in an ethylene monomer, thereby generating a saturated chain end which is an ethyl chain end.

Mn ($^1$H NMR) is determined according to the following NMR method. $^1$H NMR data is collected at either 25° C. or 120° C. (for purposes of the claims, 120° C. shall be used) in a 5 mm probe using a Varian spectrometer with a $^1$H frequency of 250 MHz, 400 MHz, or 500 MHz (for the purpose of the claims, a proton frequency of 400 MHz is used). Data are recorded using a maximum pulse width of 45°, 8 seconds between pulses and signal averaging 120 transients. Spectral signals are integrated and the number of unsaturation types per 1000 carbons is calculated by multiplying the different groups by 1000 and dividing the result by the total number of carbons. Mn is calculated by dividing the total number of unsaturated species into 14,000, and has units of g/mol. The chemical shift regions for the olefin types are defined to be between the following spectral regions.

| Unsaturation Type | Region (ppm) | Number of hydrogens per structure |
|---|---|---|
| Vinyl | 4.95-5.10 | 2 |
| Vinylidene (VYD) | 4.70-4.84 | 2 |
| Vinylene | 5.31-5.55 | 2 |
| Trisubstituted | 5.11-5.30 | 1 |

Unless otherwise stated, Mn (GPC) is determined using the GPC-DRI method described below; however, Nota Bene: for the purpose of the claims, Mn is determined by $^1$H NMR. Mn, Mw, and Mz may be measured by using a Gel Permeation Chromatography (GPC) method using a High Temperature Size Exclusion Chromatograph (SEC, either from Waters Corporation or Polymer Laboratories), equipped with a differential refractive index detector (DRI). Molecular weight distribution (MWD) is Mw (GPC)/Mn (GPC). Experimental details, are described in: T. Sun, P. Brant, R. R. Chance, and W. W. Graessley, *Macromolecules*, Volume 34, Number 19, pp. 6812-6820, (2001) and references therein. Three Polymer Laboratories PLgel 10 mm Mixed-B columns are used. The nominal flow rate is 0.5 cm$^3$/min and the nominal injection volume is 300 μL. The various transfer lines, columns and differential refractometer (the DRI detector) are contained in an oven maintained at 135° C. Solvent for the SEC experiment is prepared by dissolving 6 grams of butylated hydroxy toluene as an antioxidant in 4 liters of Aldrich reagent grade 1,2,4 trichlorobenzene (TCB). The TCB mixture is then filtered through a 0.7 μm glass pre-filter and subsequently through a 0.1 μm Teflon filter. The TCB is then degassed with an online degasser before entering the SEC. Polymer solutions are prepared by placing dry polymer in a glass container, adding the desired amount of TCB, then heating the mixture at 160° C. with continuous agitation for about 2 hours. All quantities are measured gravimetrically. The TCB densities used to express the polymer concentration in mass/volume units are 1.463 g/mL at 25° C. and 1.324 g/mL at 135° C. The injection concentration is from 1.0 to 2.0 mg/mL, with lower concentrations being used for higher molecular weight samples. Prior to running each sample the DRI detector and the injector are purged. Flow rate in the apparatus is then increased to 0.5 mL/minute, and the DRI is allowed to stabilize for 8 to 9 hours before injecting the first sample. The concentration, c, at each point in the chromatogram is calculated from the baseline-subtracted DRI signal, $I_{DRI}$, using the following equation:

$$c = K_{DRI} I_{DRI}/(dn/dc)$$

where $K_{DRI}$ is a constant determined by calibrating the DRI, and (dn/dc) is the refractive index increment for the system. The refractive index, n=1.500 for TCB at 135° C. and λ=690 nm. For purposes of this invention and the claims thereto, (dn/dc)=0.104 for propylene polymers and ethylene polymers, and 0.1 otherwise. Units of parameters used throughout this description of the SEC method are: concentration is expressed in g/cm³, molecular weight is expressed in g/mol, and intrinsic viscosity is expressed in dL/g.

The branching index ($g'_{(vis)}$) is calculated using the output of the SEC-DRI-LS-VIS method as follows. The average intrinsic viscosity, $[\eta]_{avg}$, of the sample is calculated by:

$$[\eta]_{avg} = \frac{\sum c_i [\eta]_i}{\sum c_i}$$

where the summations are over the chromatographic slices, i, between the integration limits.

The branching index g'(vis) is defined as:

$$g'vis = \frac{[\eta]_{avg}}{kM_v^\alpha}$$

where, for purpose of this invention and claims thereto, α=0.695 and k=0.000579 for linear ethylene polymers, α=0.705 and k=0.000262 for linear propylene polymers, and α=0.695 and k=0.000181 for linear butene polymers. $M_V$ is the viscosity-average molecular weight based on molecular weights determined by LS analysis. See Macromolecules, 2001, 34, pp. 6812-6820 and Macromolecules, 2005, 38, pp. 7181-7183, for guidance on selecting a linear standard having similar molecular weight and comonomer content, and determining k coefficients and α exponents.

In an embodiment, the polyolefin is derived from a vinyl terminated propylene polymer. In an embodiment, the vinyl terminated propylene polymer is produced using a process comprising: contacting propylene, under polymerization conditions, with a catalyst system comprising an activator and at least one metallocene compound represented by the formula:

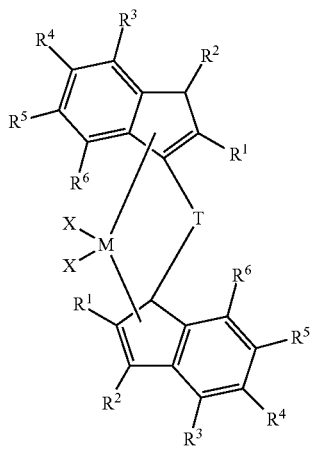

where:
M is hafnium or zirconium;
each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system);
each $R^1$ is, independently, a $C_1$ to $C_{10}$ alkyl group;
each $R^2$ is, independently, a $C_1$ to $C_{10}$ alkyl group;
each $R^3$ is hydrogen;
each $R^4$, $R^5$, and $R^6$, is, independently, hydrogen or a substituted hydrocarbyl or unsubstituted hydrocarbyl group, or a heteroatom;
T is a bridging group;
further provided that any of adjacent $R^4$, $R^5$, and $R^6$ groups may form a fused ring or multicenter fused ring system where the rings may be aromatic, partially saturated or saturated; and
obtaining a propylene polymer having at least 50% allyl chain ends (relative to total unsaturations), as described in U.S. Pat. No. 8,455,597, which is incorporated by reference in its entirety herein.

In an embodiment, the vinyl terminated propylene polymer is produced using a process comprising:
1) contacting:
a) one or more olefins with
b) a transition metal catalyst compound represented by the formula:

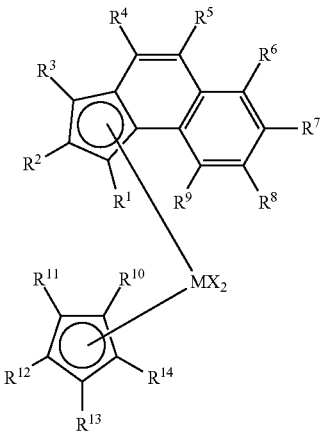

wherein
M is hafnium or zirconium;
each X is, independently, selected from the group consisting of hydrocarbyl radicals having from 1 to 20 carbon atoms, hydrides, amides, alkoxides, sulfides, phosphides, halogens, dienes, amines, phosphines, ethers, or a combination thereof;
each $R^1$ and $R^3$ are, independently, a $C_1$ to $C_8$ alkyl group; and
each $R^2$, $R^4$, $R^5$, $R^6$, $R^7$, $R^8$, $R^9$, $R^{10}$, $R^{11}$, $R^{12}$, $R^{13}$, and $R^{14}$ are, independently, hydrogen, or a substituted or unsubstituted hydrocarbyl group having from 1 to 8 carbon atoms, provided however that at least three of the $R^{10}$-$R^{14}$ groups are not hydrogen; and
2) obtaining vinyl terminated polymer having an Mn of 300 g/mol or more and at least 30% allyl chain ends (relative to total unsaturation), as described in U.S. Pat. No. 8,318,998, which is incorporated by reference in its entirety herein.

In an embodiment, the polyolefin chain is derived from a higher olefin copolymer comprising allyl chain ends. In an embodiment, the higher olefin copolymer comprising allyl chain ends has an Mn of 300 g/mol or more (measured by ¹H NMR) comprising:
(i) from about 20 mol % to about 99.9 mol % of at least one $C_5$ to $C_{40}$ higher olefin; and
(ii) from about 0.1 mol % to about 80 mol % of propylene;
wherein the higher olefin copolymer has at least 40% allyl chain ends, as described in U.S. Pat. No. 8,399,724, which is incorporated by reference in its entirety herein.

In an embodiment, the polyolefin chain is derived from a vinyl terminated branched polyolefin. In an embodiment, the vinyl terminated branched polyolefin has an Mn ($^1$H NMR) of 7,500 to 60,000 g/mol, comprising one or more alpha olefin derived units comprising ethylene and/or propylene, and having;
(i) 50% or greater allyl chain ends, relative to total number of unsaturated chain ends; and
(ii) a g'$_{vis}$ of 0.90 or less, as described in U.S. Publication No. 2012-0245299, which is incorporated by reference in its entirety herein.

In an embodiment, the polyolefin chain is derived from a vinyl terminated branched polyolefin produced by a process for polymerization, comprising:
(i) contacting, at a temperature greater than 35° C., one or more monomers comprising ethylene and/or propylene, with a catalyst system comprising a metallocene catalyst compound and an activator, wherein the metallocene catalyst compound is represented by the following formula:

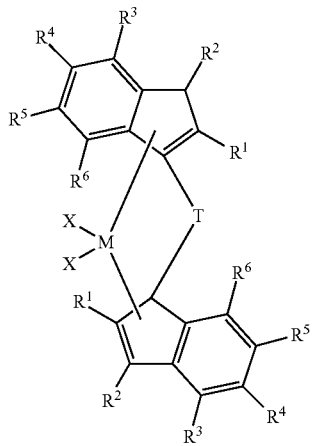

where:
M is selected from the group consisting of zirconium or hafnium;
each X is, independently, selected from the group consisting of hydrocarbyl radicals having from 1 to 20 carbon atoms, hydrides, amides, alkoxides, sulfides, phosphides, halides, dienes, amines, phosphines, ethers, and a combination thereof, (two X's may form a part of a fused ring or a ring system);
each $R^1$, $R^2$, $R^3$, $R^4$, $R^5$, and $R^6$, is, independently, hydrogen or a substituted or unsubstituted hydrocarbyl group, a heteroatom or heteroatom containing group;
further provided that any two adjacent R groups may form a fused ring or multicenter fused ring system where the rings may be aromatic, partially saturated or saturated;
further provided that any of adjacent $R^4$, $R^5$, and $R^6$ groups may form a fused ring or multicenter fused ring system where the rings may be aromatic, partially saturated or saturated;
T is a bridging group represented by the formula (Ra)$_2$J, where J is one or more of C, Si, Ge, N or P, and each Ra is, independently, hydrogen, halogen, $C_1$ to $C_{20}$ hydrocarbyl or a $C_1$ to $C_{20}$ substituted hydrocarbyl, provided that at least one $R^3$ is a substituted or unsubstituted phenyl group, if any of $R^1$, $R^2$, $R^4$, $R^5$, or $R^6$ are not hydrogen;
(ii) converting at least 50 mol % of the monomer to polyolefin; and
(iii) obtaining a branched polyolefin having greater than 50% allyl chain ends, relative to total unsaturated chain ends and a Tm of 60° C. or more, as described in U.S. Publication No. 2012-0245299, which is incorporated by reference in its entirety herein.

In an embodiment of the invention, the polyolefin is derived from a vinyl terminated ethylene polymer, preferably a vinyl terminated polyethylene (preferably in particulate form) having:
(a) at least 60% allyl chain ends (preferably at least 65%, preferably at least 70%, preferably at least 75%, preferably at least 80%, preferably at least 85%, preferably at least 90%, preferably at least 95%, preferably at least 96%, preferably at least 97%, preferably at least 98%, preferably at least 99%, or preferably at least 100%);
(b) a molecular weight distribution of less than or equal to 4.0 (preferably less than or equal to 3.8, preferably less than or equal to 3.5, preferably less than or equal to 3.2, preferably less than or equal to 3.0, preferably less than or equal to 2.8, or preferably less than or equal to 2.5);
(c) an Mn ($^1$H NMR) of at least 20,000 g/mol (preferably at least 25,000 g/mol, preferably at least 30,000 g/mol, preferably at least 40,000 g/mol, preferably at least 50,000 g/mol, and, optionally, less than 125,000 g/mol, preferably less than 120,000, or preferably less than 110,000);
(d) optionally, an Mn (GPC)/Mn ($^1$H NMR) in the range of from about 0.8 to about 1.2 (preferably from about from 0.9 to about 1.1, preferably from about 0.95 to about 1.1); and
(e) optionally, a g'$_{(vis)}$ of greater than 0.95 (preferably greater than 0.96, preferably greater than 0.98, preferably greater than 0.98, and, optionally, preferably less than or equal to 1.0).

Preferably, the vinyl terminated ethylene polymers are prepared by a process comprising:
(a) contacting ethylene with a supported metallocene catalyst system;
wherein the supported catalyst system comprises: (i) a support material; (ii) an activator having from about 1 wt % to about 14 wt % trimethylaluminum, based on the weight of the activator; and (iii) a metallocene compound represented by the formula:

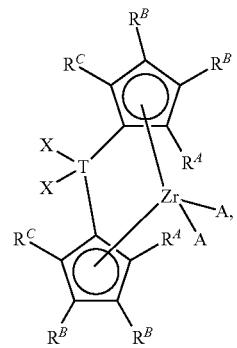

wherein: T is Si or Ge; each $R^A$ is a $C_1$ to $C_{20}$ substituted or unsubstituted hydrocarbyl group; each $R^B$ is, independently, H, or a $C_1$ to $C_8$ substituted or unsubstituted hydrocarbyl group, or a group represented by the formula —CH$_2$R$^x$; wherein R$^x$ is a $C_1$ to $C_{20}$ substituted or unsubstituted hydrocarbyl group, provided that at least one $R^B$ is methyl or a group represented by the formula —CH$_2$R$^x$; each $R^C$ is, independently, H or a $C_1$ to $C_{20}$ substituted or unsubstituted hydrocarbyl group; each A is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; each X is, independently, hydrogen, halogen or a $C_1$ to $C_{20}$ hydrocarbyl, and two X groups can form a cyclic structure including aromatic, partially saturated, or saturated cyclic or fused ring system; further provided that any of adjacent $R^A$, $R^B$, and/or $R^C$ groups may form a fused ring or multicenter fused ring systems, where the rings may be substituted or unsubstituted, and may be aromatic, partially unsaturated, or unsaturated;

(b) obtaining a vinyl terminated polyethylene having: (i) at least 60% allyl chain ends; (ii) a molecular weight distribution of less than or equal to 4.0; and (iii) a Mn ($^1$H NMR) of at least 20,000 g/mol. Preferably, the vinyl terminated ethylene polymers are made according the process (and using the catalyst systems) described in (U.S. Ser. No. 61/704,606, filed Sep. 24, 2012, entitled, Production of Vinyl Terminated Polyethylene Using Supported Catalyst System).

In an embodiment of the invention, the polyolefin is derived from a vinyl terminated ethylene polymer, preferably a vinyl terminated polyethylene having: (i) at least 50% allyl chain ends (preferably 60%, 70%, 80%, 90%, 95%, 96%, 97%, 98%, 99%, or 100%); (ii) a molecular weight distribution of less than or equal to 4.0 (preferably less than or equal to 3.8, 3.6, 3.5, 3.4, 3.2, 3.0, 2.8, or 2.5); (iii) a $g'_{(vis)}$ of 0.95 or less (preferably less than 0.93, 0.90, 0.88, or 0.85); (iv) an Mn ($^1$H NMR) of at least 7,000 g/mol (preferably at least 10,000 g/mol, 15,000 g/mol, 20,000 g/mol, 25,000 g/mol, 30,000 g/mol, 45,000 g/mol, 55,000 g/mol, 65,000 g/mol, or 85,000 g/mol, and, optionally, less than 125,000 g/mol); and (v) a Mn (GPC)/Mn ($^1$H NMR) in the range of from about 0.8 to about 1.2 (preferably from 0.85 to 1.15, 0.90 to 1.10, and 0.95 to 1.00). Preferably, the vinyl terminated ethylene polymers are produced by a process comprising:

(a) contacting ethylene with a metallocene catalyst system; wherein the catalyst system comprises:
(i) an ionizing activator;
(ii) a metallocene compound represented by the formula:

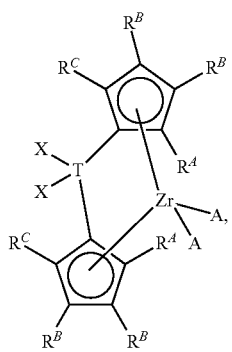

wherein T is Si or Ge; each $R^A$ is a $C_1$ to $C_{20}$ substituted or unsubstituted hydrocarbyl group; each $R^B$ is, independently, H or a $C_1$ to $C_8$ substituted or unsubstituted hydrocarbyl group, or a group represented by the formula —$CH_2R^x$; wherein $R^x$ is a $C_1$ to $C_{20}$ substituted or unsubstituted hydrocarbyl group, provided that at least one $R^B$ is methyl or a group represented by the formula —$CH_2R^x$; each $R^C$ is, independently, H or a $C_1$ to $C_{20}$ substituted or unsubstituted hydrocarbyl group; each A is independently selected from the group consisting of $C_1$ to $C_{20}$ substituted or unsubstituted hydrocarbyl groups, hydrides, amides, amines, alkoxides, sulfides, phosphides, halides, dienes, phosphines, and ethers; each X is, independently, hydrogen, halogen, or a $C_1$ to $C_{20}$ hydrocarbyl, and two X groups can form a cyclic structure including aromatic, partially saturated, or saturated cyclic or fused ring system; further provided that any of adjacent $R^A$, $R^B$, and/or $R^C$ groups may form a fused ring or multicenter fused ring systems, where the rings may be substituted or unsubstituted, and may be aromatic, partially unsaturated, or unsaturated;

(b) obtaining a vinyl terminated polyethylene having: (i) at least 50% allyl chain ends; (ii) a molecular weight distribution of less than or equal to 4.0; (iii) a $g'_{(vis)}$ of 0.95 or less; (iv) a Mn ($^1$H NMR) of at least 7,000 g/mol; and (v) a Mn (GPC)/Mn ($^1$H NMR) in the range of from about 0.8 to about 1.2. Preferably, the vinyl terminated ethylene polymers are made according the process (and using the catalyst systems) described in (U.S. Ser. No. 61/704,604, filed Sep. 24, 2012, entitled, Production of Vinyl Terminated Polyethylene).

In any of the polymerizations described herein, the activator may be an alumoxane, an aluminum alkyl, a stoichiometric activator (also referred to as an ionizing activator), which may be neutral or ionic, and/or a conventional-type cocatalyst, unless otherwise stated. Preferred activators typically include alumoxane compounds, modified alumoxane compounds, stoichiometric activators, and ionizing anion precursor compounds that abstract one reactive, 6-bound, metal ligand making the metal complex cationic and providing a charge-balancing noncoordinating or weakly coordinating anion.

Alumoxane Activators

In an embodiment of the invention, alumoxane activators are utilized as an activator in the catalyst composition, preferably methylalumoxane (MAO), modified methylalumoxane (MMAO), ethylalumoxane, and/or isobutylalumoxane. Preferably, the activator is a TMA-depleted activator (where TMA means trimethylaluminum). Any method known in the art to remove TMA may be used. For example, to produce a TMA-depleted activator, a solution of alumoxane (such as methylalumoxane), for example, 30 wt % in toluene may be diluted in toluene and the aluminum alkyl (such as TMA in the case of MAO) is removed from the solution, for example, by combination with trimethylphenol and filtration of the solid. In such embodiments, the TMA-depleted activator comprises from about 1 wt % to about 14 wt % trimethylaluminum (preferably less than 13 wt %, preferably less than 12 wt %, preferably less than 10 wt %, preferably less than 5 wt %, or preferably 0 wt %, or, optionally, greater than 0 wt % or greater than 1 wt %).

Stoichiometric Activators

The catalyst systems useful herein may comprise one or more stoichiometric activators. A stoichiometric activator is a non-alumoxane compound which when combined in a reaction with the catalyst compound (such as a metallocene compound) forms a catalytically active species, typically at molar ratios of stoichiometric activator to metallocene compound of 10:1 or less (preferably 5:1, more preferably 2:1, or even more preferably 1:1), however is within the scope of this invention to use a molar ratio of stoichiometric activator to metallocene compound of greater than 10:1 as well. Useful stoichiometric (or non-alumoxane) activator-to-catalyst ratios range from 0.5:1 to 10:1, preferably 1:1 to 5:1, although ranges of from 0.1:1 to 100:1, alternately from 0.5:1 to 200:1, alternately from 1:1 to 500:1 alternately from 1:1 to 1000:1 may be used.

Stoichiometric activators are non-alumoxane compounds which may be neutral or ionic, such as tri(n-butyl)ammonium tetrakis(pentafluorophenyl)borate, a tris perfluorophenyl boron metalloid precursor, or a tris perfluoronaphthyl boron metalloid precursor, polyhalogenated heteroborane anions (WO 98/43983), boric acid (U.S. Pat. No. 5,942,459), or a combination thereof. It is also within the scope of this invention to use stoichiometric activators alone or in combination with alumoxane or modified alumoxane activators.

Neutral Stoichiometric Activators

Examples of neutral stoichiometric activators include trisubstituted boron, tellurium, aluminum, gallium and indium or mixtures thereof. The three substituent groups are each independently selected from alkyls, alkenyls, halogens, substituted alkyls, aryls, arylhalides, alkoxy, and halides. Preferably, the three groups are independently selected from halogen, mono or multicyclic (including halosubstituted) aryls, alkyls, and alkenyl compounds, and mixtures thereof, preferred are alkenyl groups having 1 to 20 carbon atoms, alkyl groups having 1 to 20 carbon atoms, alkoxy groups having 1 to 20 carbon atoms, and aryl groups having 3 to 20 carbon atoms (including substituted aryls). More preferably, the three groups are alkyls having 1 to 4 carbon groups, phenyl, naphthyl, or mixtures thereof. Even more preferably, the three groups are halogenated, preferably fluorinated, aryl groups. Most preferably, the neutral stoichiometric activator is tris perfluorophenyl boron or tris perfluoronaphthyl boron.

Ionic Stoichiometric Activators

Ionic stoichiometric activators may contain an active proton, or some other cation associated with, but not coordinated to, or only loosely coordinated to, the remaining anion of the activator. Such compounds and the like are described in European publications EP 0 570 982 A; EP 0 520 732 A; EP 0 495 375 A; EP 0 500 944 B1; EP 0 277 003 A; EP 0 277 004 A; U.S. Pat. Nos. 5,153,157; 5,198,401; 5,066,741; 5,206,197; 5,241,025; 5,384,299; and 5,502,124; all of which are herein fully incorporated by reference.

Ionic stoichiometric activators comprise a cation, which is preferably a Bronsted acid capable of donating a proton, and a compatible non-coordinating anion. Preferably, the anion is relatively large (bulky), capable of stabilizing the catalytically active species (preferably a group 4 catalytically active species) which is formed when the catalyst (such as a metallocene compound) and the stoichiometric activator are combined. Preferably, the anion will be sufficiently labile to be displaced by olefinic, diolefinic, and acetylenically unsaturated substrates or other neutral Lewis bases, such as ethers, amines, and the like. Two classes of useful compatible non-coordinating anions have been disclosed in EP 0 277,003 A and EP 0 277,004 A: 1) anionic coordination complexes comprising a plurality of lipophilic radicals covalently coordinated to and shielding a central charge-bearing metal or metalloid core, and 2) anions comprising a plurality of boron atoms, such as carboranes, metallacarboranes, and boranes.

Ionic stoichiometric activators comprise an anion, preferably a non-coordinating anion. The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Further, the anion will not transfer an anionic substituent or fragment to the cation so as to cause it to form a neutral four coordinate metallocene compound and a neutral by-product from the anion. Non-coordinating anions useful in accordance with this invention are those that are compatible, stabilize the catalyst (such as metallocene) cation in the sense of balancing its ionic charge at +1, yet retain sufficient lability to permit displacement by an ethylenically or acetylenically unsaturated monomer during polymerization.

In a preferred embodiment of this invention, the ionic stoichiometric activators are represented by the following formula (I):

$$(Z)_d^+ A^{d-} \quad (1)$$

wherein $(Z)_d^+$ is the cation component and $A^{d-}$ is the anion component; where Z is $(L\text{-}H)^+$ or a reducible Lewis Acid, L is an neutral Lewis base; H is hydrogen; $(L\text{-}H)^+$ is a Bronsted acid; $A^{d-}$ is a non-coordinating anion having the charge d−; and d is an integer from 1 to 3.

When Z is (L-H) such that the cation component is $(L\text{-}H)_d^+$, the cation component may include Bronsted acids such as protonated Lewis bases capable of protonating a moiety, such as an alkyl or aryl, from the bulky ligand metallocene containing transition metal catalyst precursor, resulting in a cationic transition metal species. Preferably, the activating cation $(L\text{-}H)_d^+$ is a Bronsted acid, capable of donating a proton to the transition metal catalytic precursor resulting in a transition metal cation, including ammoniums, oxoniums, phosphoniums, silyliums, and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers, such as dimethyl ether diethyl ether, tetrahydrofuran, and dioxane, sulfoniums from thioethers, such as diethyl thioethers and tetrahydrothiophene, and mixtures thereof.

When Z is a reducible Lewis acid, $(Z)_d^+$ is preferably represented by the formula: $(Ar_3C)^+$, where Ar is aryl or aryl substituted with a heteroatom, a $C_1$ to $C_{40}$ hydrocarbyl, or a substituted $C_1$ to $C_{40}$ hydrocarbyl, preferably $(Z)_d^+$ is represented by the formula: $(Ph_3C)^+$, where Ph is phenyl or phenyl substituted with a heteroatom, a $C_1$ to $C_{40}$ hydrocarbyl, or a substituted $C_1$ to $C_{40}$ hydrocarbyl. In a preferred embodiment, the reducible Lewis acid is triphenyl carbenium.

The anion component $A^{d-}$ includes those having the formula $[M^{k+}Q_n]^{d-}$ wherein k is 1, 2, or 3; n is 1, 2, 3, 4, 5, or 6, preferably 3, 4, 5, or 6; (n−k)=d; M is an element selected from group 13 of the Periodic Table of the Elements, preferably boron or aluminum; and each Q is, independently, a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than one occurrence is Q a halide, and two Q groups may form a ring structure. Preferably, each Q is a fluorinated hydrocarbyl group having 1 to 20 carbon atoms, more preferably each Q is a fluorinated aryl group, and most preferably each Q is a pentafluoryl aryl group. Examples of suitable $A^{d-}$ components also include diboron compounds as disclosed in U.S. Pat. No. 5,447,895, which is fully incorporated herein by reference.

In other embodiments of this invention, the ionic stoichiometric activator may be an activator comprising expanded anions, represented by the formula:

$$(A^{*+a})_b(Z^*J^*_j)^{-c}_d;$$

wherein $A^*$ is a cation having charge +a; $Z^*$ is an anion group of from 1 to 50 atoms not counting hydrogen atoms, further containing two or more Lewis base sites; $J^*$ independently each occurrence is a Lewis acid coordinated to at least one Lewis base site of $Z^*$, and optionally two or more such $J^*$ groups may be joined together in a moiety having multiple Lewis acid functionality; j is a number from 2 to 12; and a, b, c, and d are integers from 1 to 3, with the proviso that a×b is equal to c×d. Examples of such activators comprising expandable anions may be found in U.S. Pat. No. 6,395,671, which is fully incorporated herein by reference.

Examples of ionic stoichiometric activators useful in the catalyst system of this invention are:
trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium)tetraphenylborate, tropillium tetraphenylborate, triphenylcarbenium tetraphenylborate, triphenylphosphonium tetraphenylborate triethylsilylium tetraphenylborate, benzene(diazonium)tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium)tetrakis(pentafluorophenyl)borate, tropillium tetrakis(pentafluorophenyl)borate, triphenylcarbenium tetrakis(pentafluorophenyl)borate, triphenylphosphonium tetrakis(pentafluorophenyl)borate, triethylsilylium tetrakis(pentafluorophenyl)borate, benzene(diazonium)tetrakis(pentafluorophenyl)borate, trimethylammonium tetrakis-(2,3,4,6-tetrafluorophenyl)borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium)tetrakis-(2,3,4,6-tetrafluorophenyl)borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium)tetrakis-(2,3,4,6-tetrafluorophenyl)borate, trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis(perfluoronaphthyl)borate, trimethylammonium tetrakis(perfluorobiphenyl)borate, triethylammonium tetrakis(perfluorobiphenyl)borate, tripropylammonium tetrakis(perfluorobiphenyl)borate, tri(n-butyl)ammonium tetrakis(perfluorobiphenyl)borate, tri(t-butyl)ammonium tetrakis(perfluorobiphenyl)borate, N,N-dimethylanilinium tetrakis(perfluorobiphenyl)borate, N,N-diethylanilinium tetrakis(perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis(perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium)tetrakis(3,5-bis(trifluoromethyl)phenyl)borate, tropillium tetrakis(3,5-bis(trifluoromethyl)phenyl)borate, triphenylcarbenium tetrakis(3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl)phenyl)borate, benzene(diazonium)tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl)borate, and tri(2,6-dimethylphenyl)phosphonium tetrakis(pentafluorophenyl)borate.

Most preferably, the ionic stoichiometric activator is N,N-dimethylanilinium tetrakis(perfluoronaphthyl)borate, N,N-dimethylanilinium tetrakis(perfluorobiphenyl)borate, N,N-dimethylanilinium tetrakis(3,5-bis(trifluoromethyl)phenyl)borate, triphenylcarbenium tetrakis(perfluoronaphthyl)borate, triphenylcarbenium tetrakis(perfluorobiphenyl)borate, triphenylcarbenium tetrakis(3,5-bis(trifluoromethyl)phenyl)borate, or triphenylcarbenium tetrakis(perfluorophenyl)borate.

Bulky Ionic Stoichiometric Activators

"Bulky activator" as used herein refers to ionic stoichiometric activators represented by the formula:

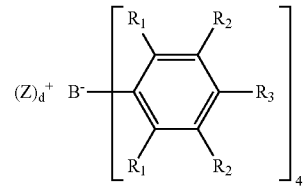

where:
each $R_1$ is, independently, a halide, preferably a fluoride;
each $R_2$ is, independently, a halide, a $C_6$ to $C_{20}$ substituted aromatic hydrocarbyl group or a siloxy group of the formula —O—$S_1$—$R_a$, where $R_a$ is a $C_1$ to $C_{20}$ substituted or unsubstituted hydrocarbyl or hydrocarbylsilyl group (preferably $R_2$ is a fluoride or a perfluorinated phenyl group);
each $R_3$ is a halide, $C_6$ to $C_{20}$ substituted aromatic hydrocarbyl group or a siloxy group of the formula —O—$S_1$—$R_a$, where $R_a$ is a $C_1$ to $C_{20}$ substituted or unsubstituted hydrocarbyl or hydrocarbylsilyl group (preferably $R_3$ is a fluoride or a $C_6$ perfluorinated aromatic hydrocarbyl group); wherein $R_2$ and $R_3$ can form one or more saturated or unsaturated, substituted or unsubstituted rings (preferably $R_2$ and $R_3$ form a perfluorinated phenyl ring); $(Z)_d^+$ is the cation component;

where Z is (L-H) or a reducible Lewis Acid, L is an neutral Lewis base; H is hydrogen; (L-H)+ is a Bronsted acid; and d is an integer from 1 to 3;
wherein the boron anion component has a molecular weight of greater than 1020 g/mol; and
wherein at least three of the substituents on the B atom each have a molecular volume of greater than 250 cubic Å, alternately greater than 300 cubic Å, or alternately greater than 500 cubic Å.

"Molecular volume" is used herein as an approximation of spatial steric bulk of an activator molecule in solution. Comparison of substituents with differing molecular volumes allows the substituent with the smaller molecular volume to be considered "less bulky" in comparison to the substituent with the larger molecular volume. Conversely, a substituent with a larger molecular volume may be considered "more bulky" than a substituent with a smaller molecular volume.

| Element | Relative Volume |
|---|---|
| H | 1 |
| $1^{st}$ short period, Li to F | 2 |
| $2^{nd}$ short period, Na to Cl | 4 |
| $1^{st}$ long period, K to Br | 5 |
| $2^{nd}$ long period, Rb to I | 7.5 |
| $3^{rd}$ long period, Cs to Bi | 9 |

Exemplary bulky substituents of activators suitable herein and their respective scaled volumes and molecular volumes are shown in the table below. The dashed bonds indicate binding to boron, as in the general formula above.

| Activator | Structure of boron substituents | Molecular Formula of each substituent | $V_S$ | MV Per subst. (Å$^3$) | Total MV (Å$^3$) |
|---|---|---|---|---|---|
| Dimethylanilinium tetrakis(perfluoronaphthyl)borate | | $C_{10}F_7$ | 34 | 261 | 1044 |
| Dimethylanilinium tetrakis(perfluorobiphenyl)borate | | $C_{12}F_9$ | 42 | 349 | 1396 |
| [4-tButyl-PhNMe$_2$H] [(C$_6$F$_3$(C$_6$F$_5$)$_2$)$_4$B] | | $C_{18}F_{13}$ | 62 | 515 | 2060 |

Molecular volume may be calculated as reported in "A Simple 'Back of the Envelope' Method for Estimating the Densities and Molecular Volumes of Liquids and Solids," Journal of Chemical Education, Vol. 71, No. 11, November 1994, pp. 962-964. Molecular volume (MV), in units of cubic Å, is calculated using the formula: MV=8.3$V_S$, where $V_S$ is the scaled volume. $V_S$ is the sum of the relative volumes of the constituent atoms, and is calculated from the molecular formula of the substituent using the following table of relative volumes. For fused rings, the $V_S$ is decreased by 7.5% per fused ring.

Exemplary bulky ionic stoichiometric activators useful in catalyst systems herein include: trimethylammonium tetrakis(perfluoronaphthyl)borate, triethylammonium tetrakis(perfluoronaphthyl)borate, tripropylammonium tetrakis(perfluoronaphthyl)borate, tri(n-butyl)ammonium tetrakis(perfluoronaphthyl)borate, tri(t-butyl)ammonium tetrakis(perfluoronaphthyl)borate, N,N-dimethylanilinium tetrakis(perfluoronaphthyl)borate, N,N-diethylanilinium tetrakis(perfluoronaphthyl)borate, N,N-dimethyl-(2,4,6-trimethylanilinium)tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium)tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium)tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium)tetrakis (perfluorobiphenyl)borate, [4-t-butyl-PhNMe$_2$H][(C$_6$F$_3$(C$_6$F$_5$)$_2$)$_4$B], (where Ph is phenyl and Me is methyl), and the types disclosed in U.S. Pat. No. 7,297,653.

In another embodiment of this invention, an activation method using ionic compounds not containing an active proton but capable of producing a bulky ligand metallocene catalyst cation and their non-coordinating anion are also contemplated, and are described in EP 0 426 637 A, EP 0 573 403 A, and U.S. Pat. No. 5,387,568, which are all herein incorporated by reference.

In another embodiment of this invention, inventive processes also can employ stoichiometric activator compounds that are initially neutral Lewis acids but form a cationic metal complex and a noncoordinating anion, or a zwitterionic complex upon reaction with the metallocene compounds. For example, tris(pentafluorophenyl)boron or aluminum may act to abstract a hydrocarbyl or hydride ligand to yield an invention cationic metal complex and stabilizing noncoordinating anion, see EP 0 427 697 A and EP 0 520 732 A for illustrations of analogous group 4 metallocene compounds. Also, see the methods and compounds of EP 0 495 375 A. For formation of zwitterionic complexes using analogous group 4 compounds, see U.S. Pat. Nos. 5,624,878; 5,486,632; and 5,527,929.

In another embodiment of this invention, another suitable ionic stoichiometric activator comprises a salt of a cationic oxidizing agent and a noncoordinating, compatible anion represented by the formula:

$$(X^{e+})_d(A^{d-})_e \qquad (3)$$

wherein $X^{e+}$ is a cationic oxidizing agent having a charge of e+; e is 1, 2, or 3; $A^{d-}$ is a non-coordinating anion having the charge d−; and d is 1, 2, or 3. Examples of $X^{e+}$ include: ferrocenium, hydrocarbyl-substituted ferrocenium, Ag$^+$, or Pb$^{+2}$. Preferred embodiments of $A^{d-}$ are those anions previously defined with respect to the Bronsted acid containing activators, especially tetrakis(pentafluorophenyl)borate.

Activator Combinations

It is within the scope of this invention that metallocene compounds can be combined with one or more activators or activation methods described above. For example, a combination of activators have been described in U.S. Pat. Nos. 5,153,157; 5,453,410; European Publication No. EP 0 573 120 B1; PCT Publication Nos. WO 94/07928; and WO 95/14044. These documents all discuss the use of an alumoxane in combination with a stoichiometric activator.

In another embodiment, the vinyl terminated macromonomer may be a vinyl terminated ethylene macromonomer. In some embodiments, a phenoxyimine-based catalyst (a Mitsui FI catalyst) or a pyrroleimine-based catalyst (a Mitsui PI catalyst) can be used to prepare the vinyl terminated ethylene macromonomer. These catalysts comprise (a) a transition metal (preferably Ti) compound having phenoxyimine or pyrroleimine as a ligand, and (b) one or more kind(s) of compound selected from (b-1) an organic metal compound, (b-2) an organic aluminumoxy compound, and (b-3) a compound that reacts with the transition metal compound (a) to form an ion pair, as described in JP-A-2001-72706, JP-A-2002-332312, JP-A-2003-313247, JP-A-2004-107486, and JP-A-2004-107563. Herein, as the transition metal contained in the transition metal compound, the transition metal of Groups 3 to 11 in the periodic table can be used. Preferred catalysts to prepare the vinyl terminated ethylene macromonomer include those described in U.S. Pat. No. 7,795,347, specifically at column 16, line 56 et seq. in Formula (XI).

In another embodiment, the vinyl terminated macromonomer may be a vinyl terminated isotactic polypropylene or a vinyl terminated polyethylene as disclosed in U.S. Pat. Nos. 6,444,773; 6,555,635; 6,147,180; 6,660,809; 6,750,307; 6,774,191; 6,169,154; and EP 0 958 309, which are incorporated by reference herein.

In a preferred embodiment, any vinyl terminated macromonomer described herein can be fractionated or distilled by any means know in the art and one or more of the fractions may be used in the invention described herein. Preferred fractions typically have a narrow Mw/Mn, such as less than 1.5, preferably 1.4 or less, preferably 1.3 or less, preferably 1.2 or less. Alternately, the Mw/Mn is from 1 to 1.4, preferably 1.05 to 1.3, preferably 1.1 to 1.2.

In another embodiment of the invention, the fractions have a narrow boiling point range (as determined by ASTM D86) of less than 70° C., preferably less than 60° C., preferably less than 50° C., preferably less than 40° C., preferably less than 30° C., preferably less than 20° C., preferably less than 10° C.

In a preferred embodiment of the invention, the vinyl terminated macromonomer injected into a gas chromatograph column to determine the optimum cut points for the fractionation.

In a preferred embodiment, the fractions may be obtained by separation of the vinyl terminated macromonomer product such as by the processes described in GB 1550419A; U.S. Pat. Nos. 3,647,906; and 3,592,866. Useful fractions include ranges from about 4 carbon-numbers up to 20 carbon-numbers, e.g. C$_4$-C$_8$, C$_4$-C$_{14}$, C$_4$-C$_{20}$. The lower α-olefin fraction may contain α-olefins having the same carbon-number as the lowest (α-olefin in the higher α-olefin fraction, but preferably contains only α-olefins of carbon-numbers lower than the carbon-number of the lowest α-olefin in the higher α-olefin fraction. The higher (α-olefin fraction may include α-olefins of the same carbon number as the highest α-olefin in the lower α-olefin fraction up to the highest α-olefin produced in the reaction, but generally not higher than C$_{40}$. Preferably, however, the higher α-olefin fraction contains only (α-olefins of carbon-numbers higher than the carbon number of the highest α-olefin in the lower α-olefin fraction.

In a separation where an α-olefin product mixture free of light oligomers, e.g., dimers, trimers, tetramers, etc., is desired, the lower α-olefin fraction is further separated into a light α-olefin fraction and an intermediate α-olefin fraction. The light α-olefin fraction may include from C$_4$ up to C$_{12}$, e.g., C$_4$-C$_6$, C$_4$-C$_8$, C$_4$-C$_{10}$, etc. In this modification, the intermediate α-olefin fraction is removed as product and the light α-olefin fraction is converted to additional intermediate α-olefins.

In another embodiment, any vinyl terminated macromonomer described herein can be separated into different boiling point cuts by distillation performed according to the procedures described in ASTM methods D2892 and D5236. (D2892: Standard Test Method for Distillation of Crude Petroleum (15-Theoretical Plate Column) and D5236: Standard Test Method for Distillation of Heavy Hydrocarbon Mixtures (Vacuum Potstill Method).)

For example, a low molecular weight atactic polypropylene VTM (677.3 gram charge) can be fractionated or distilled using the boiling point range, mass recovery, vacuum conditions listed below. Both initial boiling point (IBP) and final boiling point (FBP) are in degree Fahrenheit (° F.) and corrected to atmospheric pressure.

| Fraction (Cut) # | Initial boiling point/IBP (° F.) | Final boiling point/FBP (° F.) | Weight of collected fraction (grams) | Still pressure (mmHg) | ASTM method used |
|---|---|---|---|---|---|
| Charge (Feed) | — | — | 677.3 | | |
| 1 | IBP | 140 | 3.8 | 760 | D2892 |
| 2 | 140 | 160 | 11.9 | 760 | D2892 |
| 3 | 160 | 265 | 27.8 | 760 | D2892 |
| 4 | 265 | 365 | 35.0 | 88 | D2892 |
| 5 | 365 | 465 | 46.6 | 88 | D2892 |
| 6 | 465 | 525 | 34.4 | 88 | D2892 |
| 7 | 525 | 568 | 44.0 | 10 | D2892 |
| 8 | 568 | 588 | 14.2 | 10 | D2892 |
| 9 | 588 | 645 | 53.1 | 10 | D2892 |
| 10 | 645 | 700 | 63.4 | 2 | D2892 |
| 11 | 700 | 844 | 41.2 | 0.2 | D5236 |
| 12 | 844 | 892 | 42.3 | 0.2 | D5236 |
| 13 | 892 | 904 | 17.9 | 0.2 | D5236 |
| Distillation Bottoms | 904+ | — | 226.6 | — | — |

As shown in the table above, total recovery of collected fractions (fraction 1 to 13) with boiling points between 25° C. and 904° F. was 435.6 g (64.3 wt % of initial charge). Total recovery of distillation bottoms with boiling point above 904° F. was 226.6 g (33.5 wt % of initial charge). The total recovery of both distilled fractions and bottoms material amounts to 97.8 wt %. The resulting distilled fractions and distillation bottoms have narrow molecular weight distributions (Mw/Mn<1.4) as determined by GPC.

In another embodiment of the invention, the vinyl terminated macromonomer (preferably a propylene based vinyl terminated macromonomer, preferably a homopolypropylene vinyl terminated macromonomer) has less than 1 mol % regio defects (as determined by $^{13}C$ NMR), based upon the total propylene monomer. Three types of defects are defined to be the regio defects: 2,1-erythro, 2,1-threo, and 3,1-isomerization. The structures and peak assignments for these are given in L. Resconi, L. Cavallo, A. Fait, and F. Piemontesi, Chem. Rev. 2000, 100, pp. 1253-1345, as well as H. N. Cheng, *Macromolecules,* 17, p. 1950 (1984). Alternately, the vinyl terminated macromonomer (preferably a propylene based vinyl terminated macromer, preferably a homopolypropylene vinyl terminated macromonomer) has less than 250 regio defects per 10,000 monomer units (as determined by $^{13}C$ NMR), preferably less than 150, preferably less than 100, preferably less than 50 regio defects per 10,000 monomer units. The regio defects each give rise to multiple peaks in the carbon NMR spectrum, and these are all integrated and averaged (to the extent that they are resolved from other peaks in the spectrum), to improve the measurement accuracy. The chemical shift offsets of the resolvable resonances used in the analysis are tabulated below. The precise peak positions may shift as a function of NMR solvent choice.

| Regio defect | Chemical shift range (ppm) |
|---|---|
| 2,1-erythro | 42.3, 38.6, 36.0, 35.9, 31.5, 30.6, 17.6, 17.2 |
| 2,1-threo | 43.4, 38.9, 35.6, 34.7, 32.5, 31.2, 15.4, 15.0 |
| 3,1 insertion | 37.6, 30.9, 27.7 |

The average integral for each defect is divided by the integral for one of the main propylene signals ($CH_3$, CH, $CH_2$), and multiplied by 10,000 to determine the defect concentration per 10,000 monomers.

In another embodiment, any vinyl terminated macromonomer described herein may have a melting point (DSC first melt) of from 60° C. to 160° C., alternately 50° C. to 145° C., alternately 50° C. to 130° C., alternately 50° C. to 100° C. In another embodiment, the vinyl terminated macromonomer described herein have no detectable melting point by DSC following storage at ambient temperature (23° C.) for at least 48 hours.

In another embodiment, the vinyl terminated macromonomer described herein may have a glass transition temperature of less than 0° C. or less (DSC), preferably −10° C. or less, more preferably −20° C. or less, more preferably −30° C. or less, more preferably −50° C. or less.

Melting temperature ($T_m$) and glass transition temperature (Tg) are measured using Differential Scanning calorimetry (DSC) using commercially available equipment such as a TA Instruments 2920 DSC. Typically, 3 to 10 mg of the sample, that has been stored at 25° C. for at least 48 hours, is sealed in an aluminum pan and loaded into the instrument at 25° C. The sample is equilibrated at 25° C., then it is cooled at a cooling rate of 10° C./min to −80° C. The sample is held at −80° C. for 5 min and then heated at a heating rate of 10° C./min to 25° C. The glass transition temperature is measured from the heating cycle. Alternatively, the sample is equilibrated at 25° C., then heated at a heating rate of 10° C./min to 150° C. The endothermic melting transition, if present, is analyzed for onset of transition and peak temperature. The melting temperatures reported are the peak melting temperatures from the first heat unless otherwise specified. For samples displaying multiple peaks, the melting point (or melting temperature) is defined to be the peak melting temperature (i.e., associated with the largest endothermic calorimetric response in that range of temperatures) from the DSC melting trace.

In another embodiment, the vinyl terminated macromonomers described herein are a liquid at 25° C.

In a particularly preferred embodiment of the invention, the vinyl terminated macromonomer (preferably comprising propylene, at least 50 mol % propylene, preferably at least 70 propylene) has less than 250 regio defects per 10,000 monomer units, preferably less than 150, preferably less than 100, preferably less than 50 regio defects per 10,000 monomer units and a Tg of less than 0° C. or less (DSC), preferably −10° C. or less, more preferably −20° C. or less, more preferably −30° C. or less, more preferably −50° C. or less In another embodiment, the vinyl terminated macromonomers described herein have a viscosity at 60° C. of greater than 1,000 cP, greater than 12,000 cP, or greater than 100,000 cP. In other embodiments, the vinyl terminated macromonomer have a viscosity of less than 200,000 cP, less than 150,000 cP, or less than 100,000 cP. Viscosity is defined as resistance to flow and the melt viscosity of neat copolymers is measured at elevated temperature using a Brookfield Digital Viscometer.

In another embodiment, the VTM described herein also has a viscosity (also referred to a Brookfield Viscosity or Melt Viscosity) of 90,000 mPa·sec or less at 190° C. (as measured by ASTM D 3236 at 190° C.; ASTM=American Society for Testing and Materials); or 80,000 mPa·sec or less, or 70,000 mPa·sec or less, or 60,000 mPa·sec or less, or 50,000 mPa·sec or less, or 40,000 mPa·sec or less, or 30,000 mPa·sec or less, or 20,000 mPa·sec or less, or 10,000 mPa·sec or less, or 8,000 mPa·sec or less, or 5,000 mPa·sec or less, or 4,000 mPa·sec or less, or 3,000 mPa·sec or less, or 1,500 mPa·sec or less, or between 250 and 6000 mPa·sec, or between 500 and 5,500 mPa·sec, or between 500 and 3,000 mPa·sec, or between 500 and 1,500 mPa·sec, and/or a viscosity of 8,000 mPa·sec or less at 160° C. (as measured by ASTM D 3236 at 160° C.); or 7,000 mPa·sec or less, or 6,000 mPa·sec or less, or 5,000 mPa·sec or less, or 4,000 mPa·sec or less, or 3,000 mPa·sec or less, or 1,500 mPa·sec or less, or between 250 and 6,000 mPa·sec, or between 500 and 5,500 mPa·sec, or between 500 and 3,000 mPa·sec, or between 500 and 1,500 mPa·sec. In other embodiments, the viscosity is 200,000 mPa·sec or less at 190° C., depending on the application. In other embodiments, the viscosity is 50,000 mPa·sec or less depending on the applications.

Vinyl and Vinylene Monomers

Vinyl and vinylene monomers useful herein include those represented by the formula:

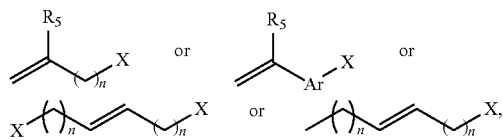

wherein each X is, independently, $-CO_2R$, $-CONR_1R_2$, CN, a $C_1$ to a $C_{20}$ alkyl group, preferably methyl, ethyl, propyl, butyl, pentyl, hexyl, heptyl, octyl, nonyl, decyl, undecyl, dodecyl, tetradecyl, hexadecyl, or octadecyl;

R is a $C_1$ to a $C_{20}$ alkyl group or an aromatic group, preferably methyl, ethyl, propyl, butyl, pentyl, hexyl, heptyl, octyl, nonyl, decyl, undecyl, dodecyl, tetradecyl, hexadecyl, or octadecyl;

each $R_1$ and $R_2$ is, independently, a hydrogen, a $C_1$ to a $C_{20}$ alkyl group, or an aromatic group, preferably methyl, ethyl, propyl, butyl, pentyl, hexyl, heptyl, octyl, nonyl, decyl, undecyl, dodecyl, tetradecyl, hexadecyl, octadecyl, phenyl, benzyl;

each $R_5$ is, independently, a hydrogen atom or a $C_1$ to a $C_{40}$ alkyl group, preferably methyl, ethyl, propyl, butyl, pentyl, hexyl, heptyl, octyl, nonyl, decyl, undecyl, dodecyl, tetradecyl, hexadecyl, or octadecyl;

each Ar is, independently, an aromatic group, preferably phenyl or benzyl; and each n is, independently, from 0 to about 40, preferably 1 to 30, preferably 5 to 20.

In another embodiment, the monomer can a vinyl terminated macromonomer (VTM) as described herein.

Alkene Metathesis Catalysts

An alkene metathesis catalyst is a compound that catalyzes the reaction between a first olefin (typically vinyl) with a second olefin (typically vinyl or vinylene) to produce a product, typically with the elimination of ethylene.

In a preferred embodiment, the alkene metathesis catalyst useful herein is represented by the Formula (I):

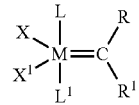

Formula (I)

where:

M is a Group 8 metal, preferably Ru or Os, preferably Ru;

X and $X^1$ are, independently, any anionic ligand, preferably a halogen (preferably chlorine), an alkoxide or a triflate, or X and $X^1$ may be joined to form a dianionic group and may form single ring of up to 30 non-hydrogen atoms or a multinuclear ring system of up to 30 non-hydrogen atoms;

L and $L^1$ are, independently, a neutral two electron donor, preferably a phosphine or a N-heterocyclic carbene, L and $L^1$ may be joined to form a single ring of up to 30 non-hydrogen atoms or a multinuclear ring system of up to 30 non-hydrogen atoms;

L and X may be joined to form a multidentate monoanionic group and may form single ring of up to 30 non-hydrogen atoms or a multinuclear ring system of up to 30 non-hydrogen atoms;

$L^1$ and $X^1$ may be joined to form a multidentate monoanionic group and may form single ring of up to 30 non-hydrogen atoms or a multinuclear ring system of up to 30 non-hydrogen atoms;

R and $R^1$ are, independently, hydrogen or $C_1$ to $C_{30}$ substituted or unsubstituted hydrocarbyl (preferably a $C_1$ to $C_{30}$ substituted or unsubstituted alkyl or a substituted or unsubstituted $C_4$ to $C_{30}$ aryl);

$R^1$ and $L^1$ or $X^1$ may be joined to form single ring of up to 30 non-hydrogen atoms or a multinuclear ring system of up to 30 non-hydrogen atoms; and R and L or X may be joined to form single ring of up to 30 non-hydrogen atoms or a multinuclear ring system of up to 30 non-hydrogen atoms.

Preferred alkoxides include those where the alkyl group is a phenol, substituted phenol (where the phenol may be substituted with up to 1, 2, 3, 4, or 5 $C_1$ to $C_{12}$ hydrocarbyl groups) or a $C_1$ to $C_{10}$ hydrocarbyl, preferably a $C_1$ to $C_{10}$ alkyl group, preferably methyl, ethyl, propyl, butyl, or phenyl.

Preferred triflates are represented by the Formula (II):

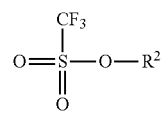

Formula (II)

where $R^2$ is hydrogen or a $C_1$ to $C_{30}$ hydrocarbyl group, preferably a $C_1$ to $C_{12}$ alkyl group, preferably methyl, ethyl, propyl, butyl, or phenyl.

Preferred N-heterocyclic carbenes are represented by the Formula (III) or the Formula (IV):

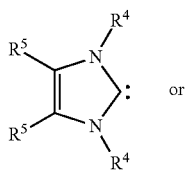

Formula (III)

or

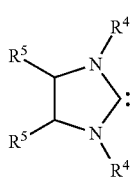

Formula (IV)

where:
each $R^4$ is independently a hydrocarbyl group or substituted hydrocarbyl group having 1 to 40 carbon atoms, preferably methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluoyl, chlorophenyl, phenol, substituted phenol, or $CH_2C(CH_3)_3$; and
each $R^5$ is hydrogen, a halogen, or a $C_1$ to $C_{12}$ hydrocarbyl group, preferably hydrogen, bromine, chlorine, methyl, ethyl, propyl, butyl, or phenyl.

In other useful embodiments, one of the N groups bound to the carbene in formula (III) or (IV) is replaced with an S, O, or P atom, preferably an S atom.

Other useful N-heterocyclic carbenes include the compounds described in Hermann, W. A. Chem. Eur. J., 1996, 2, pp. 772 and 1627; Enders, D. et al. Angew. Chem. Int. Ed., 1995, 34, p. 1021; Alder R. W., Angew. Chem. Int. Ed., 1996, 35, p. 1121; and Bertrand, G. et al., Chem. Rev., 2000, 100, p. 39.

In a preferred embodiment, the alkene metathesis catalyst is one or more of tricyclohexylphosphine[1,3-bis(2,4,6-trimethylphenyl)imidazol-2-ylidene][3-phenyl-1H-inden-1-ylidene]ruthenium(II)dichloride, tricyclohexylphosphine[3-phenyl-1H-inden-1-ylidene][1,3-bis(2,4,6-trimethylphenyl)-4,5-dihydro-imidazol-2-ylidene] ruthenium(II)dichloride, tricyclohexylphosphine[1,3-bis(2,4,6-trimethylphenyl)-4,5-dihydroimidazol-2-ylidene] [(phenylthio)methylene]ruthenium(II)dichloride, bis(tricyclohexylphosphine)-3-phenyl-1H-inden-1-ylideneruthenium(II)dichloride, 1,3-Bis(2,4,6-trimethylphenyl)-4,5-dihydroimidazol-2-ylidene[2-(i-propoxy)-5-(N,N-dimethylaminosulfonyl)phenyl] methyleneruthenium(II)dichloride, and [1,3-Bis(2,4,6-trimethylphenyl)-2-imidazolidinylidene]-2-[[(4-methylphenyl)imino]methyl]-4-nitrophenolyl]-[3-phenyl-1H-inden-1-ylidene]ruthenium(II) chloride. In a preferred embodiment, the catalyst is 1,3-Bis(2,4,6-trimethylphenyl)-4,5-dihydroimidazol-2-ylidene[2-(i-propoxy)-5-(N,N-dimethylaminosulfonyl)phenyl]methyleneruthenium(II)dichloride and/or Tricyclohexylphosphine[3-phenyl-1H-inden-1-ylidene][1,3-bis(2,4,6-trimethylphenyl)-4,5-dihydroimidazol-2-ylidene]ruthenium(II)dichloride.

In another embodiment, the alkene metathesis catalyst is represented by Formula (I) above, where: M is Os or Ru; $R^1$ is hydrogen; X and $X^1$ may be different or the same and are any anionic ligand; L and $L^1$ may be different or the same and are any neutral electron donor; and R may be hydrogen, substituted or unsubstituted alkyl, or substituted or unsubstituted aryl. R is preferably hydrogen, $C_1$ to $C_{20}$ alkyl, or aryl. The $C_1$ to $C_{20}$ alkyl may optionally be substituted with one or more aryl, halide, hydroxy, $C_1$ to $C_{20}$ alkoxy, or $C_2$ to $C_{20}$ alkoxycarbonyl groups. The aryl may optionally be substituted with one or more $C_1$ to $C_{20}$ alkyl, aryl, hydroxyl, $C_1$ to $C_5$ alkoxy, amino, nitro, or halide groups. L and $L^1$ are preferably phosphines of the formula $PR^{3'} R^{4'} R^{5'}$, where $R^{3'}$ is a secondary alkyl or cycloalkyl, and $R^{4'}$ and $R^{5'}$ are aryl, $C_1$ to $C_{10}$ primary alkyl, secondary alkyl, or cycloalkyl. $R^{4'}$ and $R^{5'}$ may be the same or different. L and $L^1$ are preferably the same and are —P(cyclohexyl)$_3$, —P(cyclopentyl)$_3$, or —P(isopropyl)$_3$. X and $X^1$ are most preferably the same and are chlorine.

In another embodiment of the present invention, the ruthenium and osmium carbene compounds have the Formula (V):

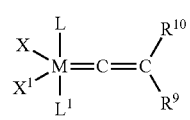

Formula (V)

where M is Os or Ru, preferably Ru; X, $X^1$, L, and $L^1$ are as described above; and $R^9$ and $R^{10}$ may be different or the same and may be hydrogen, substituted or unsubstituted alkyl, or substituted or unsubstituted aryl. The $R^9$ and $R^{10}$ groups may optionally include one or more of the following functional groups: alcohol, thiol, ketone, aldehyde, ester, ether, amine, imine, amide, nitro, carboxylic acid, disulfide, carbonate, isocyanate, carbodiimide, carboalkoxy, and halogen groups. Such compounds and their synthesis are described in U.S. Pat. No. 6,111,121.

In another embodiment, the alkene metathesis catalyst useful herein may be any of the catalysts described in U.S. Pat. Nos. 6,111,121; 5,312,940; 5,342,909; 7,329,758; 5,831,108; 5,969,170; 6,759,537; 6,921,735; and U.S. Patent Publication No. 2005-0261451 A1, including, but not limited to, benzylidene-bis(tricyclohexylphosphine)dichlororuthenium, benzylidene[1,3-bis(2,4,6-trimethylphenyl)-2-imidazolidinylidene]dichloro(tricyclohexylphosphine)ruthenium, dichloro(o-isopropoxyphenylmethylene)(tricyclohexylphosphine)ruthenium(II), (1,3-Bis-(2,4,6-trimethylphenyl)-2-imidazolidinylidene)dichloro(o-isopropoxyphenylmethylene)ruthenium, 1,3-Bis(2-methylphenyl)-2-imidazolidinylidene]dichloro(2-isopropoxyphenylmethylene) ruthenium(II), [1,3-Bis(2,4,6-trimethylphenyl)-2-imidazolidinylidene]dichloro[3-(2-pyridinyl)propylidene]ruthenium(II), [1,3-Bis(2-methylphenyl)-2-imidazolidinylidene]dichloro (phenylmethylene) (tricyclohexylphosphine)ruthenium(II), [1,3-Bis(2,4,6-trimethylphenyl)-2-imidazolidinylidene] dichloro(3-methyl-2-butenylidene)(tricyclohexylphosphine) ruthenium(II), and [1,3-Bis(2,4,6-trimethylphenyl)-2-imidazolidinylidene]dichloro(benzylidene)bis(3-bromopyridine) ruthenium(II).

In another embodiment, the alkene metathesis catalyst is represented by the formula:

Formula (VI)

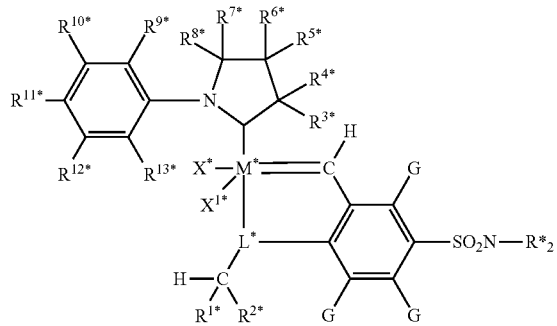

where:

M* is a Group 8 metal, preferably Ru or Os, preferably Ru;
X* and $X^{1*}$ are, independently, any anionic ligand, preferably a halogen (preferably $C_1$), an alkoxide or an alkyl sulfonate, or X and $X^1$ may be joined to form a dianionic group and may form single ring of up to 30 non-hydrogen atoms or a multinuclear ring system of up to 30 non-hydrogen atoms;
L* is N, O, P, or S, preferably N or O;
R* is hydrogen or a $C_1$ to $C_{30}$ hydrocarbyl or substituted hydrocarbyl, preferably methyl;
$R^{1*}$, $R^{2*}$, $R^{3*}$, $R^{4*}$, $R^{5*}$, $R^{6*}$, $R^{7*}$, and $R^{8*}$ are, independently, hydrogen or a $C_1$ to $C_{30}$ hydrocarbyl or substituted hydrocarbyl, preferably methyl, ethyl, propyl or butyl, preferably $R^{1*}$, $R^{2*}$, $R^{3*}$, and $R^{4*}$ are methyl;
each $R^{9*}$ and $R^{13*}$ are, independently, hydrogen or a $C_1$ to $C_{30}$ hydrocarbyl or substituted hydrocarbyl, preferably a $C_2$ to $C_6$ hydrocarbyl, preferably ethyl;
$R^{10*}$, $R^{11*}$, $R^{12*}$ are, independently hydrogen or a $C_1$ to $C_{30}$ hydrocarbyl or substituted hydrocarbyl, preferably hydrogen or methyl;
each G, is, independently, hydrogen, halogen or $C_1$ to $C_{30}$ substituted or unsubstituted hydrocarbyl (preferably a $C_1$ to $C_{30}$ substituted or unsubstituted alkyl or a substituted or unsubstituted $C_4$ to $C_{30}$ aryl);
where any two adjacent R groups may form a single ring of up to 8 non-hydrogen atoms or a multinuclear ring system of up to 30 non-hydrogen atoms.

Preferably, any two adjacent R groups may form a fused ring having from 5 to 8 non hydrogen atoms. Preferably the non-hydrogen atoms are C and/or o. Preferably the adjacent R groups form fused rings of 5 to 6 ring atoms, preferably 5 to 6 carbon atoms. By adjacent is meant any two R groups located next to each other, for example $R^{3*}$ and $R^{4*}$ can form a ring and/or RU* and $R^{12*}$ can form a ring.

In a preferred embodiment, the metathesis catalyst compound comprises one or more of: 2-(2,6-diethylphenyl)-3,5,5,5-tetramethylpyrrolidine[2-(i-propoxy)-5-(N,N-dimethylaminosulfonyl)phenyl]methylene ruthenium dichloride; 2-(mesityl)-3,3,5,5-tetramethylpyrrolidine[2-(i-propoxy)-5-(N,N-dimethylaminosulfonyl)phenyl]methylene ruthenium dichloride; 2-(2-isopropyl)-3,3,5,5-tetramethylpyrrolidine[2-(i-propoxy)-5-(N,N-dimethylaminosulfonyl)phenyl]methylene ruthenium dichloride; 2-(2,6-diethyl-4-fluorophenyl)-3,3,5,5-tetramethylpyrrolidine[2-(i-propoxy)-5-(N,N-dimethylaminosulfonyl)phenyl]methylene ruthenium dichloride, or mixtures thereof.

For further information on such alkene metathesis catalysts, please see U.S. Pat. No. 8,063,232.

The above named catalysts are generally available for Sigma-Aldrich Corp. (St. Louis, Mo.) or Strem Chemicals, Inc. (Newburyport, Mass.).

In a preferred embodiment of the present invention, the invention relates to a metathesis catalyst comprising: a Group 8 metal complex represented by the formula (H):

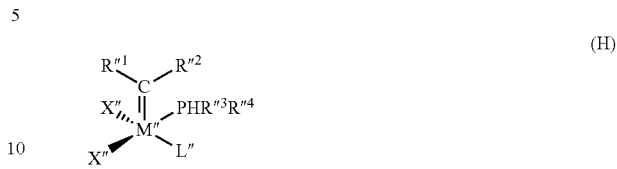

wherein

M" is a Group 8 metal (preferably M is ruthenium or osmium, preferably ruthenium);

each X" is independently an anionic ligand (preferably selected from the group consisting of halides, alkoxides, aryloxides, and alkyl sulfonates, preferably a halide, preferably chloride);

$R''^1$ and $R''^2$ are independently selected from the group consisting of hydrogen, a $C_1$ to $C_{30}$ hydrocarbyl, and a $C_1$ to $C_{30}$ substituted hydrocarbyl (preferably $R''^1$ and $R''^2$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl);

$R''^3$ and $R''^4$ are independently selected from the group consisting of hydrogen, $C_1$ to $C_{12}$ hydrocarbyl groups, substituted $C_1$ to $C_{12}$ hydrocarbyl groups, and halides (preferably $R''^3$ and $R''^4$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl); and L" is a neutral donor ligand, preferably L" is selected from the group consisting of a phosphine, a sulfonated phosphine, a phosphite, a phosphinite, a phosphonite, an arsine, a stibine, an ether, an amine, an imine, a sulfoxide, a carboxyl, a nitrosyl, a pyridine, a thioester, a cyclic carbene, and substituted analogs thereof; preferably a phosphine, a sulfonated phosphine, an N-heterocyclic carbene, a cyclic alkyl amino carbene, and substituted analogs thereof (preferably L" is selected from a phosphine, an N-heterocyclic carbene, a cyclic alkyl amino carbene, and substituted analogs thereof).

A "cyclic carbene" may be defined as a cyclic compound with a neutral dicoordinate carbon center featuring a lone pair of electrons. Such cyclic carbenes may be represented by the formula (IV) below:

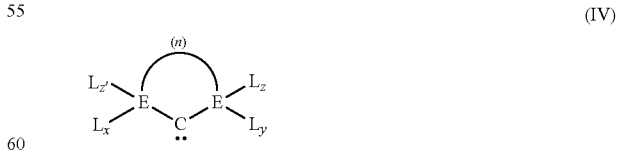

where
n is a linking group comprising from one to four ring vertices selected from the group consisting of C, Si, N, P, O, and S, with available valences optionally occupied by H, oxo, hydrocarbyl, or substituted hydrocarbyl groups; preferably, n comprises two ring vertices of carbon with available valences occupied by H, oxo, hydrocarbyl or substituted hydrocarbyl groups; preferably n is $C_2H_2$, $C_2H_4$, or substituted versions thereof;

each E is independently selected from the group comprising C, N, S, O, and P, with available valences optionally occupied by Lx, Ly, Lz, and Lz'; preferably, at least one E is a C;

preferably, one E is a C and the other E is a N; preferably, both E's are C; and Lx, Ly, Lz, and Lz' are independently selected from the group comprising hydrogen, hydrocarbyl groups, and substituted hydrocarbyl groups; preferably, Lx, Ly, Lz, and Lz' are independently selected from the group comprising a hydrocarbyl group and substituted hydrocarbyl group having 1 to 40 carbon atoms; preferably, Lx, Ly, Lz, and Lz' are independently selected from the group comprising $C_{1-10}$ alkyl, substituted $C_{1-10}$ alkyl, $C_{2-10}$ alkenyl, substituted $C_{2-10}$ alkenyl, $C_{2-10}$ alkynyl, substituted $C_{2-10}$ alkynyl, aryl, and substituted aryl; preferably, Lx, Ly, Lz, and Lz' are independently selected from the group comprising methyl, ethyl, propyl, butyl (including isobutyl and n-butyl), pentyl, cyclopentyl, hexyl, cyclohexyl, octyl, cyclooctyl, nonyl, decyl, cyclodecyl, dodecyl, cyclododecyl, mesityl, adamantyl, phenyl, benzyl, toluoyl, chlorophenyl, 2,6-diethylphenyl, 2,6-diisopropylphenyl, 2-isopropylphenyl, 2-ethyl-6-methylphenyl, 3,5-ditertbutylphenyl, 2-tertbutylphenyl, and 2,3,4,5,6-pentamethylphenyl. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Examples of cyclic carbenes useful in embodiments of the present invention include:

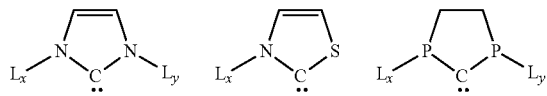

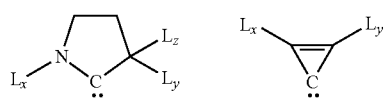

where Lx, Ly, and Lz are as defined above. In some embodiments, at least two of Lx, Ly, Lz, and Lz' may be joined to form a 3- to 12-membered spirocyclic ring, with available valences optionally occupied by H, oxo, halogens, hydrocarbyl or substituted hydrocarbyl groups. Useful substituents include $C_{1-10}$ alkyl, $C_{2-10}$ alkenyl, $C_{2-10}$ alkynyl, aryl, $C_{1-10}$ alkoxy, $C_{2-10}$ alkenyloxy, $C_{2-10}$ alkynyloxy, aryloxy, $C_{2-10}$ alkoxycarbonyl, $C_{1-10}$ alkylthio, $C_{1-10}$ alkylsulfonyl, fluoro, chloro, bromo, iodo, oxo, amino, imine, nitrogen heterocycle, hydroxy, thiol, thiono, phosphorous, and carbene groups.

Preferred cyclic carbenes include N-heterocyclic carbenes (NHCs). For purposes of this invention and claims thereto, NHCs are cyclic carbenes of the types described in Formula II above, where each E is N and the available valences on the N are occupied by Lx and Ly. Preferred NHCs may be represented by the formula:

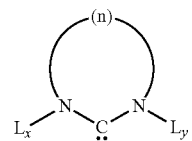

where
n, Lx, and Ly are as described above in Formula (IV).
Some particularly useful NHCs include:

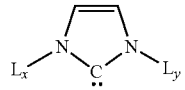 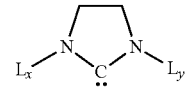

where Lx and Ly are as described above. Other useful NHCs include the compounds described in Hermann, W. A. Chem. Eur. J. 1996, 2, p. 772 and p. 1627; Enders, D. et al., Angew. Chem. Int. Ed. 1995, 34, p. 1021; Alder R. W., Angew. Chem. Int. Ed. 1996, 35, p. 1121; U.S. Publication No. 2011-0112302; and Bertrand, G. et al., Chem. Rev. 2000, 100, p. 39.

Particularly preferred cyclic carbenes include cyclic alkyl amino carbines (CAACs). In all embodiments herein, CAACs are cyclic carbenes of the types described in Formula II above, where one E is N and the other E is C, and the available valences on the N and C are occupied by Lx, Ly, and Lz. CAACs may be represented by the formula:

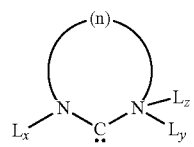

where
n, Lx, Ly, and Lz are as described above in Formula (IV).
Some particularly useful CAACs include:

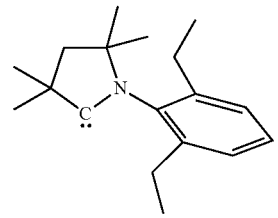

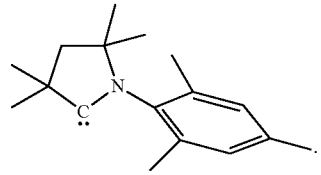

Other useful CAACs include the compounds described in U.S. Pat. No. 7,312,331; U.S. Pat. No. 8,063,232; and Bertrand et al, *Angew. Chem. Int. Ed.* 2005, 44, pp. 7236-7239.

Other carbenes useful in embodiments of the present invention include thiazolyldenes, P-heterocyclic carbenes (PHCs), and cyclopropenylidenes.

With respect to Group 8 metal complexes of Formula (H), the phosphine ligands (PHR'''$^3$R'''$^4$) and L'' are neutral donor ligands. In some embodiments, L" may also be a phosphine having a formula PHR"⁵R"⁶. In such embodiments, the Group 8 metal complex may be represented by the formula (I):

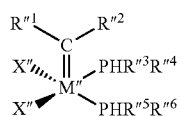

wherein

M" is a Group 8 metal (preferably M is ruthenium or osmium, preferably ruthenium);

each X" is independently an anionic ligand (preferably selected from the group consisting of halides, alkoxides, aryloxides, and alkyl sulfonates, preferably a halide, preferably chloride);

$R'''^1$ and $R'''^2$ are independently selected from the group consisting of hydrogen, a $C_1$ to $C_{30}$ hydrocarbyl, and a $C_1$ to $C_{30}$ substituted hydrocarbyl (preferably $R'''^1$ and $R'''^2$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl); and $R'''^3$, $R'''^4$, $R'''^5$, and $R'''^6$ are independently selected from the group consisting of hydrogen, $C_1$ to $C_{12}$ hydrocarbyl groups, substituted $C_1$ to $C_{12}$ hydrocarbyl groups, and halides (preferably $R'''^3$, $R'''^4$, $R'''^5$, and $R'''^6$ are independently selected from the group consisting of methyl, ethyl, propyl, isopropyl, butyl, tert-butyl, sec-butyl, pentyl, cyclopentyl, hexyl, cyclohexyl, heptyl, octyl, cyclooctyl, and substituted analogs and isomers thereof, preferably selected from the group consisting of tert-butyl, sec-butyl, cyclohexyl, and cyclooctyl).

With respect to embodiments where L" is a phosphine having a formula PHR"⁵R"⁶, in particular embodiments, at least one phosphine ligand is a secondary phosphine ligand. In such embodiments, where at least one of the neutral donor ligands is a secondary phosphine ligand, $R'''^3$ and $R'''^4$ or $R'''^5$ and $R'''^6$ are selected from the group consisting of $C_1$ to $C_{12}$ hydrocarbyl groups, substituted $C_1$ to $C_{12}$ hydrocarbyl groups, and halides. In particular embodiments, both donor ligands are secondary phosphine ligands and $R'''^3$, $R'''^4$, $R'''^5$, and $R'''^6$ are selected from the group consisting of $C_1$ to $C_{12}$ hydrocarbyl groups, substituted $C_1$ to $C_{12}$ hydrocarbyl groups, and halides.

With respect to embodiments where L" is a phosphine having a formula PHR"⁵R"⁶, in particular embodiments, at least one donor ligand is a primary phosphine ligand. In such embodiments where at least one of the phosphine ligands is a primary phosphine ligand, one of $R'''^3$ and $R'''^4$ or one of $R'''^5$ and $R'''^6$ is selected from the group consisting of $C_1$ to $C_{12}$ hydrocarbyl groups, substituted $C_1$ to $C_{12}$ hydrocarbyl groups, and halides. In particular embodiments, both donor ligands are primary phosphine ligands and one of $R'''^3$ and $R'''^4$ and one of $R'''^5$ and $R'''^6$ is selected from the group consisting of $C_1$ to $C_{12}$ hydrocarbyl groups, substituted $C_1$ to $C_{12}$ hydrocarbyl groups, and halides.

In some embodiments, $R'''^3$ and $R'''^4$ form a ring. With respect to embodiments where L" is a phosphine having a formula PHR"⁵R"⁶, in particular embodiments, $R'''^5$ and $R'''^6$ form a ring. In yet other embodiments, $R'''^3$ and $R'''^4$ form a ring and $R'''^5$ and $R'''^6$ form a ring. In other embodiments, $R'''^3$ and at least one of $R'''^5$ and $R'''^6$ may form a ring, thereby forming a chelating phosphine ligand. In other embodiments, $R'''^4$ and at least one of $R'''^5$ and $R'''^6$ may form a ring, thereby forming a chelating phosphine ligand.

In particular embodiments, the Group 8 metal complex is selected from:

[(HP(tert-butyl)₂)₂Ru(C₅H₈)Cl₂],
[(H₂P(tert-butyl))₂Ru(C₅H₈)Cl₂],
[(HP(cyclohexyl)₂)₂Ru(C₅H₈)Cl₂],
[(H₂P(cyclohexyl))₂Ru(C₅H₈)Cl₂],
[(HP(cyclopentyl)₂)₂Ru(C₅H₈)Cl₂],
[(H₂P(cyclopentyl))₂Ru(C₅H₈)Cl₂],
[(HP(n-butyl)₂)₂Ru(C₅H₈)Cl₂],
[(H₂P(n-butyl))₂Ru(C₅H₈)Cl₂],
[(HP(sec-butyl)₂)₂Ru(C₅H₈)Cl₂],
[(H₂P(sec-butyl))₂Ru(C₅H₈)Cl₂], and
fluoride and bromide derivatives thereof (preferably, wherein the Cl₂ in the above list is replaced with F₂, Br₂, ClF, ClBr, or FBr).

Support Materials

In embodiments herein, the catalyst system to make the functionalized DCPD polymer may comprise an inert support material. Preferably, the supported material is a porous support material, for example, talc, and inorganic oxides. Other support materials include zeolites, clays, organoclays, polymers, or any other organic or inorganic support material and the like, or mixtures thereof.

Preferably, the support material is an inorganic oxide in a finely divided form. Suitable inorganic oxide materials for use in metallocene catalyst systems herein include Groups 2, 4, 13, and 14 metal oxides such as silica, alumina and mixtures thereof. Other inorganic oxides that may be employed either alone or in combination with the silica, or alumina are magnesia, titania, zirconia, and the like. Other suitable support materials, however, can be employed, for example, finely divided functionalized polyolefins such as finely divided polyethylene. Particularly useful supports include magnesia, titania, zirconia, montmorillonite, phyllosilicate, zeolites, talc, clays, and the like. Also, combinations of these support materials may be used, for example, silica-chromium, silica-alumina, silica-titania and the like. Preferred support materials include Al₂O₃, ZrO₂, SiO₂, and combinations thereof, more preferably SiO₂, Al₂O₃, or SiO₂/Al₂O₃.

It is preferred that the support material, most preferably an inorganic oxide, has a surface area in the range of from about 10 to about 700 m²/g, pore volume in the range of from about 0.1 to about 4.0 cc/g and average particle size in the range of from about 5 to about 500 μm. More preferably, the surface area of the support material is in the range of from about 50 to about 500 m²/g, pore volume of from about 0.5 to about 3.5 cc/g and average particle size of from about 10 to about 200 μm. Most preferably, the surface area of the support material is in the range is from about 100 to about 400 m²/g, pore volume from about 0.8 to about 3.0 cc/g and average particle size is from about 5 to about 100 μm. The average pore size of the support material useful in the invention is in the range of from 10 to 1000 Å, preferably 50 to about 500 Å, and most preferably 75 to about 350 Å. In some embodiments, the support material is a high surface area, amorphous silica (surface area=300 m²/gm; pore volume of 1.65 cm³/gm), examples of which are marketed under the tradenames of DAVISON 952 or DAVISON 955 by the Davison Chemical Division of W.R. Grace and Company. In other embodiments, DAVISON 948 is used.

The support material should be dry, that is, free of absorbed water. Drying of the support material can be effected by heating or calcining at about 100° C. to about 1000° C., preferably at least about 600° C. When the support material is silica, it is heated to at least 200° C., preferably about 200° C. to about 850° C., and most preferably at about 600° C.; and for a time of about 1 minute to about 100 hours, from about 12 hours to about 72 hours, or from about 24 hours to about 60 hours.

Methods of Making the Supported Catalyst Systems

The support material is slurried in a non-polar solvent and the resulting slurry is contacted with a solution of catalyst. The slurry of the support material in the solvent is prepared by introducing the support material into the solvent, and heating the mixture to about 0° C. to about 70° C., preferably to about 25° C. to about 60° C., preferably at 25° C. Contact times typically range from about 0.5 hours to about 24 hours, from about 0.5 hours to about 8 hours, or from about 0.5 hours to about 4 hours.

Suitable non-polar solvents are materials in which all of the reactants used herein, i.e., the activator, and the metallocene compound, are at least partially soluble and which are liquid at reaction temperatures. Preferred non-polar solvents are alkanes, such as isopentane, hexane, n-heptane, octane, nonane, and decane, although a variety of other materials including cycloalkanes, such as cyclohexane, aromatics, such as benzene, toluene and ethylbenzene, may also be employed.

DCPD Polymers

Preferred cyclopentadiene-based hydrocarbon resins for use as DCPD polymers in the invention include thermally polymerized hydrocarbon tackifier resin which is a copolymer of a feedstock comprising a mixture of a vinyl aromatic stream containing styrene, alkyl substituted derivatives of styrene (such as alpha-methyl styrene), indene and alkyl substituted derivatives of indene; a cyclodiene stream comprising monomers, dimers and codimers of cyclopentadiene and alkyl substituted derivatives of cyclopentadiene; and optionally a $C_4$-$C_5$ acyclic diene stream.

In particular, the present invention can utilize a thermally polymerized, hydrocarbon tackifier resin which is a copolymer of a feedstock which comprises 100 parts of a vinyl aromatic stream containing styrene and indene and alkyl substituted derivatives thereof; 10 to 1000 parts of a cyclodiene stream comprising monomers, dimers and codimers of cyclopentadiene and alkyl substituted derivatives of cyclopentadiene; and optionally 0 to 100 parts of a $C_4$-$C_5$ acyclic diene stream.

A typical vinyl aromatic stream used to produce resins useful in the present invention has a composition of 7 wt % styrene, 30 wt % alkyl substituted derivatives of styrene, 13 wt % indene, 9 wt % alkyl substituted derivatives of indene, and 41 wt % non-reactive aromatic components. The vinyl aromatic stream is obtained by steam cracking petroleum refinery streams and separating the fraction boiling in the range of 135° C. to 220° C. by fractional distillation.

A useful cyclodiene stream to make resins useful in the present invention comprises monomers, dimers and codimers of cyclopentadiene, and alkyl substituted derivatives of cyclopentadiene. This component of the feedstock is obtained by steam cracking petroleum refinery streams, separating a $C_5$-$C_6$ fraction boiling in the range of 30° C. to 80° C., heat soaking to dimerize and codimerize the cyclopentadiene and alkyl substituted cyclopentadienes and distilling to remove unreacted $C_5$-$C_6$ components.

Two components of the feedstock, the vinyl aromatic stream and the cyclodiene stream, are combined in a mixture having about 100 parts vinyl aromatic components and 10 to 1000 parts cyclodiene component. A preferred mixture of vinyl aromatic and cyclodiene components is 100 parts vinyl aromatic component to 50-80 parts cyclodiene component, preferably 60-70 parts, preferably about 66 parts. The feed mixture may also include a non-reactive polymerization diluent, such as toluene. The feed mixture may optionally contain up to 100 parts of an acyclic diene component. The resin feedstock mixture may be thermally polymerized at a temperature between 160° C. and 320° C., preferably from 250° C. to 290° C., for a period of 10 to 500 minutes, preferably 60-180 minutes. The resin solution that results from the thermal polymerization is stripped of solvent and unreacted monomers by heating to a temperature of from 150° C. to 300° C., with or without the injection of steam. The resultant resin typically exhibits the following properties: softening point from 80° C. to 200° C., weight average molecular weight (Mw) by GPC from 300-1000, number average molecular weight (Mn) from 100-500, and dark color.

The resin, or final product, is then typically hydrogenated to a level where the resultant resin contains about 1% to 20% aromatic hydrogens as measured by $^1$H-NMR. Hydrogenation may be by any means known in the art, such as is shown in U.S. Pat. No. 5,820,749, and in European Patent Nos. EP 0 516 733 and EP 0 046 634. Following hydrogenation, the resin can be stripped to softening points ranging from 70° C. to 200° C., preferably 70° C. to 130° C. The resultant hydrogenated resins preferably exhibit the following properties: weight average molecular weight (Mw) by GPC from 300-1000 g/mol, number average molecular weight (Mn) from 100-500 g/mol, a Mw/Mn ratio of about 2, and a Saybolt color of 23-30.

The presence of the olefinic diluent allows the hydrogenation reactor to achieve a desirable rapid increase in temperature early in the hydrogenation run. The rapid increase in temperature results from the rapid exothermic hydrogenation reaction of converting the olefinic diluent to a paraffin. The amount of olefinic diluent used should be such that the exothermic reaction increases the hydrogenation reactor temperature by 40° C. to 140° C. Preferably, the temperature increase should be in the range of 80° C. to 110° C. The desired peak temperature in the hydrogenation reactor should be in the range of 280° C. to 320° C. when the olefinic diluent is used in a hydrogenation reactor having an inlet temperature ranging from 180° C. to –240° C. The olefinic diluent may be any olefin, preferably a mono-olefin, having 3 to 20 carbon atoms, preferably 5 to 12 carbon atoms. The solvent diluent may be any saturated hydrocarbon solvent, preferably aliphatic or cycloaliphatic in nature. The solution that results from the hydrogenation process is stripped of solvent and oligomeric material by heating to temperatures of from 150° C. to 350° C., with or without the injection of steam.

Metathesis products prepared herein can further be hydrogenated after completion or during reaction conditions.

The hydrogenation may be achieved in the presence of any of the known catalysts commonly used for hydrogenating petroleum resins. The catalysts which may be used in the hydrogenation step include the Group 10 metals such as nickel, palladium, ruthenium, rhodium, cobalt and platinum, the Group 6 metals such as tungsten, chromium and molybdenum, and the Group 11 metals such as rhenium, manganese and copper. These metals may be used singularly or in a combination of two or more metals, in the metallic form or in an activated form, and may be used directly or carried on a solid support such as alumina or silica-alumina. A preferred catalyst is one comprising sulfided nickel-tungsten on a gamma-alumina support having a fresh catalyst surface area ranging from 120 to 300 m 2/g and containing from 2% to 10% by weight nickel and from 10% to 25% by weight tungsten as described in U.S. Pat. No. 4,629,766. The hydrogenation is carried out with a hydrogen pressure of 20-300 atmospheres, preferably 150-250 atmospheres.

Examples of hydrocarbon resins useful in this invention include Escorez® 8000 series resins sold by ExxonMobil Chemical Company in Baton Rouge, La. Further examples of hydrocarbon resins useful in this invention include Arkon® series resins sold by Arakawa Europe in Germany. Yet more examples of hydrocarbon resins useful in this invention include the Eastotac® series of resins sold by Eastman Chemical Company in Longview, Tex.

In another embodiment, the dicyclopentadiene monomer and/or the DCPD polymer used herein preferably has a low sulfur content. For example the DCPD may have less than 300 ppm sulfur, preferably less than 250 ppm sulfur, preferably less than 100 ppm sulfur, preferably less than 50 ppm sulfur, preferably less than 40 ppm sulfur, preferably less than 30 ppm sulfur, preferably less than 20 ppm sulfur.

In a particularly useful embodiment, the DCPD monomer that is used to make the DCPD polymer used herein comprises less than 300 ppm sulfur, preferably less than 250 ppm sulfur, preferably less than 100 ppm sulfur, preferably less than 50 ppm sulfur, preferably less than 40 ppm sulfur, preferably less than 30 ppm sulfur, preferably less than 20 ppm sulfur.

Hot Melt Adhesives

In a particular embodiment, the compositions of this invention can be used in a hot melt adhesive composition. Hot melt adhesives exist as a solid at ambient temperature and can be converted into a tacky liquid by the application of heat. Hot melt adhesives are typically applied to a substrate in molten form.

The adhesive composition includes the inventive polymer described herein. The polymer may be functionalized with maleic acid or maleic anhydride. Additional components may be combined with the polymers or formulations of the polymers to form the adhesive composition.

In one aspect, the adhesive composition can include one or more tackifiers. The tackifiers can include aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin acids, hydrogenated rosin esters, derivatives thereof, and combinations thereof, for example. The adhesive composition may include from 0 to 90 percent by weight of the one or more tackifiers. More preferably, the adhesive composition includes 5 to 60 percent by weight of the one or more tackifiers, preferably 10 to 40 percent by weight, preferably 10 to 20 percent by weight.

In another aspect, the adhesive composition can include one or more waxes, such as polar waxes, non-polar waxes, Fischer-Tropsch waxes, oxidized Fischer-Tropsch waxes, hydroxystearamide waxes, functionalized waxes, polypropylene waxes, polyethylene waxes, wax modifiers, and combinations thereof, for example. The adhesive composition may include from 0 to 75 percent by weight the one or more waxes. More preferably, the adhesive composition includes 1 to 15 percent by weight of the one or more waxes.

In yet another aspect, the adhesive composition can include 60 percent by weight or less, 30 percent by weight or less, 20 percent by weight or less, 15 percent by weight or less, 10 percent by weight or less or 5 percent by weight of one or more additives. The one or more additives can include plasticizers, oils, stabilizers, antioxidants, pigments, dyestuffs, antiblock additives, polymeric additives, defoamers, preservatives, thickeners, rheology modifiers, humectants, fillers, solvents, nucleating agents, surfactants, chelating agents, gelling agents, processing aids, cross-linking agents, neutralizing agents, flame retardants, fluorescing agents, compatibilizers, antimicrobial agents, and water, for example.

Exemplary oils may include aliphatic naphthenic oils, white oils, and combinations thereof, for example. The phthalates may include di-iso-undecyl phthalate (DIUP), di-iso-nonylphthalate (DINP), dioctylphthalates (DOP), combinations thereof, or derivatives thereof. Exemplary polymeric additives include homo poly-alpha-olefins, copolymers of alpha-olefins, copolymers and terpolymers of diolefins, elastomers, polyesters, block copolymers including diblocks and triblocks, ester polymers, alkyl acrylate polymers, and acrylate polymers. Exemplary plasticizers may include mineral oils, polybutenes, phthalates, and combinations thereof.

Blends of Functionalized Polyolefins

In some embodiments, the functionalized (and optionally derivitized) DCPD polymer produced by this invention may be blended with of one or more other polymers, including but not limited to, thermoplastic polymer(s) and/or elastomer(s). Typically the functionalized DCPD is present at from 0.1 wt % to 99 wt % (typically 1 wt % to 60 wt %, preferably 5 wt % to 40 wt %, and ideally about 10 wt % to about 45 wt %) based upon the weight of the blend and the other polymers are present at 99.9 wt % to 1 wt % (typically 99 wt % to 40 wt %, preferably 95 wt % to 60 wt %, preferably 90 wt % to 65 wt %).

By thermoplastic polymer(s) is meant a polymer that can be melted by heat and then cooled without appreciable change in properties. Thermoplastic polymers typically include, but are not limited to, polyolefins, polyamides, polyesters, polycarbonates, polysulfones, polyacetals, polylactones, acrylonitrile-butadiene-styrene resins, polyphenylene oxide, polyphenylene sulfide, styrene-acrylonitrile resins, styrene maleic anhydride, polyimides, aromatic polyketones, or mixtures of two or more of the above. Preferred polyolefins include, but are not limited to, polymers comprising one or more linear, branched or cyclic $C_2$ to $C_{40}$ olefins, preferably polymers comprising propylene copolymerized with one or more $C_3$ to $C_{40}$ olefins, preferably a $C_3$ to $C_{20}$ alpha-olefin, more preferably $C_3$ to $C_{10}$ alpha-olefins. More preferred polyolefins include, but are not limited to, polymers comprising ethylene including but not limited to ethylene copolymerized with a $C_3$ to $C_{40}$ olefin, preferably a $C_3$ to $C_{20}$ alpha-olefin, more preferably propylene and/or butene.

By elastomers is meant all natural and synthetic rubbers, including those defined in ASTM D1566. Examples of preferred elastomers include, but are not limited to, ethylene propylene rubber, ethylene propylene diene monomer rubber, styrenic block copolymer rubbers (including SI, SIS, SB, SBS, SIBS, and the like, where S=styrene, I=isoprene, and B=butadiene), butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, polybutadiene rubber (both cis and trans).

In another embodiment, the functionalized (and optionally derivitized) polyolefins produced herein may further be combined with one or more of polybutene, ethylene vinyl acetate, low density polyethylene (density 0.915 to less than 0.935 g/cm$^3$) linear low density polyethylene, ultra low density polyethylene (density 0.86 to less than 0.90 g/cm³), very low density polyethylene (density 0.90 to less than 0.915 g/cm³), medium density polyethylene (density 0.935 to less than 0.945 g/cm³), high density polyethylene (density 0.945 to 0.98 g/cm³), ethylene vinyl acetate, ethylene methyl acrylate, copolymers of acrylic acid, polymethylmethacrylate or any other polymers polymerizable by a high-pressure free radical process, polyvinylchloride, polybutene-1, isotactic polybutene, ABS resins, ethylene-propylene rubber (EPR), vulcanized EPR, EPDM, block copolymer, styrenic block copolymers, polyamides, polycarbonates, PET resins, crosslinked polyethylene, copolymers of ethylene and vinyl alcohol (EVOH), polymers of aromatic monomers such as polystyrene, poly-1 esters, polyacetal, polyvinylidine fluoride, polyethylene glycols and/or polyisobutylene. Preferred polymers include those available from ExxonMobil Chemical Company in Baytown, Tex. under the tradenames EXCEED™ and EXACT™.

Tackifiers may be blended with the functionalized (and optionally derivitized) polyolefins produced herein and/or with blends of the functionalized (and optionally derivitized) polyolefins produced by this inventions (as described above). Examples of useful tackifiers include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, and hydrogenated rosin esters. In some embodiments the tackifier is hydrogenated. In some embodiments the tackifier has a softening point (Ring and Ball, as measured by ASTM E-28) of 80° C. to 140° C., preferably 100° C. to 130° C. The tackifier, if present, is typically present at about 1 wt % to about 50 wt %, based upon the weight of the blend, more preferably 10 wt % to 40 wt %, even more preferably 20 wt % to 40 wt %.

In another embodiment, the functionalized (and optionally derivitized) polyolefins of this invention, and/or blends thereof, further comprise typical additives known in the art such as fillers, cavitating agents, antioxidants, surfactants, adjuvants, plasticizers, block, antiblock, color masterbatches, pigments, dyes, processing aids, UV stabilizers, neutralizers, lubricants, waxes, and/or nucleating agents. The additives may be present in the typically effective amounts well known in the art, such as 0.001 wt % to 10 wt %. Preferred fillers, cavitating agents and/or nucleating agents include titanium dioxide, calcium carbonate, barium sulfate, silica, silicon dioxide, carbon black, sand, glass beads, mineral aggregates, talc, clay and the like. Preferred antioxidants include phenolic antioxidants, such as Irganox 1010, Irganox, 1076 both available from Ciba-Geigy. Preferred oils include paraffinic or naphthenic oils such as Primol 352, or Primol 876 available from ExxonMobil Chemical France, S.A. in Paris, France. More preferred oils include aliphatic naphthenic oils, white oils, or the like.

In a particularly preferred embodiment, the functionalized (and optionally derivitized) polyolefins produced herein are combined with polymers (elastomeric and/or thermoplastic) having functional groups such as unsaturated molecules-vinyl bonds, ketones or aldehydes under conditions such that they react. Reaction may be confirmed by an at least 20% (preferably at least 50%, preferably at least 100%) increase in Mw as compared to the Mw of the functionalized polyolefin prior to reaction. Such reaction conditions may be increased heat (for example, above the Tm of the functionalized polyolefin), increased shear (such as from a reactive extruder), presence or absence of solvent. Conditions useful for reaction include temperatures from 150° C. to 240° C. and where the components can be added to a stream comprising polymer and other species via a side arm extruder, gravimetric feeder, or liquids pump. Useful polymers having functional groups that can be reacted with the functionalized polyolefins produced herein include polyesters, polyvinyl acetates, nylons (polyamides), polybutadiene, nitrile rubber, hydroxylated nitrile rubber. In some embodiments, the functionalized (and optionally derivitized) polyolefin of this invention may be blended with up to 99 wt % (preferably up to 25 wt %, preferably up to 20 wt %, preferably up to 15 wt %, preferably up to 10 wt %, preferably up to 5 wt %), based upon the weight of the composition, of one or more additional polymers. Suitable polymers include:

PM1) Polyethylenes, including (but not limited to):
Copolymers of ethylene and one or more polar monomers, preferably selected from vinyl acetate, methyl acrylate, n-butyl acrylate, acrylic acid, and vinyl alcohol (i.e., EVA, EMA, EnBA, EAA, and EVOH); ethylene homopolymers and copolymers synthesized using a high-pressure free radical process, including LDPE; copolymers of ethylene and $C_3$ to $C_{40}$ olefins (preferably propylene and/or butene) with a density of greater than 0.91 g/cm³ to less than 0.94 g/cm³), including LLDPE; and high density PE (0.94 to 0.98 g/cm³).

PM2) Polybutene-1 and copolymers of polybutene-1 with ethylene and/or propylene.

PM3) Non-EP Rubber Elastomers, including (but not limited to):
Polyisobutylene, butyl rubber, halobutyl rubber, copolymers of isobutylene and para-alkylstyrene, halogenated copolymers of isobutylene and para-alkylstyrene, natural rubber, polyisoprene, copolymers of butadiene with acrylonitrile, polychloroprene, alkyl acrylate rubber, chlorinated isoprene rubber, acrylonitrile chlorinated isoprene rubber, and polybutadiene rubber (both cis and trans).

PM4) Low-crystallinity propylene/olefin copolymers, preferably random copolymers, comprising:
i) at least 70 wt % propylene;
ii) 5 wt % to 30 wt % (preferably 5 wt % to 20 wt %) of comonomer selected from ethylene and $C_4$ to $C_{12}$ olefins (preferably selected from ethylene, butene, and hexene; preferably ethylene);
preferably made using a metallocene-type catalyst; and having one or more of the following properties:
a) Mw of 20 to 5,000 kg/mol (preferably 30 to 2,000 kg/mol, preferably 40 to 1,000 kg/mol, preferably 50 to 500 kg/mol, preferably 60 to 400 kg/mol); and/or
b) molecular weight distribution index (Mw/Mn) of 1.5 to 10 (preferably 1.7 to 5, preferably 1.8 to 3); and/or
c) GPC-determined g' index value of 0.9 or greater (preferably 0.95 or greater, preferably 0.99 or greater); and/or
d) density of 0.85 to about 0.90 g/cm³ (preferably 0.855 to 0.89 g/cm³, preferably 0.86 to about 0.88 g/cm³); and/or
e) melt flow rate (MFR) of at least 0.2 dg/min (preferably 1-500 dg/min, preferably 2-300 dg/min); and/or
f) heat of fusion (Hf) of 0.5 J/g or more (preferably 1 J/g or more, preferably 2.5 J/g or more, preferably 5 J/g or more) but less than or equal to 75 J/g (preferably less than or equal to 50 J/g, preferably less than or equal to 35 J/g, preferably less than or equal to 25 J/g); and/or g) DSC-determined crystallinity of from 1 wt % to 30 wt % (preferably 2 wt % to 25 wt %, preferably 2 wt % to 20 wt %, preferably 3 wt % to 15 wt %); and/or h) a single broad melting transition with a peak melting point of 25° C. to about 105° C. (preferably 25° C. to 85° C., preferably 30° C. to 70° C., preferably 30° C. to 60° C.), where the highest peak considered the melting point; and/or i) crystallization temperature (Tc) of 90° C. or less (preferably 60° C. or less); and/or j) greater than 80% of the propylene residues (exclusive of any other monomer such as ethylene) arranged as 1,2 insertions with the same stereochemical orientation of the pendant methyl groups, either meso or racemic, as determined by $^{13}$C NMR; and/or k) $^{13}$C NMR-determined propylene tacticity index of more than 1; and/or l) $^{13}$C NMR-determined mm triad tacticity index of 75% or greater (preferably 80% or greater, preferably 82% or greater, preferably 85% or greater, preferably 90% or greater). Useful low-crystallinity propylene/olefin copolymers are available from ExxonMobil Chemical; suitable examples include Vistamaxx™ 6100, Vistamaxx™ 6200 and Vistamaxx™ 3000. Other useful low-crystallinity propylene/olefin copolymers are described in WO 03/040095, WO 03/040201, WO 03/040233, and WO 03/040442, all to Dow Chemical, which disclose propylene-ethylene copolymers made with non-metallocene catalyst compounds. Still other useful low-crystallinity propylene/olefin copolymers are described in U.S. Pat. No. 5,504,172 to Mitsui Petrochemical. Preferred low-crystallinity propylene/olefin copolymers are described in U.S. Published Application No. 2002/0004575 to ExxonMobil Chemical.

PM5) Propylene oligomers suitable for adhesive applications, such as those described in WO 2004/046214, particularly those at pages 8 to 23.

PM6) Olefin block copolymers, including those described in WO 2005/090425, WO 2005/090426, and WO 2005/090427.

PM7) Polyolefins that have been post-reactor functionalized with maleic anhydride (so-called maleated polyolefins), including maleated ethylene polymers, maleated EP Rubbers, and maleated propylene polymers. Preferably, the amount of free acid groups present in the maleated polyolefin is less than about 1000 ppm (preferably less than about 500 ppm, preferably less than about 100 ppm), and the amount of phosphite present in the maleated polyolefin is less than 100 ppm.

PM8) Styrenic Block Copolymers (SBCs), including (but not limited to):

Unhydrogenated SBCs such as SI, SIS, SB, SBS, SIBS and the like, where S=styrene, I=isobutylene, and B=butadiene; and hydrogenated SBCs, such as SEBS, where EB=ethylene/butene.

PM9) Engineering Thermoplastics, including (but are not limited to):

Polycarbonates, such as poly(bisphenol-a carbonate); polyamide resins, such as nylon 6 (N6), nylon 66 (N66), nylon 46 (N46), nylon 11 (N11), nylon 12 (N12), nylon 610 (N610), nylon 612 (N612), nylon 6/66 copolymer (N6/66), nylon 6/66/610 (N6/66/610), nylon MXD6 (MXD6), nylon 6T (N6T), nylon 6/6T copolymer, nylon 66/PP copolymer, and nylon 66/PPS copolymer; polyester resins, such as polybutylene terephthalate (PBT), polyethylene terephthalate (PET), polyethylene isophthalate (PEI), PET/PEI copolymer, polyacrylate (PAR), polybutylene naphthalate (PBN), liquid crystal polyester, polyoxalkylene diimide diacid/polybutyrate terephthalate copolymer, and other aromatic polyesters; nitrile resins, such as polyacrylonitrile (PAN), polymethacrylonitrile, styrene-acrylonitrile copolymers (SAN), methacrylonitrile-styrene copolymers, and methacrylonitrile-styrene-butadiene copolymers; acrylate resins, such as polymethyl methacrylate and polyethylacrylate; polyvinyl acetate (PVAc); polyvinyl alcohol (PVA); chloride resins, such as polyvinylidene chloride (PVDC), and polyvinyl chloride (PVC); fluoride resins, such as polyvinylidene fluoride (PVDF), polyvinyl fluoride (PVF), polychlorofluoroethylene (PCFE), and polytetrafluoroethylene (PTFE); cellulose resins, such as cellulose acetate and cellulose acetate butyrate; polyimide resins, including aromatic polyimides; polysulfones; polyacetals; polylactones; polyketones, including aromatic polyketones; polyphenylene oxide; polyphenylene sulfide; styrene resins, including polystyrene, styrene-maleic anhydride copolymers, and acrylonitrile-butadiene-styrene resin.

PM10) EP Rubbers, including copolymers of ethylene and propylene, and optionally one or more diene monomer(s), where the ethylene content is from 35 mol % to 85 mol %, the total diene content is 0 mol % to 5 mol %, and the balance is propylene with a minimum propylene content of 15 mol %. Typically, the EP Rubbers have a density of less than 0.86 g/cc.

Applications

The functionalized DCPD polymers of this invention (and blends thereof as described above) may be used in any known thermoplastic or elastomer application. Examples include uses in molded parts, films, tapes, sheets, tubing, hose, sheeting, wire and cable coating, adhesives, shoe soles, bumpers, gaskets, bellows, films, fibers, elastic fibers, nonwovens, spunbonds, corrosion protection coatings and sealants. The functionalized DCPD polymers of the invention can also be used as protective films, such as those described in U.S. Pat. No. 7,323,239 and also as rosin tackifiers and as heat sealable films such as those described in U.S. Pat. No. 4,921,749, the contents of which are incorporated herein in their entirety for all purposes.

In another embodiment the functionalized DCPD polymers can be used as a compatibilizer for particulate materials, such as carbon black, silica, glass, etc. or other high surface tension materials when the material is being blended into another polymer (such as polystyrene, polyethylene, polypropylene, butyl rubber, SBR, natural rubber, and other polymers named as PM1 to PM10 above).

EXPERIMENTAL

Product Characterization

Products were characterized by $^1$H NMR and $^{13}$C NMR as follows:

$^1$H NMR

Unless otherwise stated, $^1$H NMR data was collected at either 25° C. or 120° C. (for purposes of the claims, 120° C. shall be used) in a 5 mm probe using a spectrometer with a $^1$H frequency of at least 400 MHz. Data was recorded using a maximum pulse width of 45°, 8 seconds between pulses and signal averaging 32 transients.

$^{13}$C NMR

Unless otherwise stated, $^{13}$C NMR data was collected at 120° C. using a spectrometer with a $^{13}$C frequency of at least 100 MHz. A 90 degree pulse, an acquisition time adjusted to give a digital resolution between 0.1 and 0.12 Hz, at least a 10 second pulse acquisition delay time with continuous broadband proton decoupling using swept square wave modulation without gating was employed during the entire acquisition period. The spectra were acquired with time averaging to provide a signal to noise level adequate to measure the signals of interest. Samples were dissolved in tetrachloroethane-$d_2$ (TCE) at concentrations between 10 to 40 wt % prior to being inserted into the spectrometer magnet.

Prior to data analysis spectra were referenced by setting the chemical shift of the TCE solvent signal to 74.39 ppm.

Mass Spec Analysis of Products from Examples 1-8

Experimental

Experiments were conducted on a twelve-tesla Bruker Apex Qe Fourier Transform Ion Cyclotron Resonance mass spectrometry (FTICR) mass spectrometer (Bruker Daltonics Inc., Billerica, Mass., USA). With the FTICR mass spectrometer, the mass to charge ratio of ions is accurately measured by obtaining the cyclotron frequency of the excited ions in the FTICR cell. The highest mass resolution of FT-ICR is about one million to provide accurate mass measurements, and high mass accuracy can be obtained with an error of less than 1 ppm.

Atmospheric pressure photoionization (APPI) was used on FTICR to efficiently ionize the non-polar polymerized DCPD molecules by forming radical cations. The APPI source is equipped with a Krypton discharge Lamp at 10.6 eV for ionization. APPI is a soft ionization technique which does not introduce fragmentation, so that all the observed peaks are corresponding to parent ions.

Samples were first dissolved in toluene at concentration of 1000 ppm. The sample solution was introduced into the APPI source at a flow rate of 120 μL/h. The following parameters were used: desolvation temperature at 450° C.; dry gas temperature at 200° C.; dry gas flow at 5 L/min; nebulizing gas at 4 L/min. Each of the mass spectra was obtained by summing up 48 scans. Bruker Data Analysis (DA) software was used to process the data.

All molecular weights are g/mol unless otherwise noted.

Examples

The ruthenium catalyst used in Examples 1-8 is 1,3-Bis(2, 4,6-trimethylphenyl)-4,5-dihydro imidazol-2-ylidene[2-(i-prop oxy)-5-(N,N-dimethylamino sulfonyl)phenyl]methyleneruthenium(II)dichloride.

Example 1

Preparation of Resin A

A 5 gallon batch reactor was charged with DCPD monomer (45 lb, hydrocarbon resin grade DCPD obtained from Texmark CXI, having less than 20 ppm sulfur), and dissolved in toluene. The reactor was sealed, and the pressure was increased to 50 psi using $N_2$. Stirring was initiated, and the reactor was heated to 272° C. After 1.5 hours at 272° C., the reactor was cooled to ambient temperature and the product was removed. 600 g of the isolated mixture was transferred into a glass reactor, and volatiles were removed under a flow of steam.

Example 2

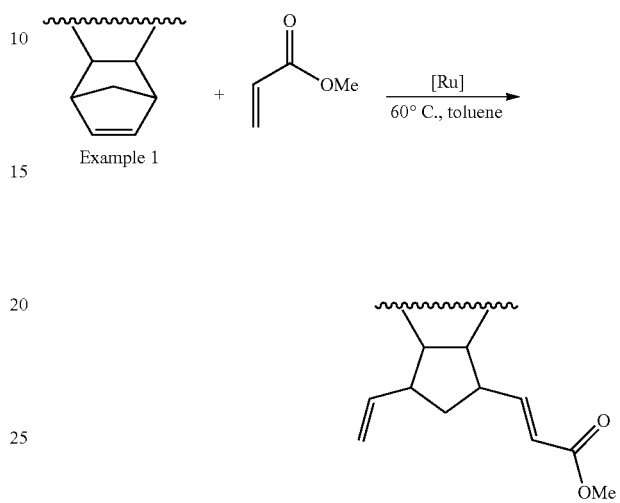

In the glovebox a 20 mL vial was charged with Resin A (0.2 g), toluene (2.0 mL), and a stirbar. With stirring, the solution was heated to 60° C. After all of Resin A had dissolved, methyl acrylate (55 mg) was added, followed by the ruthenium catalyst (12 mg). After stirring at 60° C. for 18 h, the mixture was cooled to 25° C., and volatiles were removed under a flow of nitrogen.

Example 3

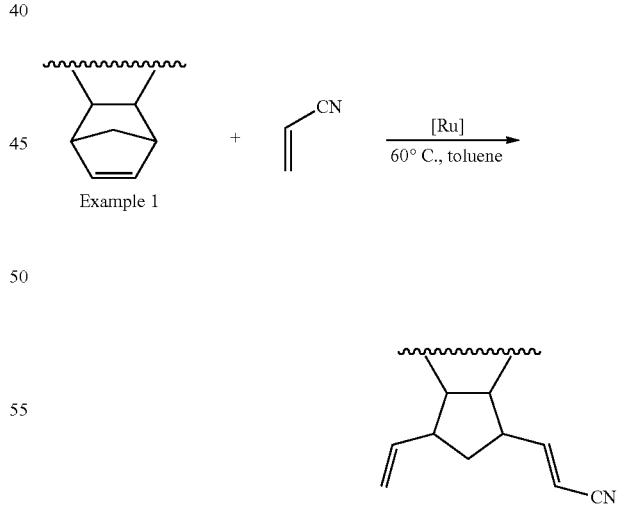

In the glovebox a 20 mL vial was charged with Resin A (0.2 g), toluene (2.0 mL), and a stirbar. With stirring, the solution was heated to 60° C. After all of Resin A had dissolved, acrylonitrile (34 mg) was added, followed by the ruthenium catalyst (12 mg). After stirring at 60° C. for 18 h, the mixture was cooled to 25° C., and volatiles were removed under a flow of nitrogen.

Example 4

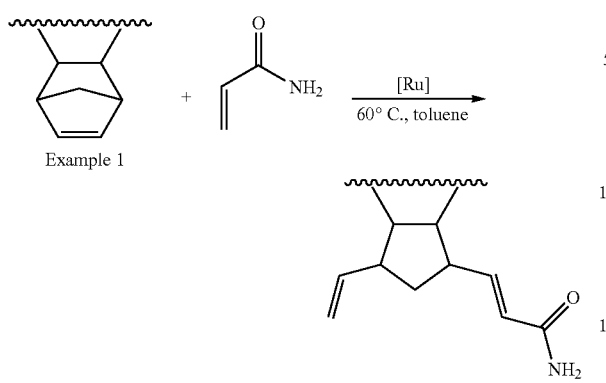

In the glovebox a 20 mL vial was charged with Resin A (0.2 g), toluene (2.0 mL), and a stirbar. With stirring, the solution was heated to 60° C. After all of Resin A had dissolved, acrylamide (46 mg) was added, followed by the ruthenium catalyst (12 mg). After stirring at 60° C. for 18 h, the mixture was cooled to 25° C., and volatiles were removed under a flow of nitrogen.

Example 5

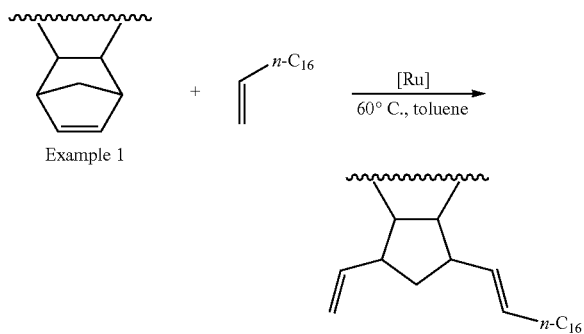

In the glovebox a 20 mL vial was charged with Resin A (0.6 g), toluene (6.0 mL), and a stirbar. With stirring, the solution was heated to 60° C. After all of Resin A had dissolved, 1-octene (480 mg) was added, followed by the ruthenium catalyst (36 mg). After stirring at 60° C. for 18 h, the mixture was cooled to 25° C., and volatiles were removed under a flow of nitrogen. The vial was removed from the glovebox, and the residue was triturated with MeOH. The precipitate that formed was isolated by filtration, washed with additional MeOH, and dried under reduced pressure.

Example 6

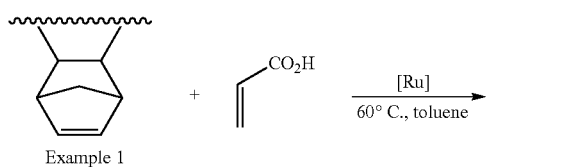

No Incorporation of Acid Groups

In the glovebox a 20 mL vial was charged with Resin A (0.6 g), toluene (6.0 mL), and a stirbar. With stirring, the solution was heated to 60° C. After all of Resin A had dissolved, acrylic acid (140 mg) was added, followed by the ruthenium catalyst (36 mg). After stirring at 60° C. for 18 h, the mixture was cooled to 25° C., and volatiles were removed under a flow of nitrogen. The vial was removed from the glovebox, and the residue was triturated with MeOH. The precipitate that formed was isolated by filtration, washed with additional MeOH, and dried under reduced pressure. The vial was removed from the glovebox, and the residue was triturated with MeOH. The precipitate that formed was isolated by filtration, washed with additional MeOH, and dried under reduced pressure.

Example 7

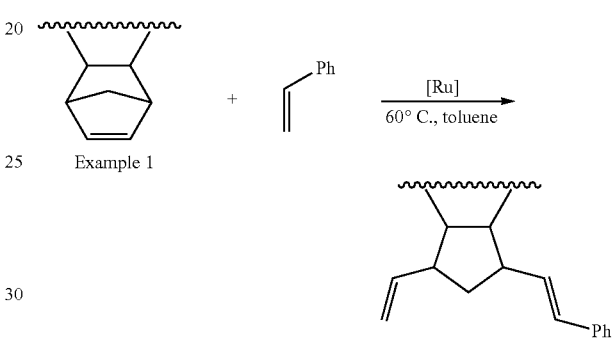

In the glovebox a 20 mL vial was charged with Resin A (0.6 g), toluene (6.0 mL), and a stirbar. With stirring, the solution was heated to 60° C. After all of Resin A had dissolved, styrene (0.23 mL) was added, followed by the ruthenium catalyst (36 mg). After stirring at 60° C. for 18 h, the mixture was cooled to 25° C., and volatiles were removed under a flow of nitrogen. The vial was removed from the glovebox, and the residue was triturated with MeOH. The precipitate that formed was isolated by filtration, washed with additional MeOH, and dried under reduced pressure.

Example 8

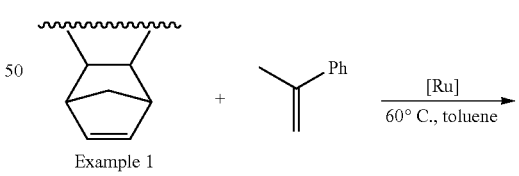

No Incorporation of Aryl Groups

In the glovebox a 20 mL vial was charged with Resin A (0.6 g), toluene (6.0 mL), and a stirbar. With stirring, the solution was heated to 60° C. After all of Resin A had dissolved, α-methylstyrene (0.25 mL) was added, followed by the ruthenium catalyst (36 mg). After stirring at 60° C. for 18 h, the mixture was cooled to 25° C., and volatiles were removed under a flow of nitrogen. The vial was removed from the glovebox, and the residue was triturated with MeOH. The precipitate that formed was isolated by filtration, washed with additional MeOH, and dried under reduced pressure.

Example 9

Control Adhesive Blend

Resin A from Example 1 (0.2 g) was blended with 1.0 g of a propylene hexene copolymer ("PH-1") and Polywax™ 3000 (0.1 g), a polyethylene wax available from Baker Hughes. Polywax™ 3000 is a synthetic wax that is a fully saturated homopolymers of ethylene that have high degrees of linearity and crystallinity. This synthetic wax has a density of about 0.98 g/cm$^3$ and a narrow molecular weight distribution. Properties of PH-1 and Polywax 3000 are further shown in the following table.

Number average molecular weight ($M_n$) and weight average molecular weight ($M_w$) were determined using a Polymer Laboratories Model 220 high temperature SEC with on-line differential refractive index (DRI), light scattering, and viscometer detectors. It used three Polymer Laboratories PLgel 10 m Mixed-B columns for separation using a flow rate of 0.54 ml/min and a nominal injection volume of 300 µL. The detectors and columns are contained in an oven maintained at 135° C. The light scattering detector is a high temperature miniDAWN (Wyatt Technology, Inc.). The primary components are an optical flow cell, a 30 mW, 690 nm laser diode light source, and an array of three photodiodes placed at collection angles of 45°, 90°, and 135°. The stream emerging from the SEC columns is directed into the miniDAWN optical flow cell and then into the DRI detector. The DRI detector is an integral part of the Polymer Laboratories SEC. The viscometer is a high temperature viscometer purchased from Viscotek Corporation and comprising four capillaries arranged in a Wheatstone bridge configuration with two pressure transducers. One transducer measures the total pressure drop across the detector, and the other, positioned between the two sides of the bridge, measures a differential pressure. The viscometer is inside the SEC oven, positioned after the DRI detector. The details of these detectors as well as their calibrations have been described by, for example, T. Sun, P. Brant, R. R. Chance, and W. W. Graessley, in Macromolecules, Volume 34, Number 19, pp. 6812-6820, (2001), incorporated herein by reference. Solvent for the SEC experiment was prepared by adding 6 grams of butylated hydroxy toluene (BHT) as an antioxidant to a 4 liter bottle of 1,2,4 trichlorobenzene (TCB) (Aldrich Reagent grade) and waiting for the BHT to solubilize. The TCB mixture was then filtered through a 0.7 micron glass pre-filter and subsequently through a 0.1 micron Teflon filter. There was an additional online 0.7 micron glass pre-filter/0.22 micron Teflon filter assembly between the high pressure pump and SEC columns. The TCB was then degassed with an online degasser (Phenomenex, Model DG-4000) before entering the SEC. Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units were 1.463 g/ml at 25° C. and 1.324 g/ml at 135° C. The injection concentration ranged from 1.0 to 2.0 mg/ml, with lower concentrations being used for higher molecular weight samples.

The values of $T_g$, $T_c$, $T_m$, and $H_f$ are based on DSC second melt.

|  |  | $M_w$ (kg/mole) | $M_w/M_n$ | BV@190° C. (mPa·sec) | $T_g$ (° C.) | $T_c$ (° C.) | $T_m$ (° C.) | $H_f$ (J/g) |
|---|---|---|---|---|---|---|---|---|
| PH-1 | 9 wt % hexene | 45 | 4.2 | 1486 | −9.1 | 62 | 120 | 35 |
| Polywax™ 3000 | 100 wt % C$_2$ | 3.3 | 1.15 | 55 |  | 115 | 127 |  |

The above mixture of Resin A Example 1, PH-1, and Polywax™ 3000 was dissolved in hot toluene (50 mL) and stirred until the mixture became homogeneous. Volatiles were then removed under a stream of N$_2$, and then the resin was dried in a vacuum oven.

Example 10

Modified Adhesive Blend

The functionalized material from Example 2 (0.2 g) was blended with PH-1 (1.0 g) and Polywax 3000 (0.1 g). The mixture was dissolved in hot toluene (50 mL) and stirred until the mixture became homogeneous. Volatiles were then removed under a stream of N$_2$, and then the resin was dried in a vacuum oven. The GPC data (40° C. in THF) for the unfunctionalized and the functionalized materials are compared in the next table.

|  | Resin A | Functionalized Material |
|---|---|---|
| $M_n$ (g/mol) | 546 | 683 |
| $M_w$ (g/mol) | 989 | 2874 |
| $M_w/M_n$ | 1.81 | 4.21 |
| $M_z$ (g/mol) | 2308 | 16682 |

Example 11

Brookfield Viscosity, Set Time, and Fiber Tear Test of Examples 9 & 10

Brookfield viscosity was measured using a Brookfield digital viscometer and a number 27 spindle according to ASTM D-3236 at either 177° C. or 190° C. (whichever temperature is specified). In order to measure set time and substrate fiber tear, adhesive test specimens are created by bonding the substrates together with a dot of about 0.3 grams of molten adhesive and compressing the bond with a 500-gram weight. The dot size is controlled by the adhesive volume such that the compressed disk which forms gives a uniform circle just inside the dimensions of the substrates.

Set time (also referred to as adhesive set time or dot set time) is defined as the time it takes for a compressed adhesive substrate construct to fasten together enough to give substrate fiber tear when pulled apart, and, thus, the bond is sufficiently strong to remove the compression. These set times are measured by trial and error by placing a molten dot of adhesive on to a file folder substrate (a typical manila letter size (⅓ cut) stock having a minimum of 10% post-consumer recycle paper content provided by Smead Paper, stock number 153L, UPC number 10330) taped to a flat table. Three seconds later, a file folder tab (2.5 cm×7.6 cm (1 inch by 3 inch)) is placed upon the dot and compressed with a 500-gram weight. The weight is allowed to sit for a predetermined time period from about 0.5 to about 10 seconds. The construct thus formed is pulled apart to check for a bonding level good enough to produce substrate fiber tear. The procedure is repeated several instances while holding the compression for different periods, and the set time is recorded as the minimum time required for this good bonding to occur. Standards are used to calibrate the process.

Once a construct is produced it can be subjected to various insults to assess the effectiveness of the bond. Once a bond to a substrate fails a simple way to quantify the effectiveness of the adhesive is to estimate the area of the adhesive dot that retained substrate fibers as the construct failed along the bond line. This estimate is called percent substrate fiber tear. An example of good adhesion, after conditioning a sample for 15 hours at −18° C. and attempting to destroy the bond, would be an estimate of 90% to 100% substrate fiber tear. It is likely that 0% substrate fiber tear under those conditions would signal a loss of adhesion.

The specimens for adhesion to a paper substrate for fiber tear testing are prepared using the same procedure as that described above. All substrate fiber tears were performed at conditions of 25° C., 2° C., and −18° C., wherein the specimens are aged at such conditions for about 12 hours. The bonds are separated by hand and a determination made as to the type of failure observed. The amount of substrate fiber tear is expressed herein as a percentage. All of the fiber tear tests are conducted using the paper substrate of a paperboard 84C (generic corrugated cardboard 200# stock provided by Huckster Packaging Supply, 6111 Griggs Road, Houston Tex. 77023).

The performance of the two adhesive blends is shown in the table below.

|  | Example 9 | Example 10 |
| --- | --- | --- |
| PH-1 | 76.9 wt % | 76.9 wt % |
| Resin A | 15.4 wt % | — |
| Functionalized Material from Ex. 2 | — | 15.4 wt % |
| Polywax ™ 3000 | 7.7 wt % | 7.7 Wt % |
| HMA Performance |  |  |
| Brookfield Viscosity @ 177° C., mPa · s | 705 | 1292 |
| Set Time, s | 2.0 | 1.75 |
| % Fiber Tear to 84C, 25° C. | 100 | 99 |
| % Fiber Tear to 84C, 2° C. | 99 | 100 |
| % Fiber Tear to 84C, −18° C. | 85 | 98 |
| $T_g$, ° C. | −14 | −15 |
| $T_c$, ° C. | 87 | 88 |
| $T_m$, ° C. | 77, 121 | 79, 121 |
| $H_f$, J/g | 25 | 24 |

Example 10 shows a good Fiber Tear result at −18° C. so that it is suitable to be used as a freezer packaging adhesive compared to Example 9. Without being bound by theory, it is believed that the extra polar interactions between the functionalized material in Example 10 and the cardboard substrate enhance this low-temperature adhesion. Note that both Examples 9 and 10 have $T_g$ values higher than −18° C., the normal freezer temperature. Besides PH-1, it is expected that $C_3/C_2$ copolymers, other propylene-based polymers, ethylene-based polymers, etc., can be used as the base polymer of the adhesive blend with the functionalized material of this invention.

All documents described herein are incorporated by reference herein, including any priority documents and/or testing procedures to the extent they are not inconsistent with this text, provided however that any priority document not named in the initially filed application or filing documents is NOT incorporated by reference herein. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including" for purposes of Australian law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa. Thus, the term "comprising" encompasses the terms "consisting essentially of," "is," and "consisting of" and anyplace "comprising" is used "consisting essentially of," "is," or consisting of may be substituted therefor.

The invention claimed is:

1. A composition comprising one or more of the formulae:

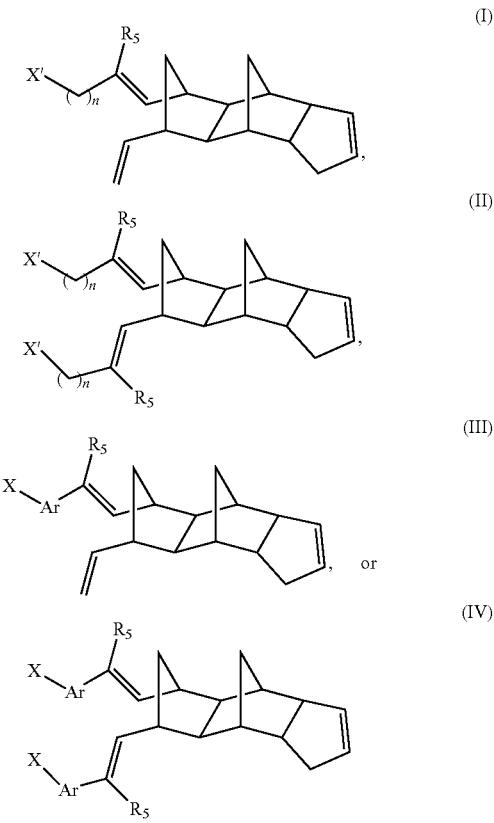

wherein,
optionally, one or more positions on the polymeric backbone can be substituted with an aromatic group;
each X is, independently, —$CO_2R$, —$CONR_1R_2$, CN, a $C_1$ to a $C_{20}$ alkyl group;

each X' is, independently, —CO$_2$R, —CONR$_1$R$_2$, CN, a C$_1$ to a C$_{20}$ alkyl group, or a residual terminal portion of a vinyl terminated macromonomer (VTM);
R is a C$_1$ to a C$_{20}$ alkyl group or an aromatic group;
each R$_1$ and R$_2$ is, independently, a hydrogen, a C$_1$ to a C$_{20}$ alkyl group, or an aromatic group;
each R$_5$ is, independently, a hydrogen atom or a C$_1$ to a C$_{40}$ alkyl group;
each Ar is, independently, an aromatic group; and
each n is, independently, from 0 to about 40.

2. The composition of claim 1, wherein R$_1$ and R$_2$ are hydrogen atoms.

3. A hot melt adhesive comprising the reaction product of DCPD polymer and at least one of

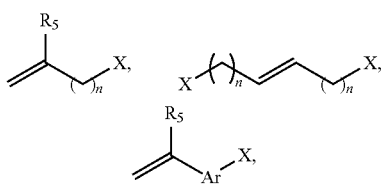

or a vinyl terminated macromonomer (VTM) with a metathesis catalyst,
wherein,
optionally, one or more positions on the polymeric backbone can be substituted with an aromatic group;
each X is, independently, —CO$_1$R, —CONR$_1$R$_2$, CN, a C$_1$ to a C$_{20}$ alkyl group;
R is a C$_1$ to a C$_{20}$ alkyl group or an aromatic group;
each R$_1$ and R$_2$ is, independently, a hydrogen, a C$_1$ to a C$_{20}$ alkyl group, or an aromatic group;
each R$_5$ is, independently, a hydrogen atom or a C$_1$ to a C$_{40}$ alkyl group;
each Ar is, independently, an aromatic group; and
each n is, independently, from 0 to about 40.

4. A composition comprising the reaction product of a DCPD polymer and at least one of

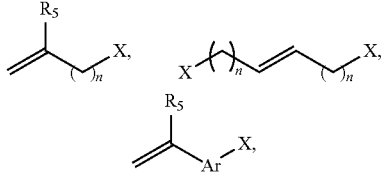

or a vinyl terminated macromonomer (VTM) with a metathesis catalyst,
wherein,
optionally, one or more positions on the polymeric backbone can be substituted with an aromatic group;
each X is, independently, —CO$_1$R, —CONR$_1$R$_2$, CN, or a C$_1$ to a C$_{20}$ alkyl group;
R is a C$_1$ to a C$_{20}$ alkyl group or an aromatic group;
each R$_1$ and R$_2$ is, independently, a hydrogen, a C$_1$ to a C$_{20}$ alkyl group, or an aromatic group;
each R$_5$ is, independently, a hydrogen atom or a C$_1$ to a C$_{40}$ alkyl group;
each Ar is, independently, an aromatic group; and
each n is, independently, from 0 to about 40.

5. A composition comprising one or more of the formulae:

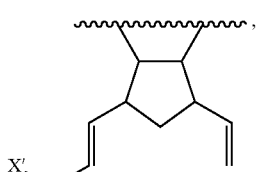 (V)

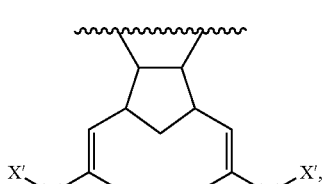 (VI)

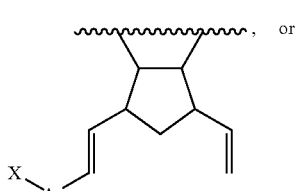 (VII)

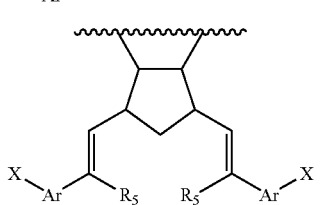 (VIII)

wherein,
∿∿∿∿ represents the polymeric backbone;
optionally, one or more positions on a polymeric backbone can be substituted with an aromatic group;
each X is, independently, —CO$_1$R, —CONR$_1$R$_2$, CN, or a C$_1$ to a C$_{20}$ alkyl group;
each X' is, independently, —CO$_1$R, —CONR$_1$R$_2$, CN, a C$_1$ to a C$_{20}$ alkyl group or, the residual terminal portion of a vinyl terminated macromonomer (VTM);
R is a C$_1$ to a C$_{20}$ alkyl group or an aromatic group;
each R$_1$ and R$_2$ is, independently, a hydrogen, a C$_1$ to a C$_{20}$ alkyl group, or an aromatic group;
each R$_5$ is, independently, a hydrogen atom or a C$_1$ to a C$_{40}$ alkyl group;
each Ar is, independently, an aromatic group; and
each n is, independently, from 0 to about 40.

6. The composition of claim 5, wherein R$_1$ and R$_2$ are hydrogen atoms.

7. A hot melt adhesive comprising the reaction product of a DCPD polymer and one or more of

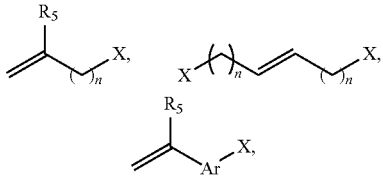

or a vinyl terminated macromonomer (VTM) with a metathesis catalyst, optionally, one or more positions on the polymeric backbone can be substituted with an aromatic group;

each X is, independently, —CO$_1$R, —CONR$_1$R$_2$, CN, a C$_1$ to a C$_{20}$ alkyl group;

R is a C$_1$ to a C$_{20}$ alkyl group or an aromatic group;

each R$_1$ and R$_2$ is, independently, a hydrogen, a C$_1$ to a C$_{20}$ alkyl group, or an aromatic group;

each R$_5$ is, independently, a hydrogen atom or a C$_1$ to a C$_{40}$ alkyl group;

each Ar is, independently, an aromatic group; and each n is, independently, from 0 to about 40.

8. A composition comprising the reaction product of a DCPD polymer and one or more of

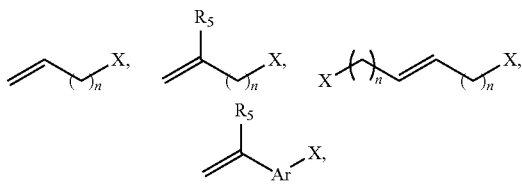

or a vinyl terminated macromonomer (VTM) with a metathesis catalyst, wherein, optionally, one or more positions on the polymeric backbone can be substituted with an aromatic group;

each X is, independently, —CO$_1$R, —CONR$_1$R$_2$, CN, or a C$_1$ to a C$_{20}$ alkyl group;

R is a C$_1$ to a C$_{20}$ alkyl group or an aromatic group;

each R$_1$ and R$_2$ is, independently, a hydrogen, a C$_1$ to a C$_{20}$ alkyl group, or an aromatic group;

each R$_5$ is, independently, a hydrogen atom or a C$_1$ to a C$_{40}$ alkyl group;

each Ar is, independently, an aromatic group; and each n is, independently, from 0 to about 40.

9. The composition of claim 8 wherein the DCPD polymer is prepared from DCPD monomer having less than 100 ppm sulfur.

* * * * *